(12) United States Patent
Rolland

(10) Patent No.: US 11,890,743 B2
(45) Date of Patent: Feb. 6, 2024

(54) HANDLE COMPOSITIONS, METHODS OF USE AND METHODS OF MAKING

(71) Applicant: Benoit Rolland, Watertown, MA (US)

(72) Inventor: Benoit Rolland, Watertown, MA (US)

( * ) Notice: Subject to any disclaimer, the term of this patent is extended or adjusted under 35 U.S.C. 154(b) by 745 days.

(21) Appl. No.: 16/630,397

(22) PCT Filed: Jul. 16, 2018

(86) PCT No.: PCT/US2018/042314
§ 371 (c)(1),
(2) Date: Jan. 10, 2020

(87) PCT Pub. No.: WO2019/014679
PCT Pub. Date: Jan. 17, 2019

(65) Prior Publication Data
US 2020/0376647 A1 Dec. 3, 2020

Related U.S. Application Data

(60) Provisional application No. 62/532,656, filed on Jul. 14, 2017.

(51) Int. Cl.
*B25G 1/10* (2006.01)
*A47J 45/10* (2006.01)
*A61B 17/3211* (2006.01)
*A61B 17/00* (2006.01)

(52) U.S. Cl.
CPC ............. *B25G 1/102* (2013.01); *A47J 45/10* (2013.01); *A61B 17/3211* (2013.01); *A61B 2017/00424* (2013.01); *A61B 2017/00526* (2013.01)

(58) Field of Classification Search
CPC ...... B25G 1/102; A47J 45/10; A61B 17/3211; A61B 17/2909; A61B 2017/00424; A61B 2017/00526; A61B 2017/0042; Y10T 16/476
USPC .......................................................... 16/430
See application file for complete search history.

(56) References Cited

U.S. PATENT DOCUMENTS

| 2,124,615 | A | | 8/1935 | Foltz |
| 2,962,288 | A | * | 11/1960 | Lowden ............... A63B 53/007 473/206 |
| D209,902 | S | | 1/1968 | Watson |
| D212,811 | S | | 11/1968 | Miller |
| D225,528 | S | | 12/1972 | Tate |
| D230,468 | S | | 2/1974 | Fairbairn |

(Continued)

FOREIGN PATENT DOCUMENTS

| CN | 101579564 A | 11/2009 |
| CN | 201418478 Y | 3/2010 |

(Continued)

OTHER PUBLICATIONS

Newland Custom Batons: Fine Conducting Batons handcrafted to your exact specifications, (2018). Retrieved from the internet on Nov. 14, 2018: http://www.newlandbatons.com/index.html.

(Continued)

*Primary Examiner* — William L Miller
(74) *Attorney, Agent, or Firm* — COOLEY LLP

(57) ABSTRACT

The disclosure is generally directed to handles or hand grips, and more specifically, to handles with attached instruments, compositions of matter used to make such handles, and methods of making and using the same.

16 Claims, 68 Drawing Sheets

(56) References Cited

U.S. PATENT DOCUMENTS

| | | | |
|---|---|---|---|
| D231,043 S | 3/1974 | Barnett | |
| D231,044 S | 3/1974 | Morris | |
| D240,367 S | 6/1976 | Cope | |
| D240,495 S | 7/1976 | Koppe | |
| D241,508 S | 9/1976 | Agate | |
| D241,806 S | 10/1976 | Johnson | |
| 4,836,544 A | 6/1989 | Lai | |
| 4,934,024 A * | 6/1990 | Sexton, I | B29D 15/00 264/222 |
| 5,076,569 A | 12/1991 | Gootter | |
| 5,155,878 A | 10/1992 | Dellis | |
| D348,819 S | 7/1994 | Craig | |
| 5,588,651 A | 12/1996 | Frost | |
| 5,657,985 A | 8/1997 | Dahlstrom et al. | |
| 5,692,265 A | 12/1997 | Dalury | |
| 5,761,767 A * | 6/1998 | Barton | A45C 13/26 16/901 |
| 5,979,015 A | 11/1999 | Tamaribuchi | |
| D486,718 S | 2/2004 | Goddert | |
| 7,284,300 B1 | 10/2007 | Bruns | |
| D569,939 S | 5/2008 | Edwards | |
| D573,351 S * | 7/2008 | Angers | D4/138 |
| 7,758,455 B2 * | 7/2010 | Thomas | A63B 60/00 473/551 |
| 8,092,411 B2 | 1/2012 | Betcher | |
| 8,616,098 B1 | 12/2013 | Rosow | |
| 8,708,846 B2 | 4/2014 | Hisle, Jr. et al. | |
| 8,769,835 B2 | 7/2014 | Luttgens | |
| D710,942 S | 8/2014 | Pincus et al. | |
| D713,460 S | 9/2014 | Pierce | |
| 8,931,855 B1 | 1/2015 | Foley et al. | |
| 2003/0074766 A1 | 4/2003 | Dalury | |
| 2004/0199205 A1 | 10/2004 | Tillim | |
| 2005/0150083 A1 | 7/2005 | Roberts | |
| 2005/0241111 A1 | 11/2005 | Prokop | |
| 2007/0062006 A1 | 3/2007 | Wright | |
| 2007/0137051 A1* | 6/2007 | Luttgens | B43L 23/08 30/451 |
| 2007/0204435 A1* | 9/2007 | Pangborn | B25G 1/102 16/430 |
| 2007/0251059 A1 | 11/2007 | You | |
| 2008/0032832 A1 | 2/2008 | Thomas | |
| 2013/0005401 A1 | 1/2013 | Rosenhan et al. | |
| 2013/0036873 A1 | 2/2013 | Wood | |
| 2013/0180067 A1 | 7/2013 | Haigh et al. | |
| 2013/0192028 A1 | 8/2013 | Pierce | |
| 2018/0169852 A1 | 6/2018 | Fryer-Biggs et al. | |
| 2021/0307501 A1* | 10/2021 | Pianka | B25G 1/102 |

FOREIGN PATENT DOCUMENTS

| | | |
|---|---|---|
| CN | 201987152 U | 9/2011 |
| CN | 202199065 U | 4/2012 |
| CN | 203815825 U | 9/2014 |
| CN | 104756034 A | 7/2015 |
| CN | 104921429 A | 9/2015 |
| JP | H0789523 A | 4/1995 |
| JP | H0810395 A | 1/1996 |
| JP | 3085138 U | 4/2002 |
| JP | 2002102434 A | 4/2002 |
| JP | 2006123086 A | 5/2006 |
| JP | 2006223601 A | 8/2006 |
| JP | 2009072621 A | 4/2009 |
| WO | WO-03018144 A1 | 3/2003 |

OTHER PUBLICATIONS

PaGu Batons, Flat Spot Series, (2018). Retrieved from the internet on Nov. 14, 2018: https://www.pagubatons.com/Flat-Spot-Series_c_43.html.

Conducting Batons, Collection by Adam Tatus, (2018). Retrieved from the internet on Nov. 14, 2018: https://www.pinterest.com/adamtatum1/conducting-batons/.

Mollard Conducting Batons, Baton Guide, (2018). Retrieved from the internet on Nov. 14, 2018: https://mollard.com/baton-guide/.

Custom Batons, (2018). Retrieved from the internet on Nov. 14, 2018: https://www.custombatons.net/.

Martinson Batons, (2018). Retrieved from the internet on Nov. 14, 2018: https://www.custombatons.net/.

Music, Conducting, Photography and various mindful meanderings, Jun. 20, 2009. Retrieved from the internet on Nov. 14, 2018: http://davidoertel.blogspot.com/2009/06/orchestral-conductors-baton.html.

GL Custom Batons, N. Guy Lake Conductor-Craftsman. Retrieved from the internet on Nov. 14, 2018: http://www.glcustombatons.com/graphitebatons.html.

Pierce Batons LLC, Signature Conducting Batons, (2007). Retrieved from the internet on Nov. 14, 2018: http://www.alanpierceconductingbatons.com/signatureconductingbatons.html.

Gruber, R. E. "A conductor's batons cast a magical spell", The New York Times, 3 pages, (Mar. 31, 2005).

Hoffman, D. "From A Master, Batons That Aren't Just Sticks", The New York Times, (Aug. 22, 1988).

Napoles, J. et al. "Effects of Conductor Baton Use on Band and Choral Musicians' Perceptions of Conductor Expressivity and Clarity", Journal of Research in Music Education, vol. 64, Issue 4, p. 474-486 (2017).

Platte, S. L. "The Maestro Myth-Exploring the Impact of Conducting Gestures on the Musician's body and the Sounding Result", Masters Degree Thesis, M.A. Visual Communication and Iconic Research, 116 pages, (2014).

Wakin, D. J. "The Maestro's Mojo", The New York Times, 7 pages, (Apr. 6, 2012).

Office Action for Japanese Application No. JP20200501477 dated Apr. 17, 2023, 12 pages.

Office Action for Japanese application No. JP20200501477, dated Aug. 1, 2022, 28 pages.

* cited by examiner

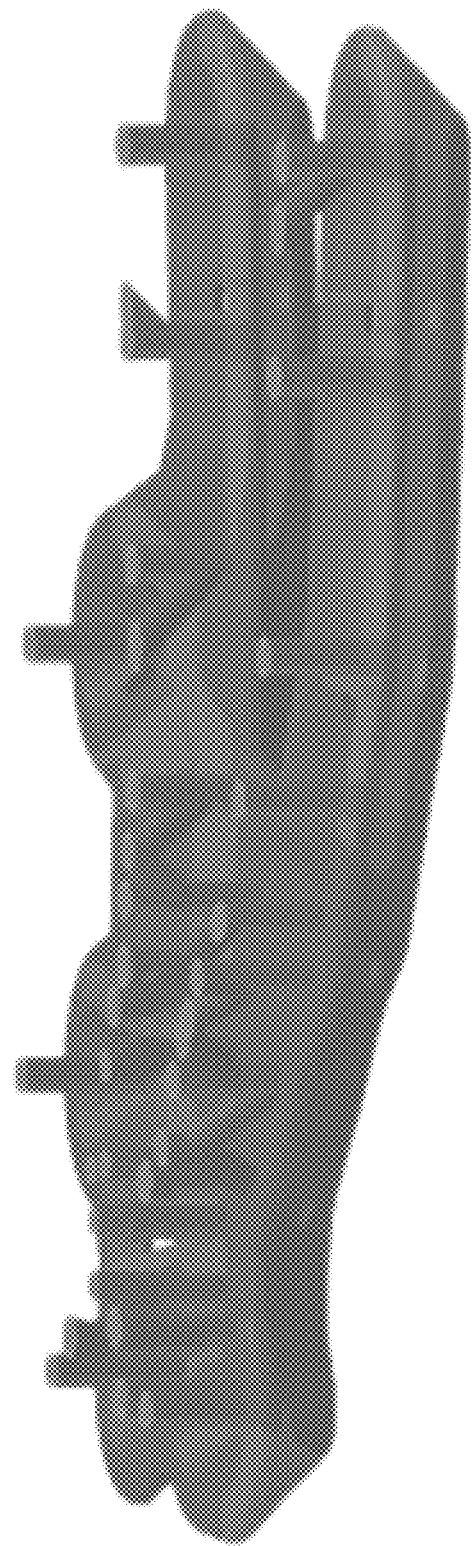
FIG. 10A – 67 slices

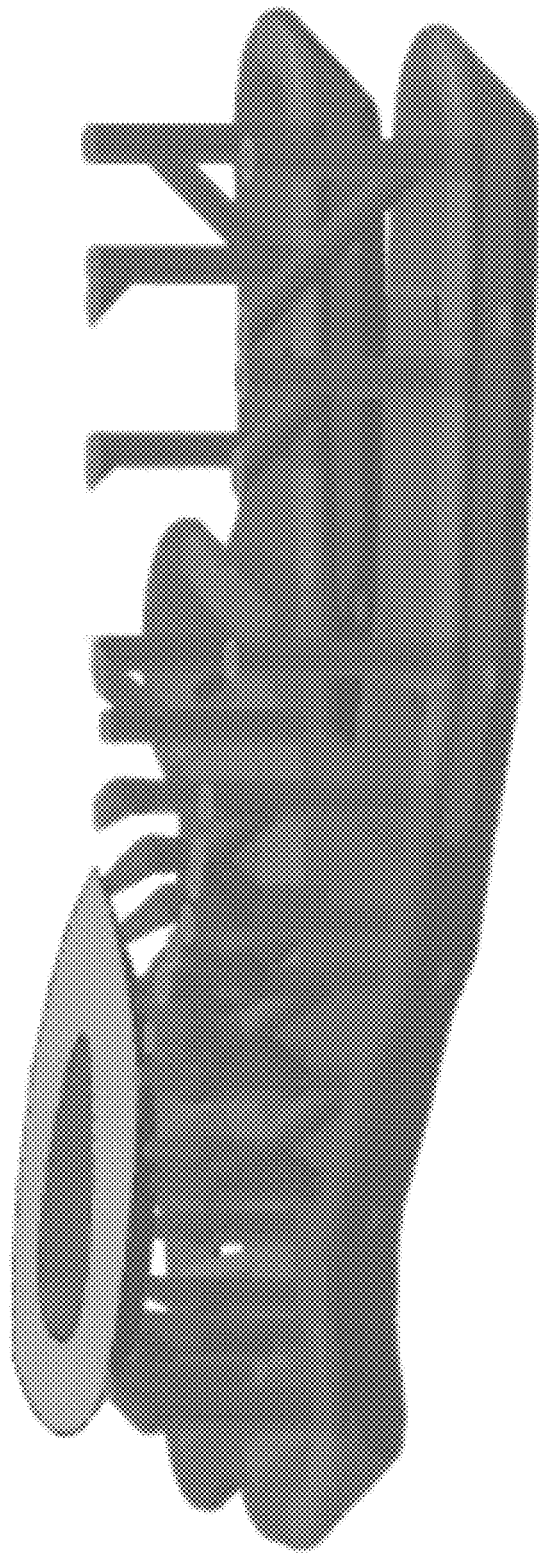
FIG. 10B – 139 slices

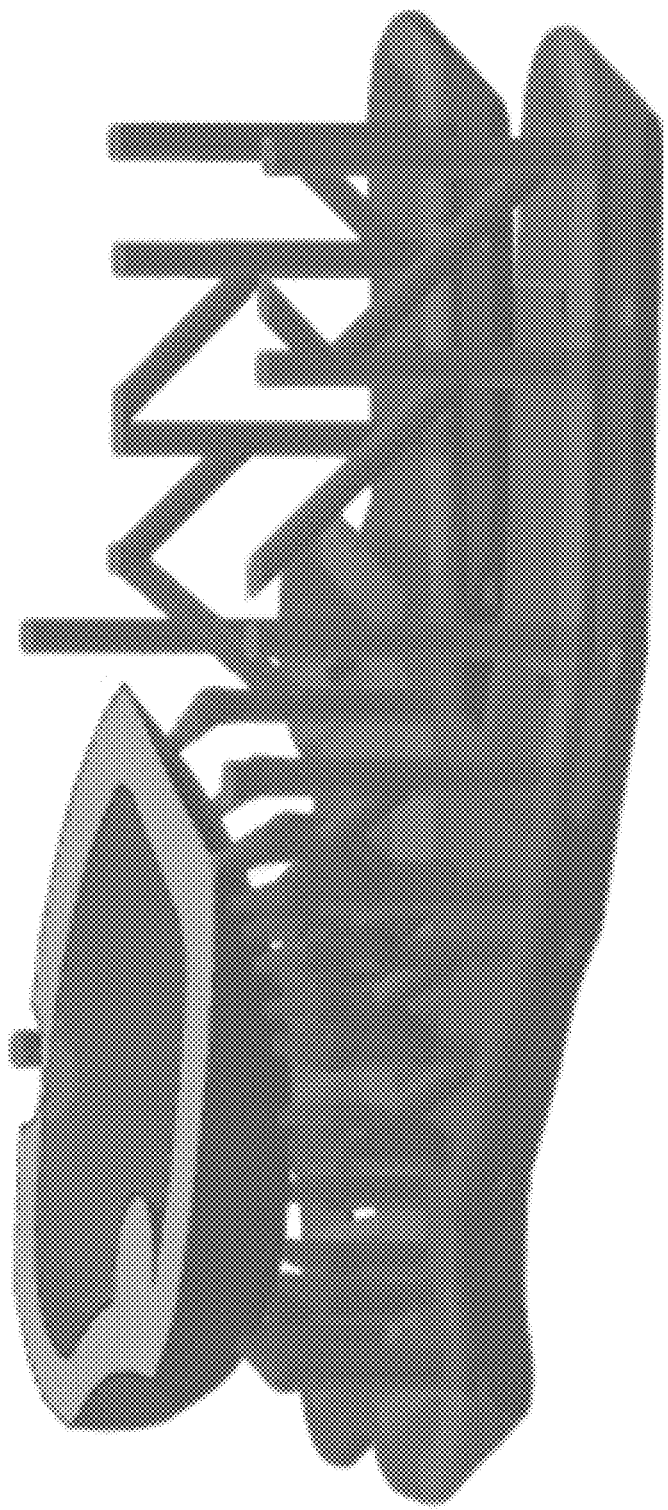
FIG. 10C – 221 slices

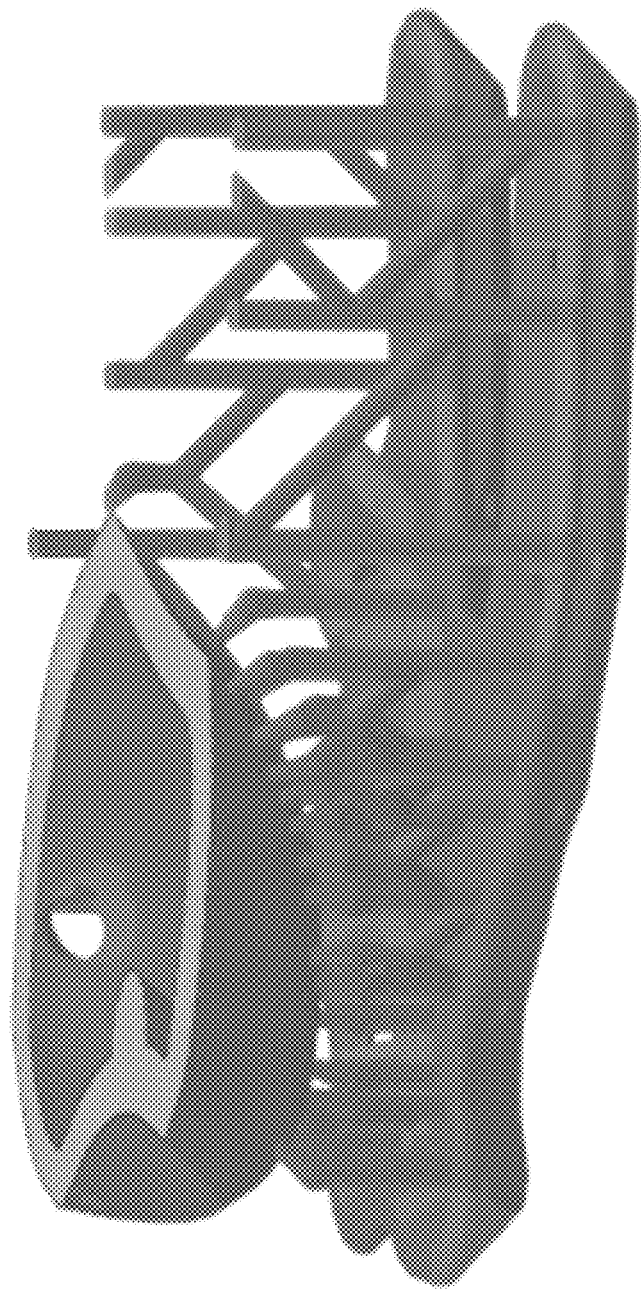
FIG. 10D – 275 slices

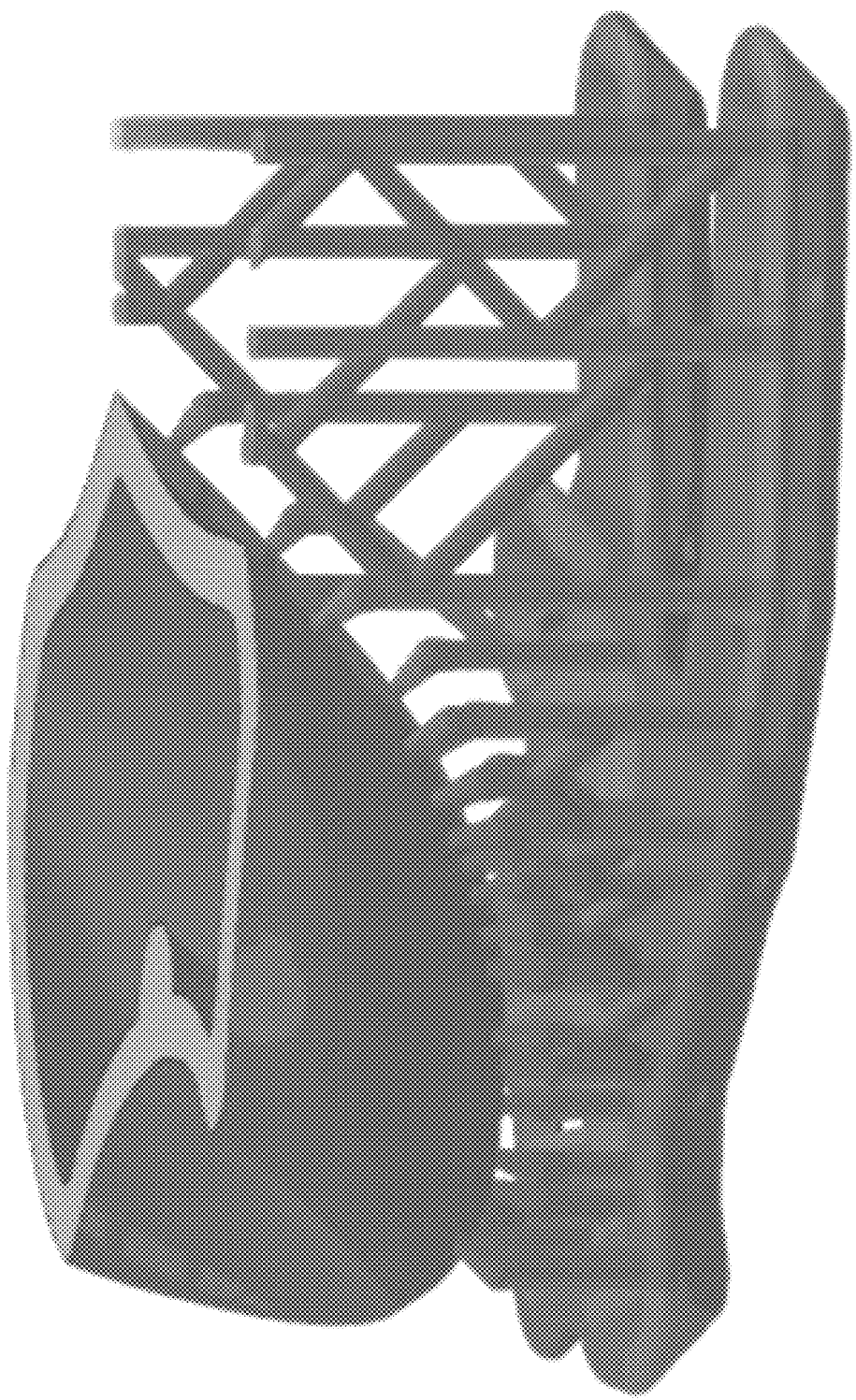
FIG. 10E – 399 slices

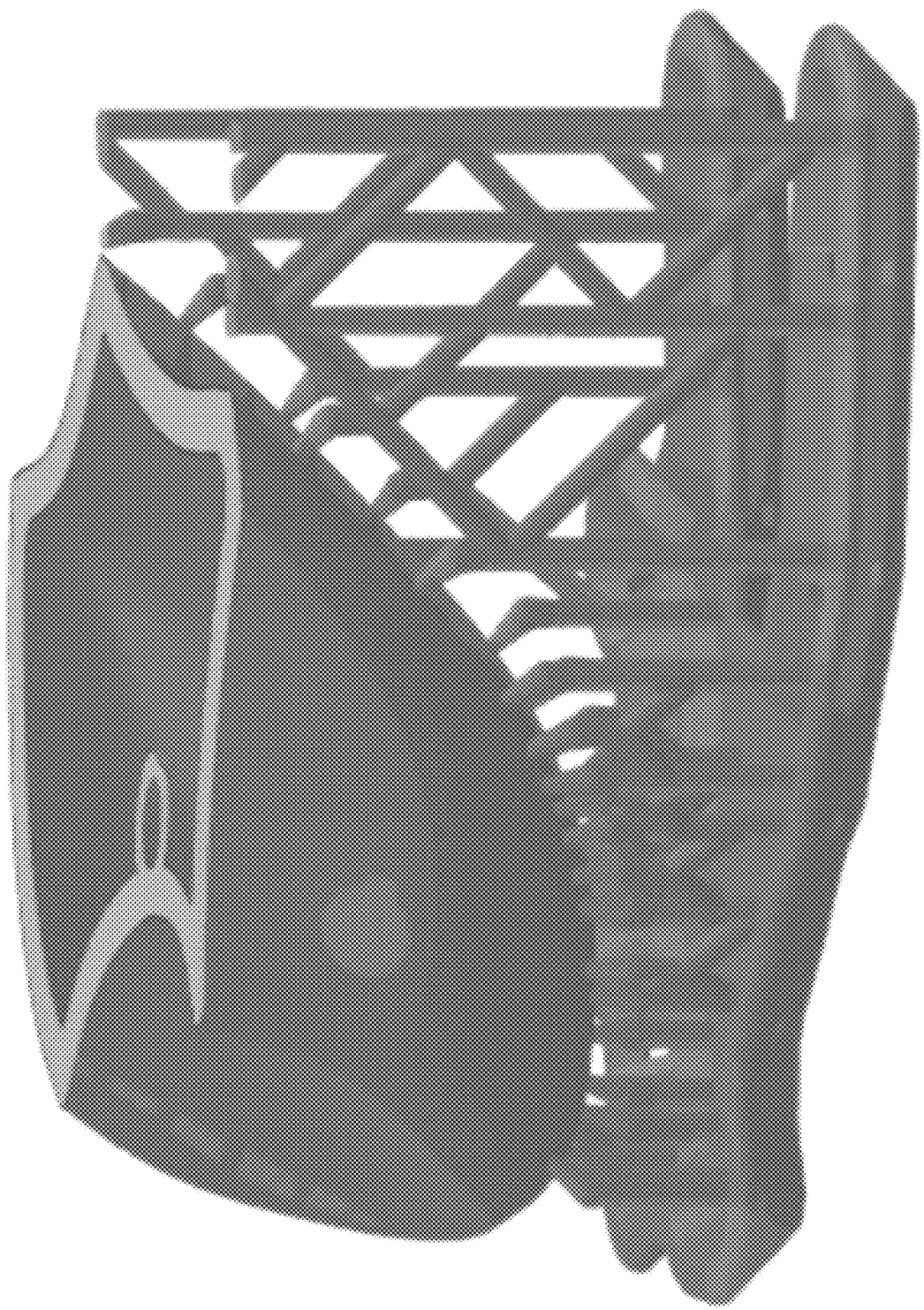
FIG. 10F – 508 slices

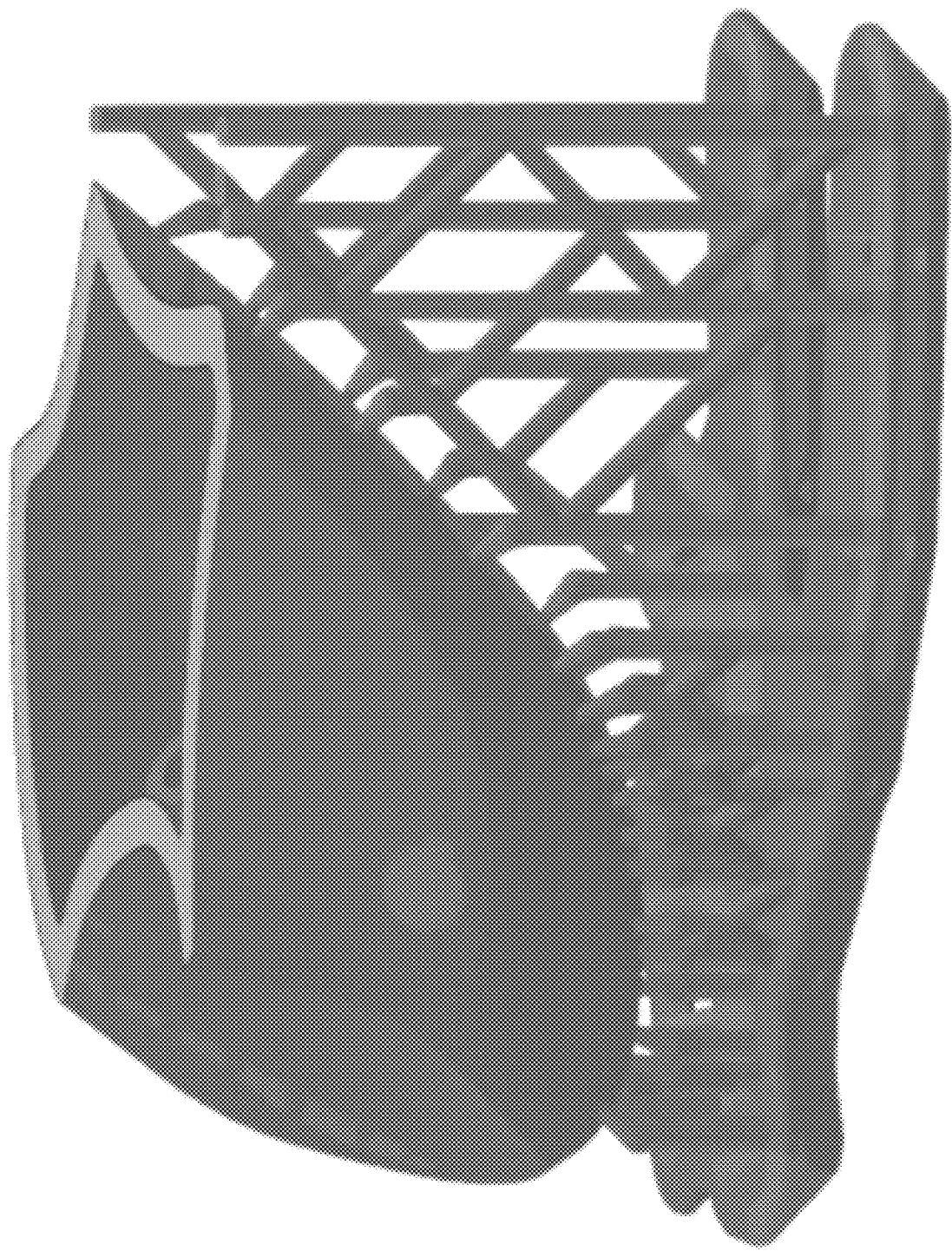
FIG. 10G – 576 slices

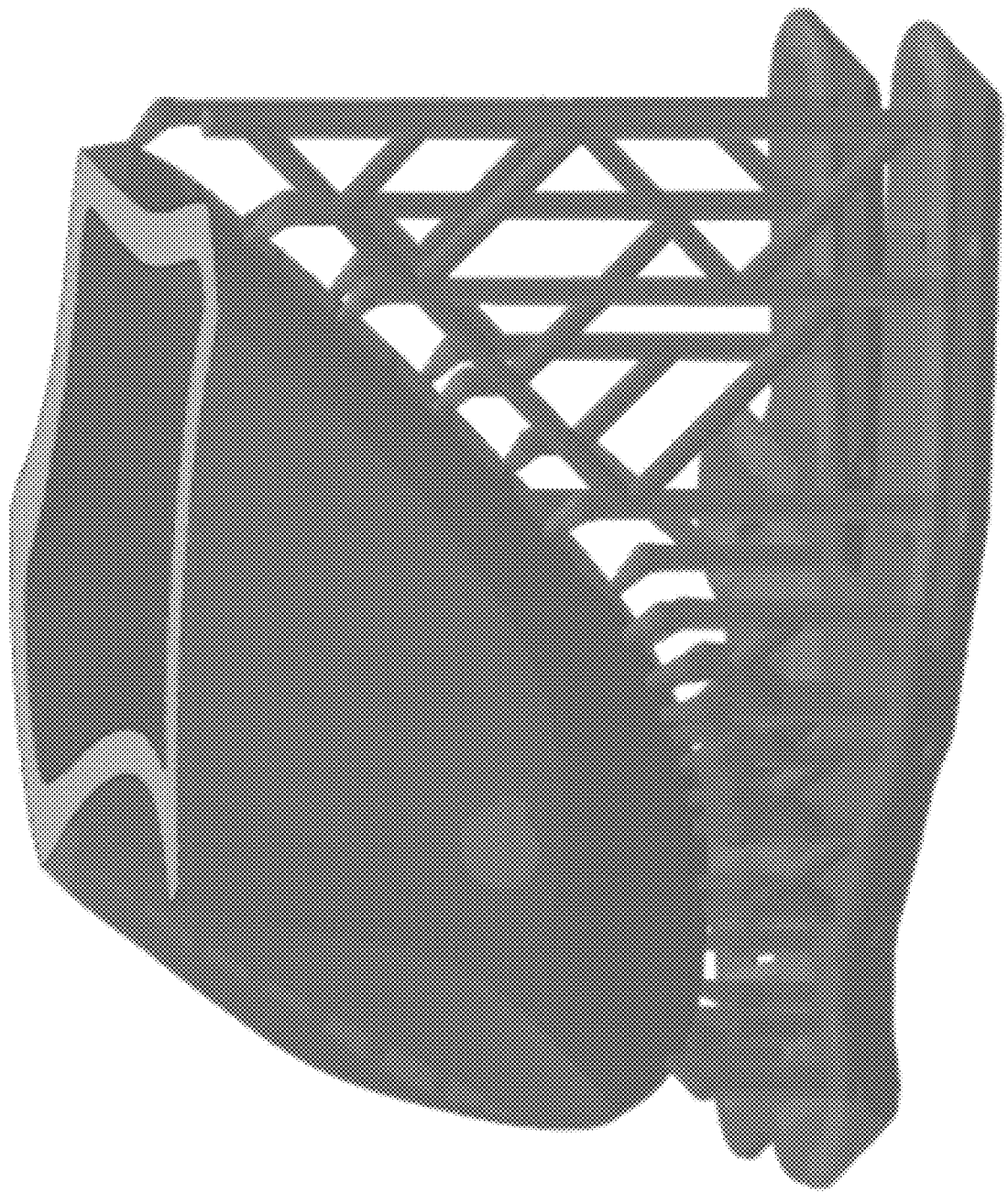
FIG. 10H – 669 slices

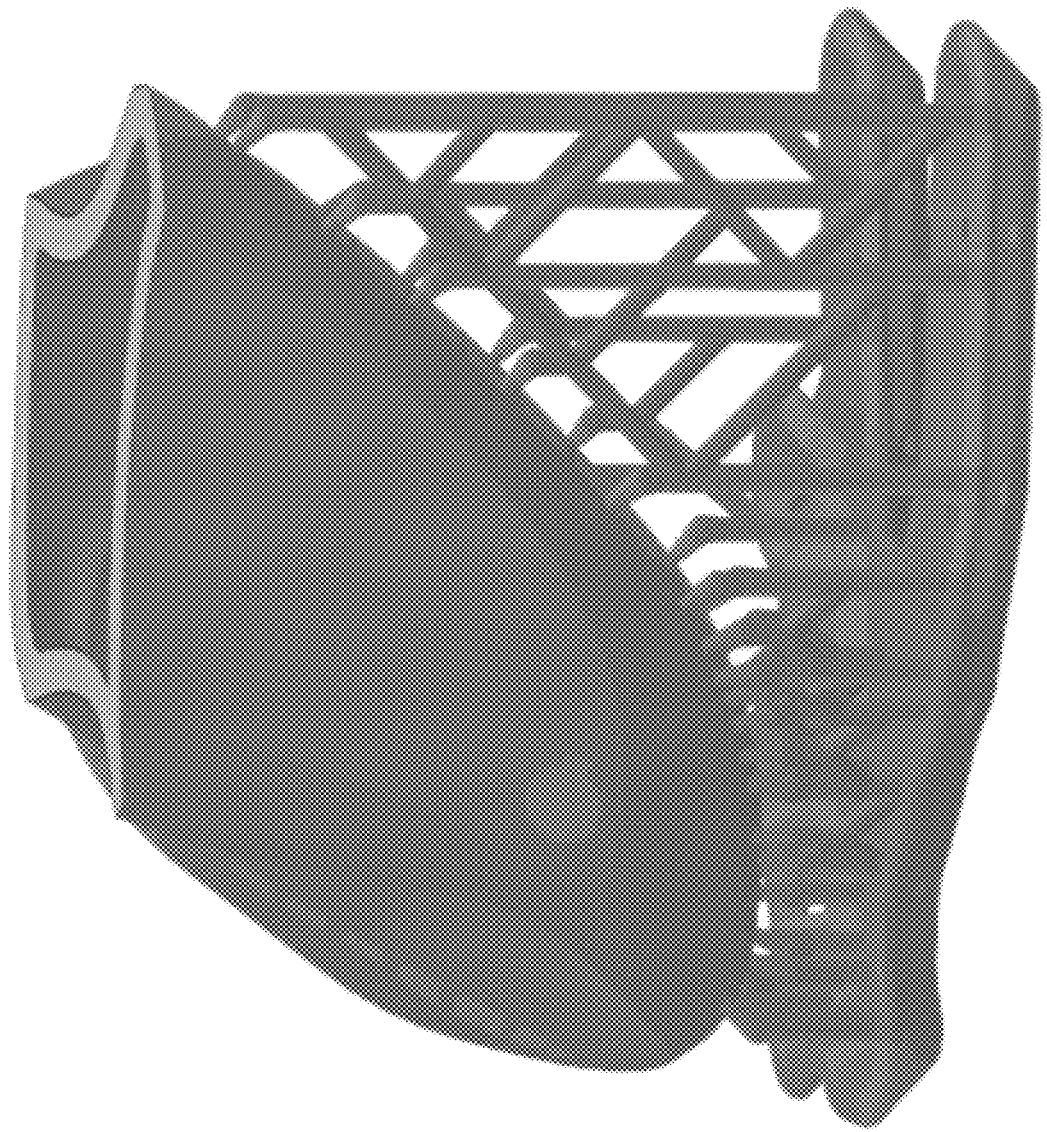
FIG. 10I – 802 slices

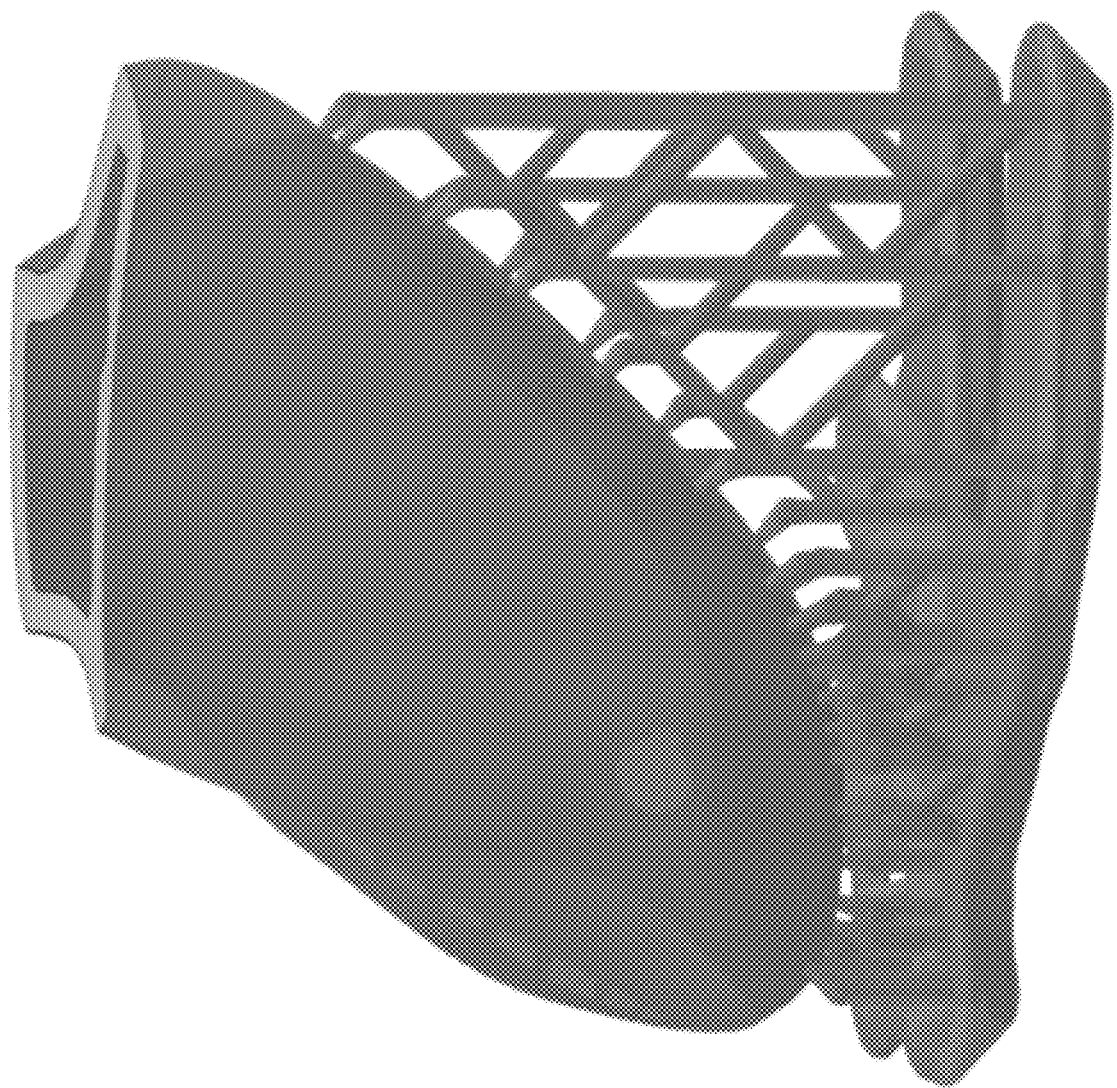
FIG. 10J – 932 slices

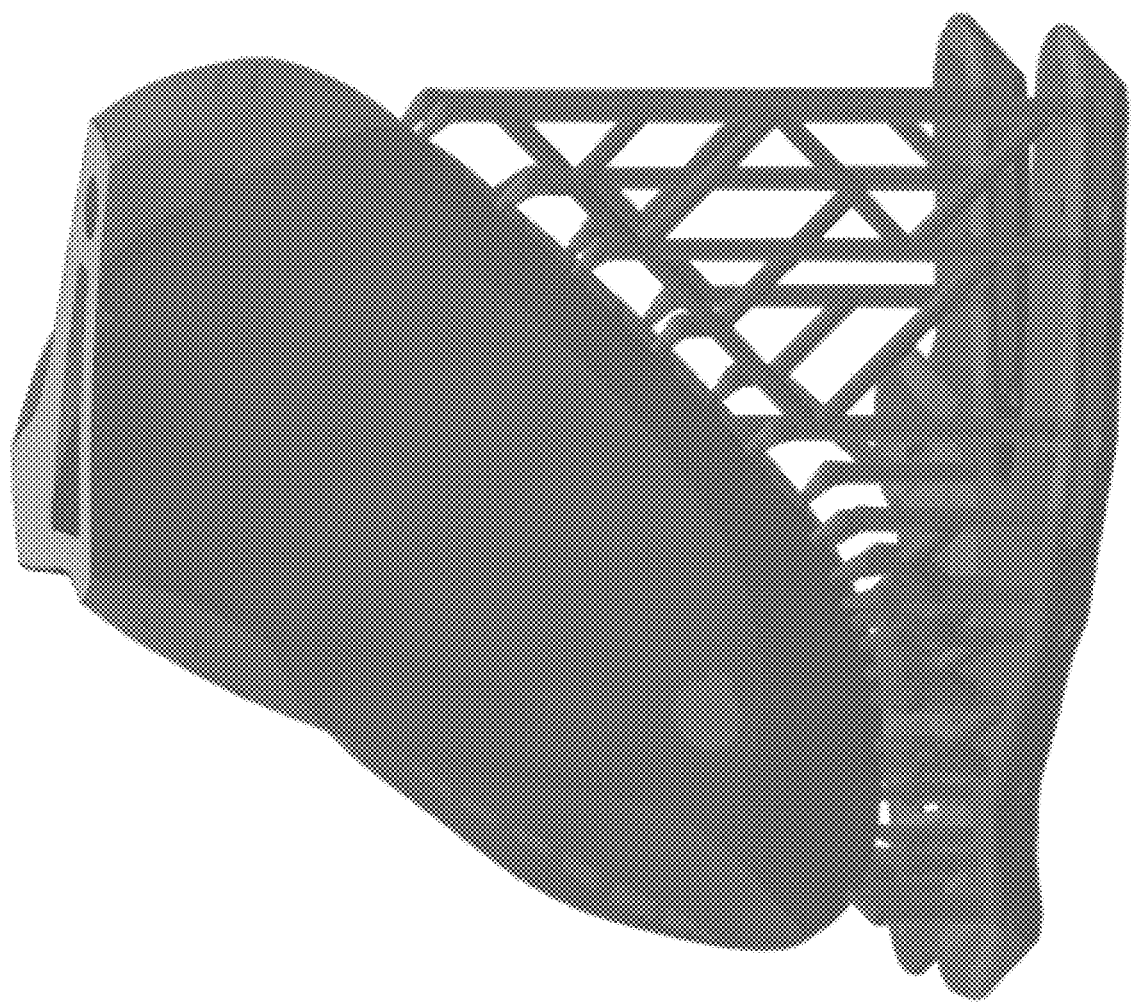
FIG. 10K – 1066 slices

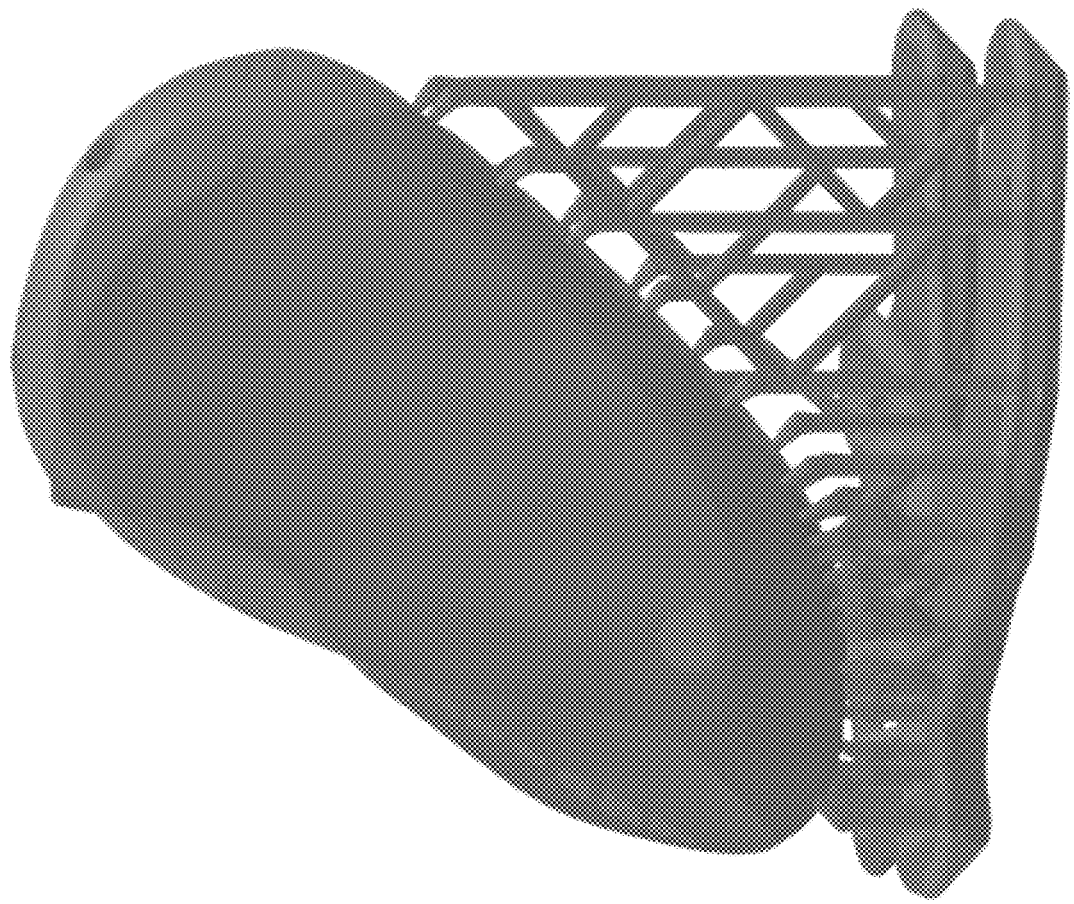
FIG. 10L – 1199 slices

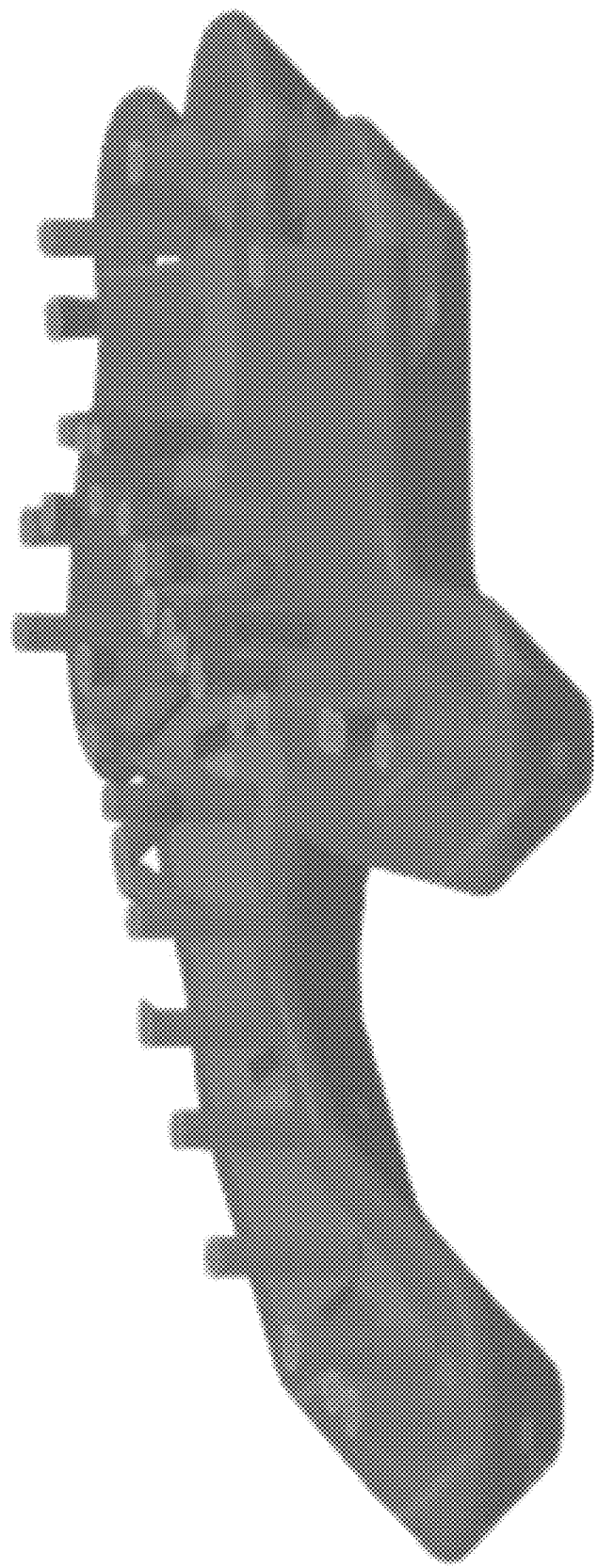
FIG. 10M – 67 slices

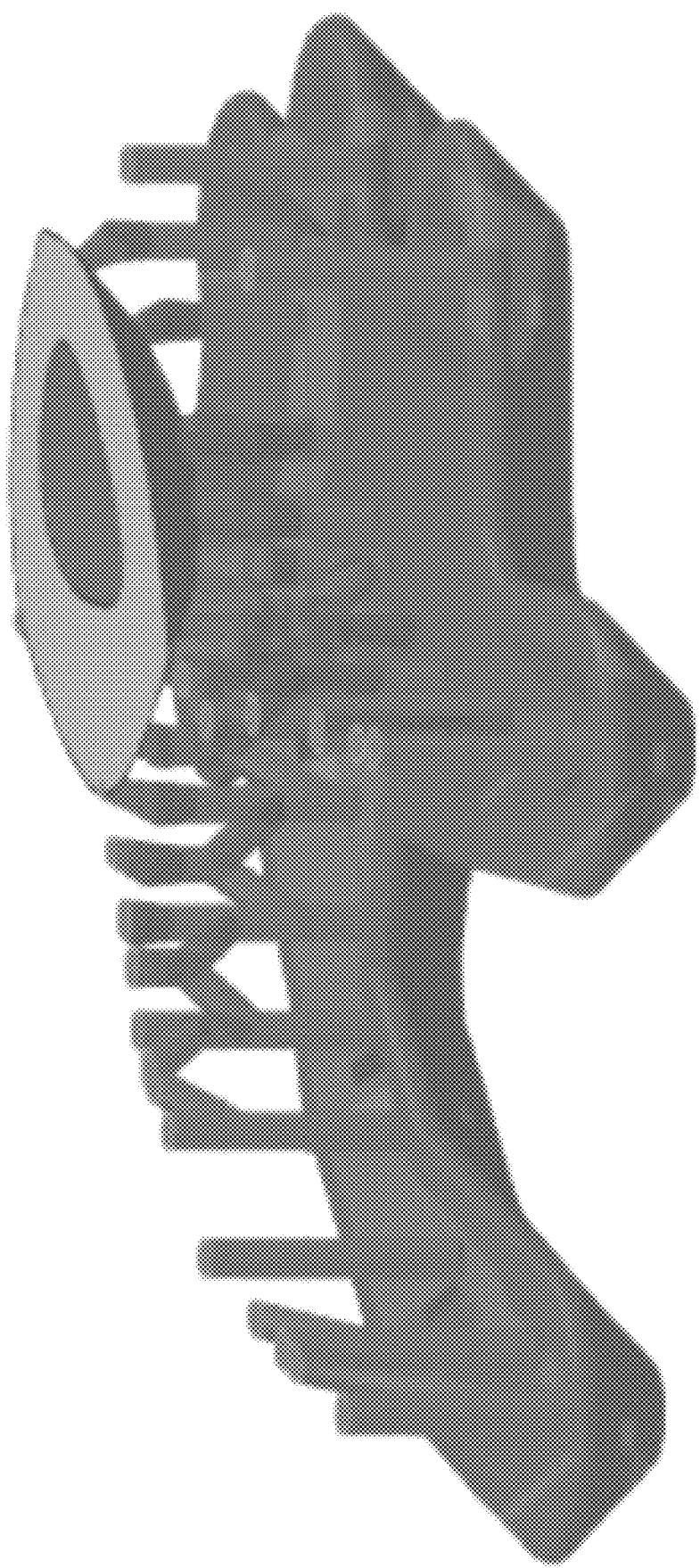
FIG. 10N – 139 slices

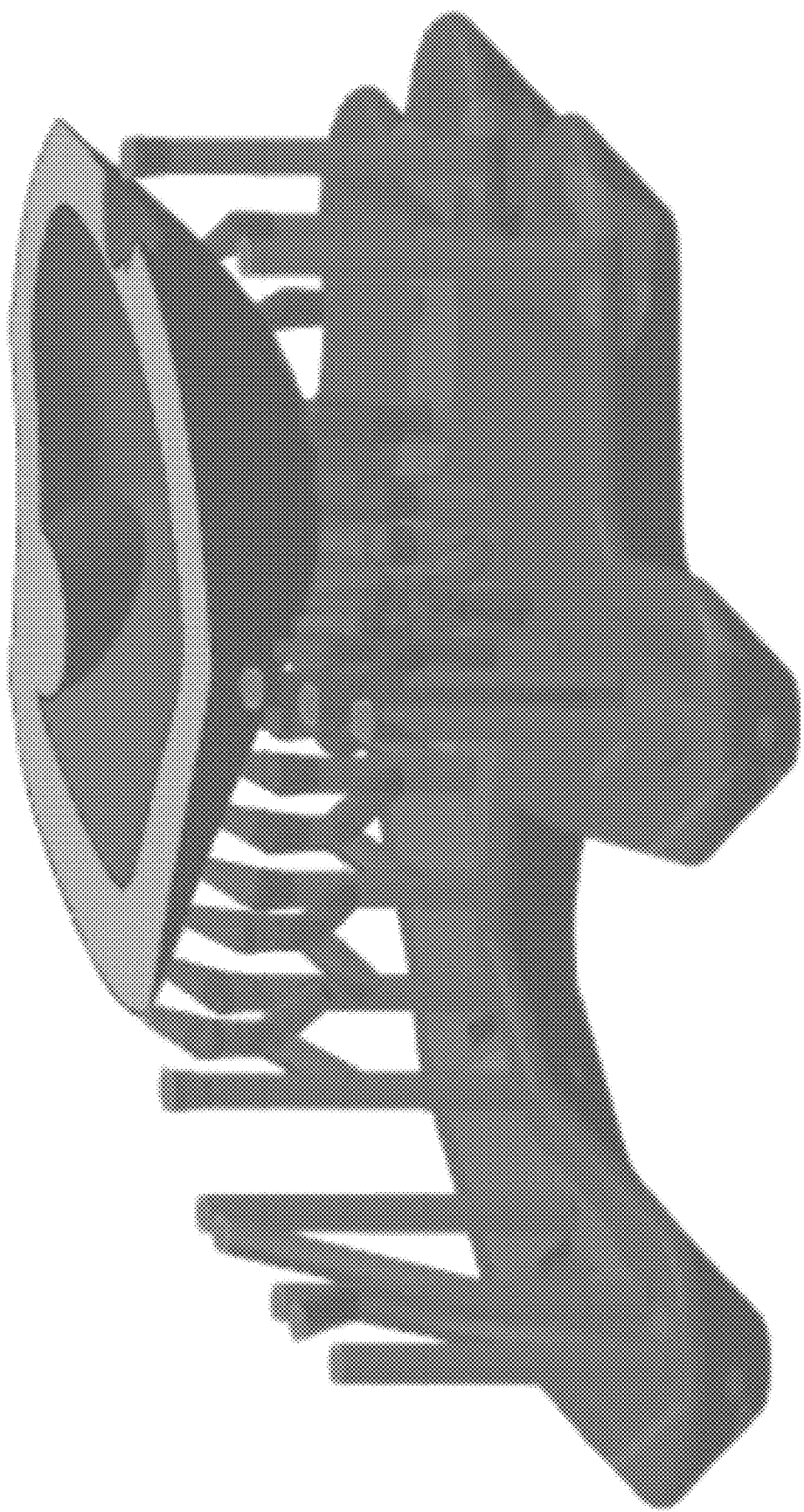
FIG. 100 – 221 slices

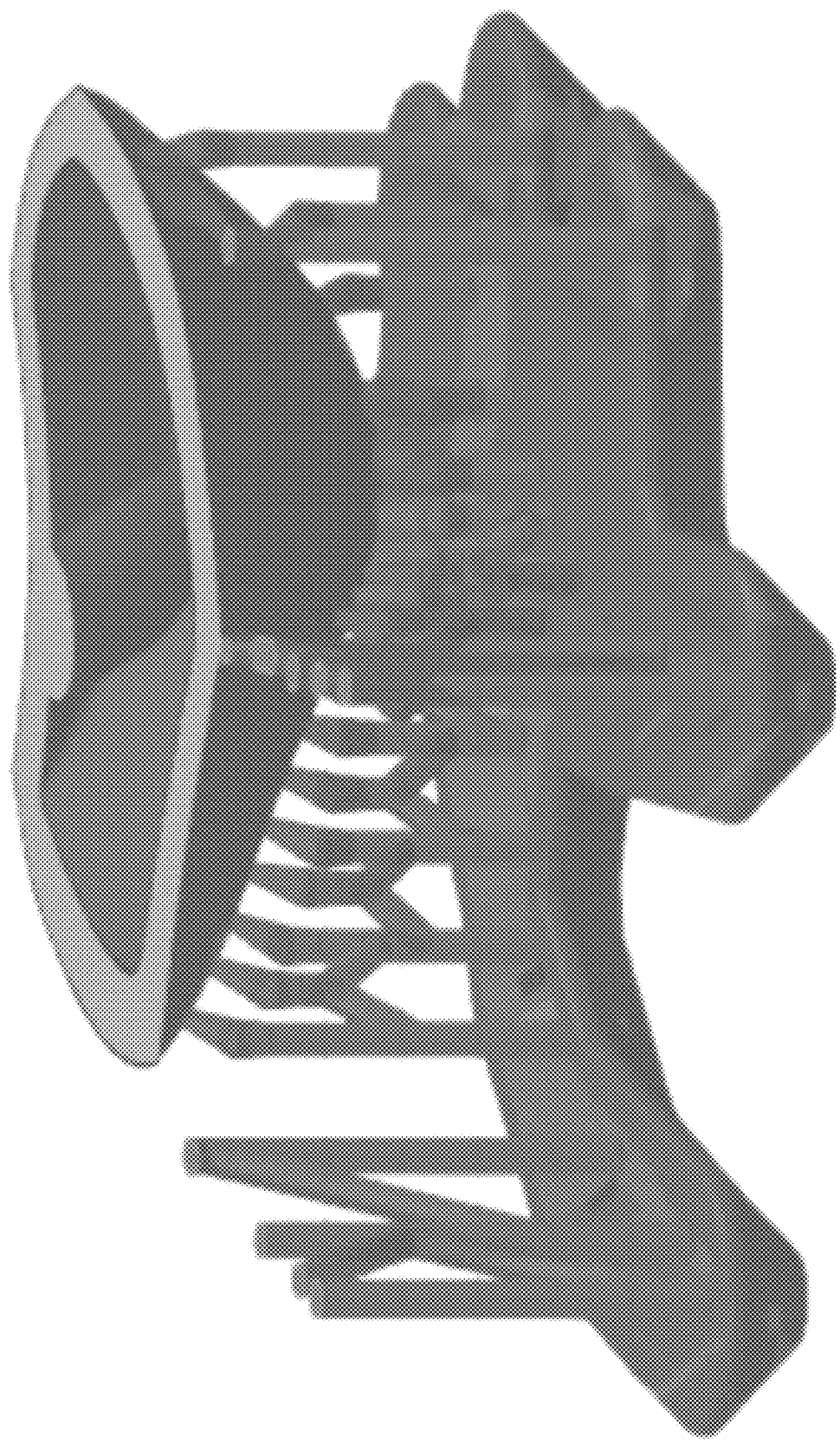
FIG. 10P – 275 slices

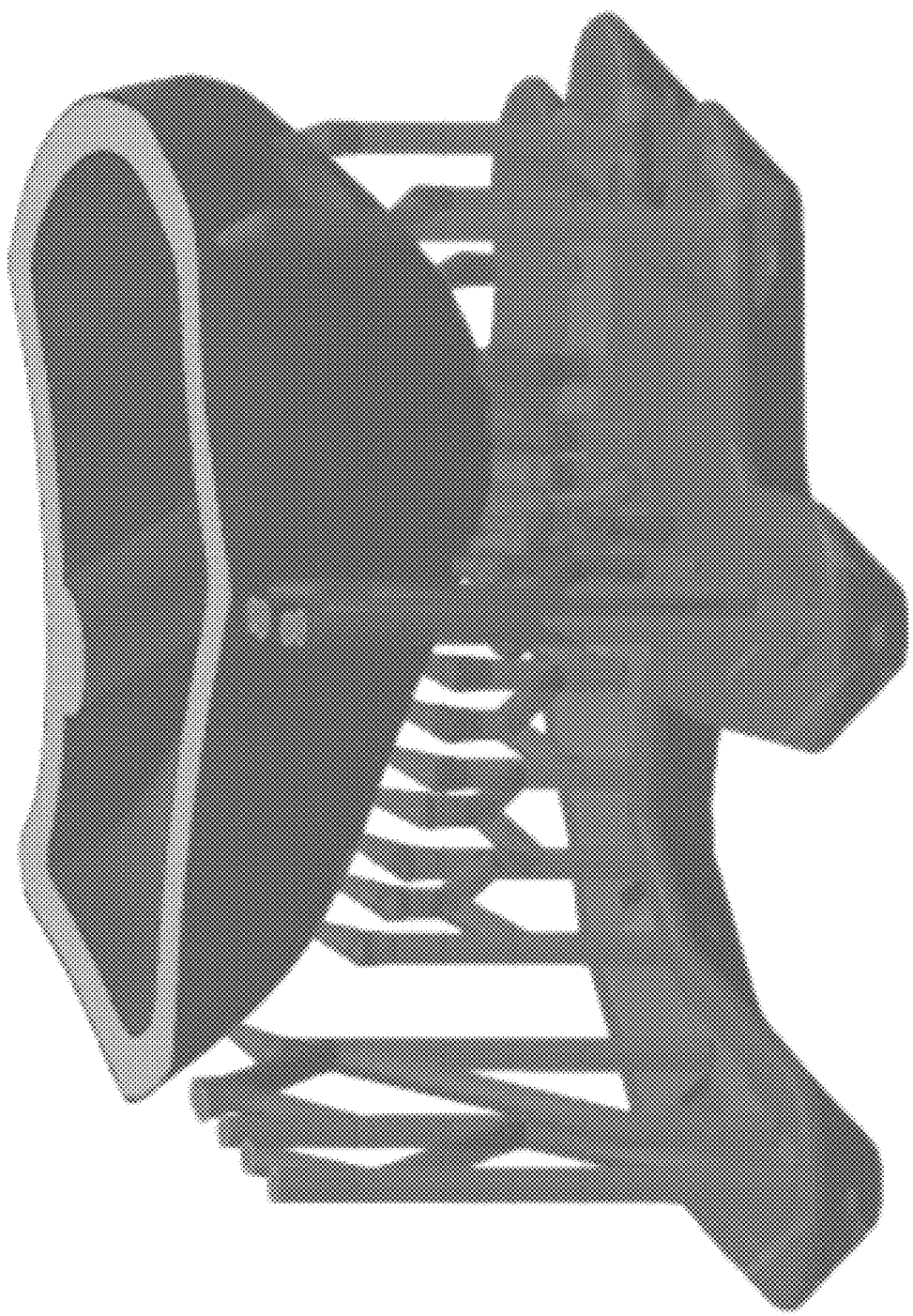
FIG. 10Q – 399 slices

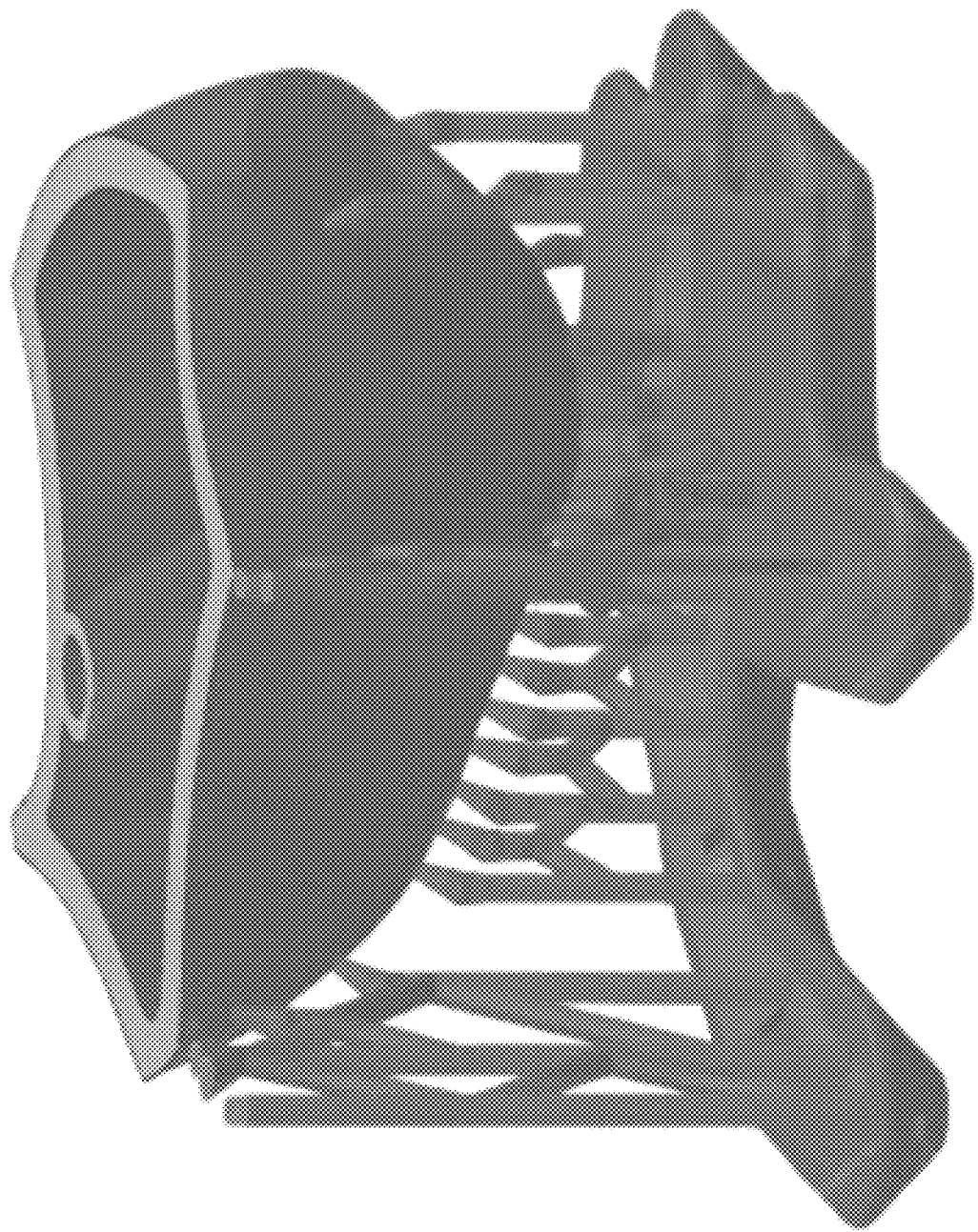
FIG. 10R – 508 slices

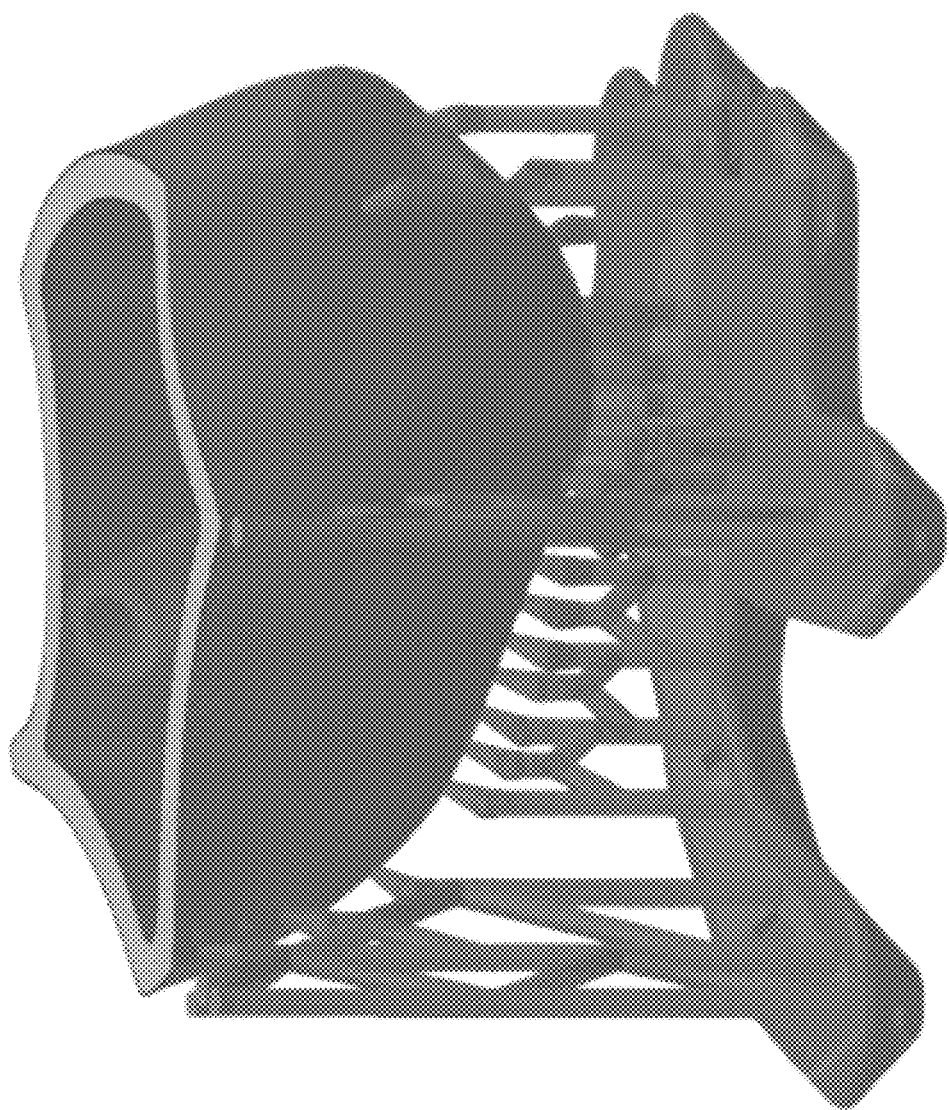
FIG. 10S – 576 slices

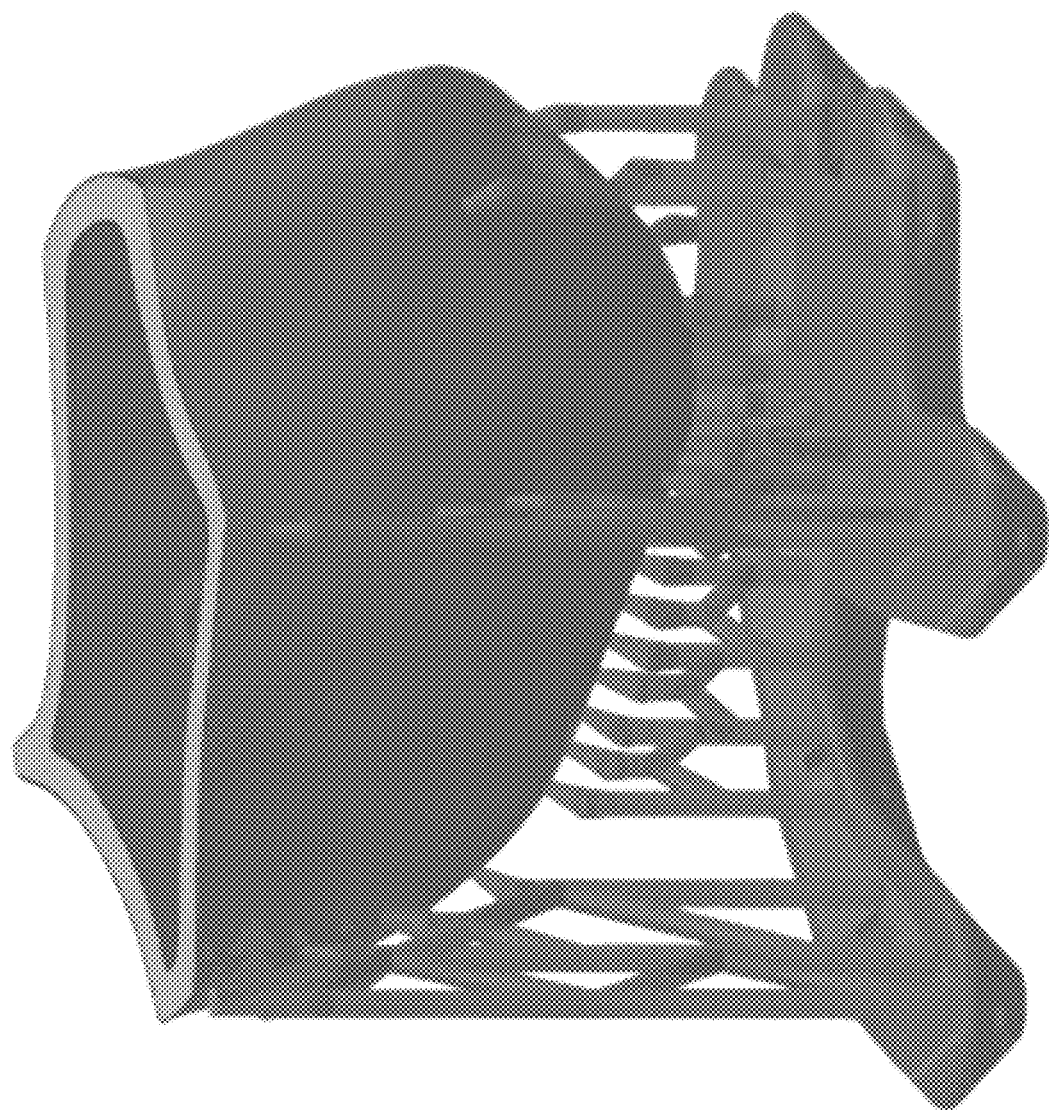
FIG. 10T – 669 slices

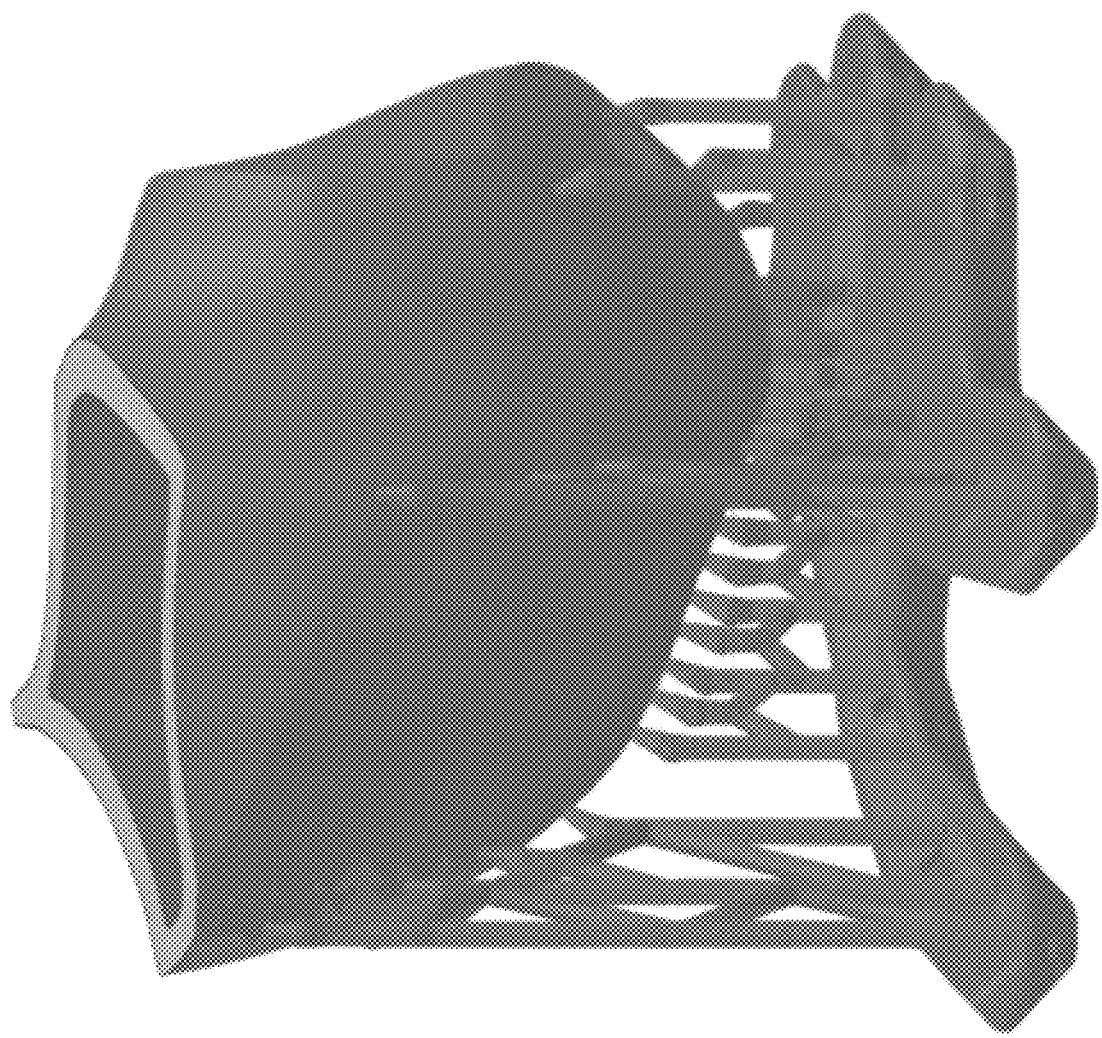
FIG. 10U – 802 slices

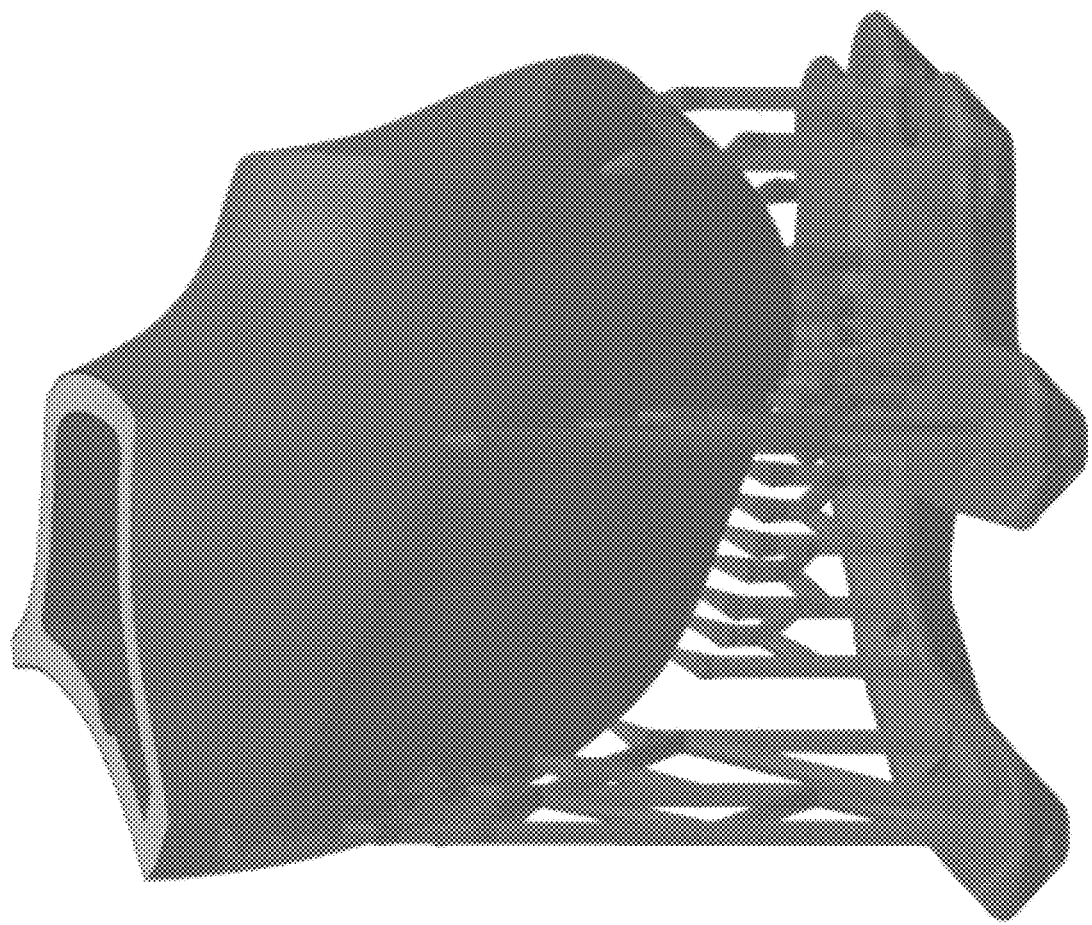
FIG. 10V – 932 slices

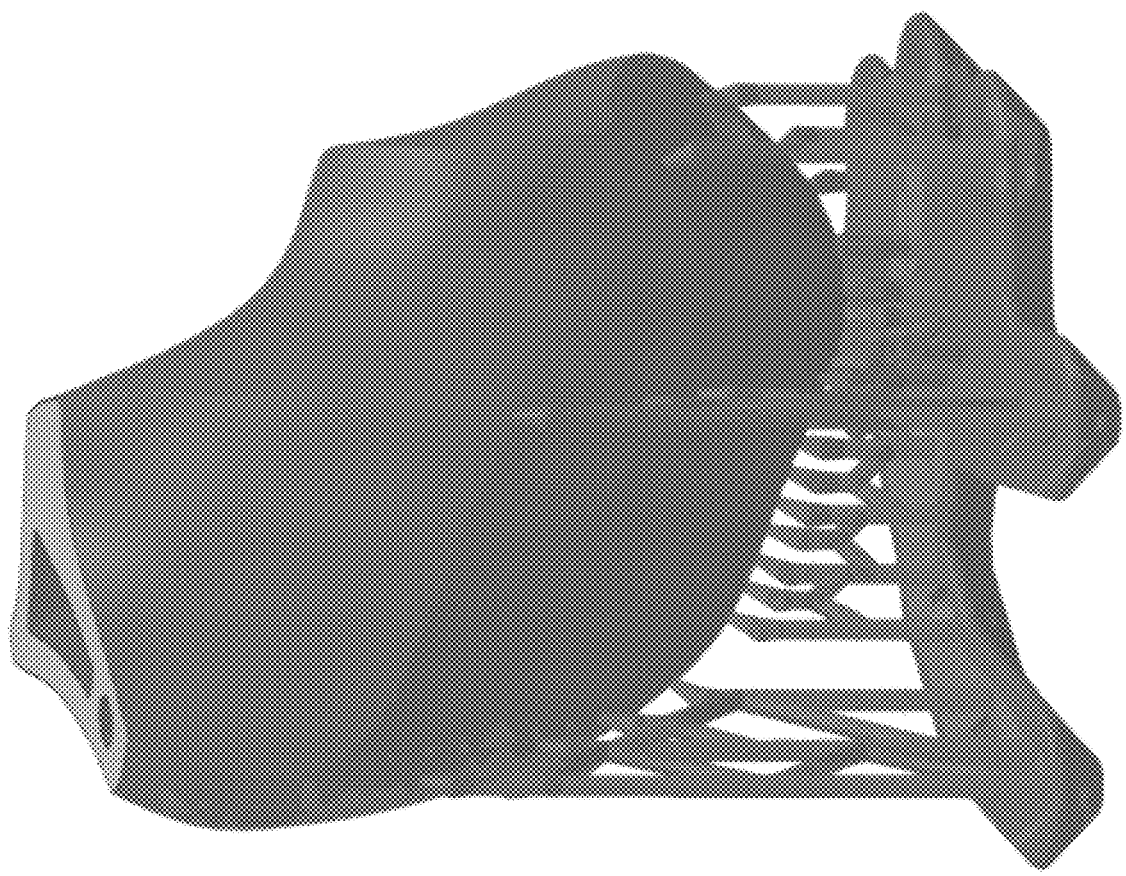
FIG. 10W – 1066 slices

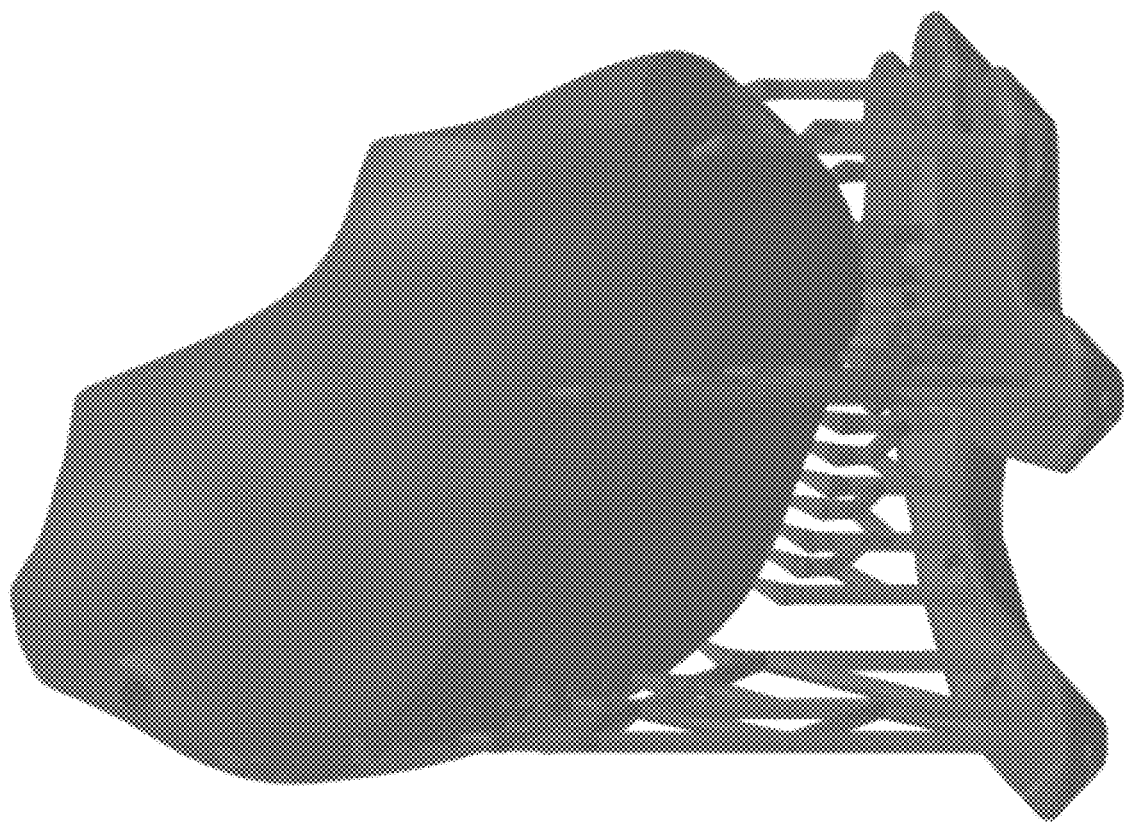
FIG. 10X – 1199 slices

HANDLE COMPOSITIONS, METHODS OF USE AND METHODS OF MAKING

CROSS-REFERENCE TO RELATED APPLICATIONS

This application is a National Stage Application, filed under 35 U.S.C. § 371, of International Application No. PCT/US2018/042314, filed Jul. 16, 2018, which claims priority to, and the benefit of U.S. Provisional Application No. 62/532,656 filed on Jul. 14, 2017, titled "Handle Compositions, Methods of Use and Methods of Making," the contents of each of which are incorporated herein by reference in their entirety.

FIELD OF THE DISCLOSURE

The disclosure is generally directed to handles or hand grips, such as those with attached instruments, compositions of matter used to make such handles, and methods of making and using the same.

BACKGROUND

There has been a long-felt but unmet need in the art for handles, such as customized handles and/or lightweight handles, which allow thought to seamlessly transition into movement. The disclosure provides such handles, and compositions and methods for producing and using such handles.

SUMMARY

The disclosure provides handles, such as those comprising one or more surfaces suitable for contacting one or more digits of a user. In some embodiments of the handles of the disclosure, the handle is radially asymmetric. In some embodiments of the handles of the disclosure, at least one of the one or more surfaces comprises a concave feature. In some embodiments of the handles of the disclosure, a volume of the handle is substantially the same as a volume of space created by the user's curved digits and a portion of the user's palm when his or her hand is relaxed.

In some embodiments of the handles of the disclosure, the one or more surfaces comprise a first surface suitable for contacting a first digit of the user and a second surface suitable for contacting a second digit of the user. In some embodiments of the handles of the disclosure, the one or more surfaces further comprise a third surface suitable for contacting a third digit of the user. In some embodiments of the handles of the disclosure, the one or more surfaces further comprise a fourth surface suitable for contacting a fourth digit of the user. In some embodiments of the handles of the disclosure, the second surface is separated from the first surface by a ridge. In some embodiments of the handles of the disclosure, the third surface is adjacent to the second surface. In some embodiments of the handles of the disclosure, the fourth surface is adjacent to the third surface. In some embodiments of the handles of the disclosure, the handle further comprises a cavity adjacent to the second surface, third surface, and fourth surface. In some embodiments of the handles of the disclosure, the cavity is separated from the first surface by the ridge. In some embodiments of the handles of the disclosure, the handle further comprises a lower surface adjacent to the ridge, the second surface, and the third surface.

The disclosure provides handles comprising a first surface suitable for contacting a first digit of a user, a second surface suitable for contacting a second digit of the user, where the second surface is separated from the first surface by a ridge, a third surface suitable for contacting a third digit of the user, where the third surface is adjacent to the second surface, a fourth surface suitable for contacting a fourth digit of the user, where the fourth surface is adjacent to the third surface, a cavity adjacent to the second surface, third surface, and fourth surface, where the cavity is separated from the first surface by the ridge, and a lower surface adjacent to the ridge, the second surface, and the third surface. In some embodiments of the handles of the disclosure, the handle is radially asymmetric. In some embodiments of the handles of the disclosure, at least one of the first surface, second surface, third surface, or fourth surface comprises a concave feature. In some embodiments of the handles of the disclosure, a volume of the handle is substantially the same as a volume of space created by the user's curved digits and a portion of the user's palm when his or her hand is relaxed.

In some embodiments of the handles of the disclosure, the portion of the user's palm comprises about 10%, 20%, 30%, 40%, 50%, 60%, 70%, 80%, or 90% of the user's palm. In some embodiments of the handles of the disclosure, the portion of the user's palm comprises about 50% of the user's palm. In some embodiments of the handles of the disclosure, the portion of the user's palm is a portion above a line between the user's thumb and pinky finger (e.g., closer to fingers than a wrist).

In some embodiments of the handles of the disclosure, the handle further comprises one or more attachment points. In some embodiments of the handles of the disclosure, at least one of the one or more attachment points is located on or within the ridge. In some embodiments of the handles of the disclosure, including those in which the handle comprises one or more attachment points, the handle comprises one or more instruments attached at the one or more attachment points. In some embodiments of the handles of the disclosure, at least one of the one or more instruments is selected from the group consisting of: a musical instrument, a surgical instrument, a cooking instrument, and a sports instrument. In some embodiments, the handle with the instrument attached comprises a musical tool, a surgical tool, a cooking tool, or a sporting equipment (including for use as a handle for one or more instruments or controls on a dashboard or interior of a luxury, sport, or racing automobile). In some embodiments of the handles of the disclosure, the instrument is a wand. In some embodiments of the handles of the disclosure, the instrument is a wand and the musical tool is a baton. In some embodiments of the handles of the disclosure, the baton is a conducting baton. In some embodiments of the handles of the disclosure, the baton comprises a balance point at or near the attachment point. In some embodiments of the handles of the disclosure, the instrument is a scalpel. In some embodiments of the handles of the disclosure, the instrument is a whisk. In some embodiments of the handles of the disclosure, the instrument is detachable.

In some embodiments of the handles of the disclosure, a thickness of the ridge at or near the attachment point is or is about 1, 1.5, 2, 2.5, 3, 3.5, 4, 4.5, 5, 5.5, 6, 6.5, 7, 7.5, 8, 8.5, 9, 9.5, 10, 15, or 20 or more times a width or diameter of the attachment point. In some embodiments of the handles of the disclosure, a thickness of the ridge at or near the attachment point is or is about 1, 1.5, 2, 2.5, 3, 3.5, or 4 times a width or diameter of the attachment point. In some embodiments of the handles of the disclosure, a thickness of the ridge at a junction of the first surface and the cavity is or is about 5, 4, 3, 2, 1, 0.75, 0.5, 0.25, or 0.1 or less times a width or diameter of the attachment point. In some embodiments of the handles of the disclosure, a thickness of the ridge at a junction of the first surface and the cavity is or is about 1, 0.75, 0.5, 0.25, or 0.1 times a width or diameter of the attachment point. In some embodiments of the handles of the disclosure, a thickness of the ridge at a junction of the first surface and the second surface, third surface, and/or fourth surface is or is about 5, 4, 3, 2, 1, 0.75, 0.5, 0.25, or 0.1 or less times a width or diameter of the attachment point. In some embodiments of the handles of the disclosure, a thickness of the ridge at a junction of the first surface and the second surface, third surface, and/or fourth surface is or is about 1, 0.75, 0.5, 0.25, or 0.1 times a width or diameter of the attachment point. In some embodiments of the handles of the disclosure, the ridge is tapered. In some embodiments of the handles of the disclosure, such as those in which the ridge comprises a taper, the taper is gradual and/or continuous.

In some embodiments of the handles of the disclosure, the volume of the handle is between or between about 1 cubic inches ($in^3$) and 8 $in^3$, inclusive of the endpoints. In some embodiments of the handles of the disclosure, the volume of the handle is between or between about 2 $in^3$ and 6 $in^3$, inclusive of the endpoints. In some embodiments of the handles of the disclosure, the volume of the handle is between or between about 2 $in^3$ and 4 $in^3$, inclusive of the endpoints. In some embodiments of the handles of the disclosure, the volume is at least or is or is about 0.5 $in^3$, 0.75 $in^3$, 1 $in^3$, 1.25 $in^3$, 1.5 $in^3$, 1.75 $in^3$, 2 $in^3$, 2.25 $in^3$, 2.5 $in^3$, 2.75 $in^3$, 3 $in^3$, 3.25 $in^3$, 3.5 $in^3$, 3.75 $in^3$, 3.8 $in^3$, 3.85 $in^3$, 3.95 $in^3$, 4 $in^3$, 4.25 $in^3$, 4.5 $in^3$, 4.75 $in^3$, 5 $in^3$, 5.25 $in^3$, 5.5 $in^3$, 6 $in^3$, 8 $in^3$, or more $in^3$. In some embodiments of the handles of the disclosure, the volume is at least or is or is about 0.5 $in^3$, 0.75 $in^3$, 1 $in^3$, 1.25 $in^3$, 1.5 $in^3$, 1.75 $in^3$, 2 $in^3$, 2.25 $in^3$, 2.5 $in^3$, 2.75 $in^3$, 3 $in^3$, 3.25 $in^3$, 3.5 $in^3$, 3.75 $in^3$, 3.8 $in^3$, 3.85 $in^3$, 3.95 $in^3$, 4 $in^3$, 4.25 $in^3$, 4.5 $in^3$, 4.75 $in^3$, 5 $in^3$, 5.25 $in^3$, 5.5 $in^3$, 6 $in^3$, 8 $in^3$, or any value in between. In some embodiments of the handles of the disclosure, the volume of the handle is or is about 4 $in^3$. In some embodiments of the handles of the disclosure, the volume of the handle is or is about 3.8 $in^3$. In some embodiments of the handles of the disclosure, the volume of the handle is or is about 3 $in^3$. In some embodiments of the handles of the disclosure, the volume is or is about 2 $in^3$. In some embodiments of the handles of the disclosure, the volume is or is about 1 $in^3$.

In some embodiments of the handles of the disclosure, one or more dimensions of a surface and/or the handle is between or between about 0.01 and 20 inches, inclusive of the endpoints, such as between or between about 0.1 and 10 inches, inclusive of the endpoints, between or between about 0.5 and 5 inches, inclusive of the endpoints, or between or between about 1 and 4 inches, inclusive of the endpoints. In some embodiments of the handles of the disclosure, at least one of the one or more dimensions comprises a height, a length, a width, a radius, a diameter, or a circumference. In some embodiments of the handles of the disclosure, the height of the handle is between or between about 0.1 and 10 inches, inclusive of the endpoints, such as between or between about 0.5 and 5 inches, inclusive of the endpoints, or between or between about 1 and 4 inches, inclusive of the endpoints. In some embodiments of the handles of the disclosure, the height of the handle is about 2.5 inches. In some embodiments of the handles of the disclosure, the length of the handle is between or between about 0.1 and 10 inches, inclusive of the endpoints, such as between or between about 0.5 and 5 inches, inclusive of the endpoints, or between or between about 1 and 3 inches, inclusive of the endpoints. In some embodiments of the handles of the disclosure, the length of the handle is about 1 inch. In some embodiments of the handles of the disclosure, the width of the handle is between or between about 0.1 and 10 inches, inclusive of the endpoints, such as between or between about 0.5 and 5 inches, inclusive of the endpoints, or between or between about 1 and 3 inches, inclusive of the endpoints. In some embodiments of the handles of the disclosure, the width of the handle is about 1.5 inches. In some embodiments of the handles of the disclosure, the height of the handle is about 2.5 inches, the length of the handle is about 1 inches, and the width of the handle is about 1.5 inches.

In some embodiments of the handles of the disclosure, the first digit is a thumb, index finger, middle finger, ring finger, or pinky finger. In some embodiments of the handles of the disclosure, the second digit is a thumb, index finger, middle finger, ring finger, or pinky finger. In some embodiments of the handles of the disclosure, the third digit is a thumb, index finger, middle finger, ring finger, or pithy finger. In some embodiments of the handles of the disclosure, the fourth digit is a thumb, index finger, middle finger, ring finger, or pinky finger. In some embodiments of the handles of the disclosure, the first digit is a thumb. In some embodiments of the handles of the disclosure, the second digit is an index finger. In some embodiments of the handles of the disclosure, the third digit is a middle finger. In some embodiments of the handles of the disclosure, the fourth digit is a ring finger.

In some embodiments of the handles of the disclosure, a mass of the handle is between or between about 1 and 50 grams, inclusive of the endpoints. In some embodiments of the handles of the disclosure, a mass of the handle is between or between about 10 and 30 grams, inclusive of the endpoints. In some embodiments of the handles of the disclosure, a mass of the handle is between or between about 15 and 25 grams, inclusive of the endpoints. In some embodiments of the handles of the disclosure, a mass of the handle is between or between about 1 and 50 grams, inclusive of the endpoints. In some embodiments of the handles of the disclosure, a mass of the handle is about 20 grams. In some embodiments of the handles of the disclosure, a mass of the handle is about 20.4 grams.

In some embodiments of the handles of the disclosure, the mass of the handle is between or between about 1 and 500 grams, 1 and 450 grams, 1 and 400 grams, 1 and 350 grams, 1 and 300 grams, 1 and 250 grams, 1 and 200 grams, 1 and 175 grams, 1 and 150 grams, 1 and 140 grams, 1 and 130 grams, 1 and 120 grams, 1 and 110 grams, 1 and 100 grams, 1 and 90 grams, 1 and 80 grams, 1 and 70 grams, 1 and 60 grams, 1 and 50 grams, 1 and 40 grams, 1 and 30 grams, 1 and 20 grams 1 and 10 grams, or 1 and 5 grams, inclusive of all values and ranges therebetween. In some embodiments of the handles of the disclosure, the mass of the handle is greater than or greater than about 1 gram, 2 grams, 3 grams, 4 grams, 5 grams, 6 grams, 7 grams, 8 grams, 9 grams, 10 grams, 15 grams, 20 grams, 25 grams, 30 grams, 35 grams, 40 grams, 45 grams, 50 grams, 55 grams, 60 grams, 70 grams, 75 grams, 80 grams, 85 grams, 90 grams, 95 grams, 100 grams, 105 grams, 110 grams, 115 grams, 120 grams, 125 grams, 130 grams, 135 grams, 140 grams, 145 grams, 150 grams, 160 grams, 170 grams, 180 grams, 190 grams, 200 grams, 210 grams, 220 grams, 230 grams, 240 grams, 250 grams, 300 grams, 350 grams, 400 grams, 450 grams, or 500 grams, inclusive of all values and ranges therebetween. In some embodiments of the handles of the disclosure, the mass of the handle is less than or less than about 500 grams, 450 grams, 400 grams, 350 grams, 300 grams, 250 grams, 240 grams, 230 grams, 220 grams, 210 grams, 200 grams, 195 grams, 190 grams, 185 grams, 180 grams, 175 grams, 170 grams, 165 grams, 160 grams, 155 grams, 150 grams, 145 grams, 140 grams, 135 grams, 130 grams, 125 grams, 120 grams, 115 grams, 110 grams, 105 grams, 100 grams, 95 grams, 90 grams, 85 grams, 80 grams, 75 grams, 70 grams, 65 grams, 60 grams, 55 grams, 50 grams, 45 grams, 40 grams, 35 grams, 30 grams, 25 grams, 20 grams, 15 grams, 10 grams, 9 grams, 8 grams, 7 grams, 6 grams, 5 grams, 4 grams, 3 grams, 2 grams, or 1 gram, inclusive of all values and ranges therebetween.

In some embodiments of the handles of the disclosure, a mass of the handle with the one or more instruments attached is between or between about 1 and 500 grams, inclusive of the endpoints. In some embodiments of the handles of the disclosure, a mass of the handle with the one or more instruments attached is between or between about 10 and 30 grams, inclusive of the endpoints. In some embodiments of the handles of the disclosure, a mass of the handle with the one or more instruments attached is between or between about 15 and 25 grams, inclusive of the endpoints. In some embodiments of the handles of the disclosure, a mass of the handle with the one or more instruments attached is between or between about 1 and 50 grams, inclusive of the endpoints. In some embodiments of the handles of the disclosure, a mass of the handle with the one or more instruments attached is about 20 grams. In some embodiments of the handles of the disclosure, a mass of the handle is about 22.5 grams.

In some embodiments of the handles of the disclosure, a mass of the handle with the one or more instruments attached is between or between about 1 and 500 grams, 1 and 450 grams, 1 and 400 grams, 1 and 350 grams, 1 and 300 grams, 1 and 250 grams, 1 and 200 grams, 1 and 175 grams, 1 and 150 grams, 1 and 140 grams, 1 and 130 grams, 1 and 120 grams, 1 and 110 grams, 1 and 100 grams, 1 and 90 grams, 1 and 80 grams, 1 and 70 grams, 1 and 60 grams, 1 and 50 grams, 1 and 40 grams, 1 and 30 grams, 1 and 20 grams 1 and 10 grams, or 1 and 5 grams, inclusive of all values and ranges therebetween. In some embodiments of the handles of the disclosure, the mass of the handle with the one or more instruments attached is greater than or greater than about 1 gram, 2 grams, 3 grams, 4 grams, 5 grams, 6 grams, 7 grams, 8 grams, 9 grams, 10 grams, 15 grams, 20 grams, 25 grams, 30 grams, 35 grams, 40 grams, 45 grams, 50 grams, 55 grams, 60 grams, 70 grams, 75 grams, 80 grams, 85 grams, 90 grams, 95 grams, 100 grams, 105 grams, 110 grams, 115 grams, 120 grams, 125 grams, 130 grams, 135 grams, 140 grams, 145 grams, 150 grams, 160 grams, 170 grams, 180 grams, 190 grams, 200 grams, 210 grams, 220 grams, 230 grams, 240 grams, 250 grams, 300 grams, 350 grams, 400 grams, 450 grams, or 500 grams, inclusive of all values and ranges therebetween. In some embodiments of the handles of the disclosure, the mass of the handle with the one or more instruments attached is less than or less than about 500 grams, 450 grams, 400 grams, 350 grams, 300 grams, 250 grams, 240 grams, 230 grams, 220 grams, 210 grams, 200 grams, 195 grams, 190 grams, 185 grams, 180 grams, 175 grams, 170 grams, 165 grams, 160 grams, 155 grams, 150 grams, 145 grams, 140 grams, 135 grams, 130 grams, 125 grams, 120 grams, 115 grams, 110 grams, 105 grams, 100 grams, 95 grams, 90 grams, 85 grams, 80 grams, 75 grams, 70 grams, 65 grams, 60 grams, 55 grams, 50 grams, 45 grams, 40 grams, 35 grams, 30 grams, 25 grams, 20 grams, 15 grams, 10 grams, 9 grams, 8 grams, 7 grams, 6 grams, 5 grams, 4 grams, 3 grams, 2 grams, or 1 gram, inclusive of all values and ranges therebetween.

In some embodiments of the handles of the disclosure, at least one of the first surface and the second surface comprise a concave feature. In some embodiments of the handles of the disclosure, the first surface and the second surface each comprises a concave feature. In some embodiments of the handles of the disclosure, at least two of the first surface, the second surface, and the third surface comprise a concave feature. In some embodiments of the handles of the disclosure, at least two of the first surface, the second surface, the third surface, and the fourth surface comprise a concave feature. In some embodiments of the handles of the disclosure, at least two of the first surface, the second surface, the third surface, the fourth surface, the cavity, and the lower surface comprise a concave feature. In some embodiments of the handles of the disclosure, at least three of the first surface, the second surface, the third surface, the fourth surface, the cavity, and the lower surface comprise a concave feature. In some embodiments of the handles of the disclosure, at least four of the first surface, the second surface, the third surface, the fourth surface, the cavity, and the lower surface comprise a concave feature. In some embodiments of the handles of the disclosure, at least five of the first surface, the second surface, the third surface, the fourth surface, the cavity, and the lower surface comprise a concave feature. In some embodiments of the handles of the disclosure, the first surface, the second surface, the third surface, the fourth surface, the cavity, and the lower surface each comprises a concave feature.

In some embodiments of the handles of the disclosure, the first surface and the second surface each comprises a convex feature. In some embodiments of the handles of the disclosure, at least two of the first surface, the second surface, and the third surface comprise a convex feature. In some embodiments of the handles of the disclosure, at least two of the first surface, the second surface, the third surface, and the fourth surface comprise a convex feature. In some embodiments of the handles of the disclosure, at least two of the first surface, the second surface, the third surface, the fourth surface, the cavity, and the lower surface comprise a convex feature. In some embodiments of the handles of the disclosure, at least three of the first surface, the second surface, the third surface, the fourth surface, the cavity, and the lower surface comprise a convex feature. In some embodiments of the handles of the disclosure, at least four of the first surface, the second surface, the third surface, the fourth surface, the cavity, and the lower surface comprise a convex feature. In some embodiments of the handles of the disclosure, at least five of the first surface, the second surface, the third surface, the fourth surface, the cavity, and the lower surface comprise a convex feature. In some embodiments of the handles of the disclosure, the first surface, second surface, third surface, fourth surface, cavity, and lower surface each comprises a convex feature.

In some embodiments of the handles of the disclosure, one or more of the first surface, the second surface, the third surface, the fourth surface, the lower surface, the ridge, or the cavity comprises both a concave feature and a convex feature. In some embodiments of the handles of the disclosure, two or more of the first surface, the second surface, the third surface, the fourth surface, the lower surface, the ridge, or the cavity comprises both a concave feature and a convex feature. In some embodiments of the handles of the disclosure, three or more of the first surface, the second surface, the third surface, the fourth surface, the lower surface, the ridge, or the cavity comprises both a concave feature and a convex feature. In some embodiments of the handles of the disclosure, four or more of the first surface, the second surface, the third surface, the fourth surface, the lower surface, the ridge, or the cavity comprises both a concave feature and a convex feature. In some embodiments of the handles of the disclosure, five or more of the first surface, the second surface, the third surface, the fourth surface, the lower surface, the ridge, or the cavity comprises both a concave feature and a convex feature. In some embodiments of the handles of the disclosure, six or more of the first surface, the second surface, the third surface, the fourth surface, the lower surface, the ridge, or the cavity comprises both a concave feature and a convex feature.

In some embodiments of the handles of the disclosure, one or more of a dimension, a mass, or the volume is customized to accommodate the user's hand. In some embodiments of the handles of the disclosure, customizing one or more of a dimension such as length, width, height, or another such dimension, the mass of the handle, or the volume of the handle can result in a handle that substantially conforms to the user's hand such that when the user grips the handle for a duration of use of the apparatus, less, substantially less, no, or substantially no ergonomic issues arise relative to a similar apparatus having a conventional handle. In some embodiments of the handles of the disclosure, the ergonomic design of the handle can result in a reduction in the compressive force necessary to grip, lift, hold aloft, move, rotate, operate, spin, implement, invert, reciprocate, or otherwise operably engage the apparatus to which the handle is coupled. In some embodiments of the handles of the disclosure, the handle can have a plurality of contact surfaces configured to directly abut or substantially abut a plurality of gripping surfaces of the user's hand. In some embodiments, the compressive force necessary to operably engage the handle can be between about 0.01 N and about 5 N, about 0.1 N and about 4 N, about 0.2 N and about 3.5 N, about 0.3 N and about 3 N, about 0.4 N and about 2.5 N, about 0.5 N and about 2 N, about 0.6 N and about 1.5 N, or about 0.7 N and about 1 N, inclusive of all values and ranges therebetween. In some embodiments, a first gripping surface of the plurality of gripping surface can be positioned and oriented such that the gravitation force applied by the Earth on the handle is countered by additional force from the first gripping surface, whereas a lesser force is applied from a second gripping surface of the plurality of gripping surfaces, the second gripping surface being positioned and oriented differently than the first gripping surface. In other words, one or more fingers of the user's hand can be used to hold the apparatus aloft while a lesser force can be applied by a different one or more fingers of the user's hand to stabilize the apparatus in space. During use of the apparatus, the handle may change position and orientation dynamically, therefore more or less force can be applied to each of the plurality of contact surfaces by each of the corresponding plurality of gripping surfaces of the user's hand during use of the apparatus. In some embodiments of the handles of the disclosure, the force, finger position, inner volume of the user's hand occupied by the handle, frictional coefficients of contact surfaces of the handle, balance point of the apparatus, required grip strength (force applied by fingers/hand to engage handle), and other characteristics of the handle can be optimized. In some embodiments of the handles of the disclosure, such characteristics can be optimized by customizing the shape, volume, materials use, manufacturing method, dimensions, and other characteristics of the handle. In some embodiments of the handles of the disclosure, optimizing these characteristics by engineering a more ergonomic handle that is substantially customized for the user's hand and/or use scenario may lead to a reduction in related stresses on musculature and tendons of a user's arm corresponding to the user's hand, reducing incidence of repetitive use injuries and the like.

In some embodiments of the handles of the disclosure, the handle comprises smooth edges. In some embodiments of the handles of the disclosure, the handle comprises rough edges. In some embodiments of the handles of the disclosure, the handle comprises a mixture of rough edges and smooth edges. In some embodiments of the handles of the disclosure, the handle comprises a textured surface. In some embodiments of the handles of the disclosure, the handle comprises a surface having an inherent texture based upon the material or materials from which the handle is formed. In some embodiments of the handles of the disclosure, a texture or texturing member can be applied to the handle in order to confer texture to the finished handle. In some embodiments of the handles of the disclosure, material from the surface of the handle can be removed, e.g., by etching, to form a textured surface on the handle. In some embodiments of the handles of the disclosure. In some embodiments of the handles of the disclosure, the handle is partially or substantially hollow. In some embodiments of the handles of the disclosure, the handle is painted and/or lacquered.

With reference to FIGS. 6 through 9, the disclosure provides handles comprising a first surface 101 suitable for contacting a first digit of a user; a second surface 108 suitable for contacting a second digit of the user, where the second surface 108 is separated from the first surface 101 by a ridge 102; a third surface 109 suitable for contacting a third digit of the user, where the third surface 109 is adjacent to the second surface 108; a fourth surface 110 suitable for contacting a fourth digit, where the fourth surface 110 is adjacent to the third surface 109; a cavity 104 adjacent to the first surface 101, second surface 108, third surface 109, and fourth surface 110, where the cavity 104 is separated from the first surface 101 by the ridge 102; a lower surface 103 adjacent to the ridge 102, the second surface 108, and the third surface 109; and an attachment point 106 on or within the ridge 102, where a wand 105 is attached to the handle at the attachment point 106. In some embodiments of the handles of the disclosure, the handle 100 is radially asymmetric. In some embodiments of the handles of the disclosure, at least one of the first surface 101, second surface 108, third surface 109, fourth surface 110, lower surface 103, and cavity 104 comprises a concave feature. In some embodiments of the handles of the disclosure, the volume of the handle 100 is substantially the same as a volume of a space between a user's palm and digits when his or her hand is relaxed.

In some embodiments of the handles of the disclosure, the wand has a mass of between or between about 1 and 5 grams, inclusive of the endpoints, such as between or between about 2 and 3 grams, inclusive of the endpoints. In some embodiments of the handles of the disclosure, the wand has a mass of about 2.5 grams. In some embodiments of the handles of the disclosure, the length of the wand is approximately the length of the distance between the user's hand and elbow. In some embodiments of the handles of the disclosure, the wand is between or between about 5 and 15 inches long, inclusive of the endpoints. In some embodiments of the handles of the disclosure, the wand is or is about 12 inches long. In some embodiments of the handles of the disclosure, the wand is or is about 6 inches long. In some embodiments of the handles of the disclosure, the wand comprises glass fiber. In some embodiments of the handles of the disclosure, the wand comprises carbon fiber. In some embodiments of the handles of the disclosure, the wand is tapered. In some embodiments, the wand is white. In some embodiments of the handles of the disclosure, the wand is tapered. In some embodiments, the wand has been painted white.

In some embodiments of the handles of the disclosure, the handle comprises a resin, a hardener, and a filler.

In some embodiments of the handles of the disclosure, the resin is selected from the group consisting of an epoxy resin, a vinyl ester resin, a liquid plastic casting resin (e.g., Smooth-On FEATHER LITE), polyurethane, silicone, acrylic, and polyester. In some embodiments of the handles of the disclosure, the resin comprises an epoxy resin. In some embodiments of the handles of the disclosure, the resin comprises a 30-minute epoxy resin. In some embodiments of the handles of the disclosure, the epoxy resin is selected from the group consisting of an alkylene oxide, an alkenyl oxide, a glycidyl ester, an epoxy novolac, a copolymer of acrylic acid, an ester of glycidol, a copolymerizable vinyl compound, polyurethane, a polyurethane polyepoxide, and mixtures thereof. In some embodiments of the handles of the disclosure, the resin comprises a vinyl ester resin (e.g., Fibre Glast® 1100 Vinyl Ester Resin, low viscosity).

In some embodiments of the handles of the disclosure, the hardener is selected from the group consisting of an epoxy hardener, a phenalkamine, an aromatic amine, a modified amine, an aliphatic amine, a modified aliphatic amine, a cycloaliphatic amine, an imidazole, a polymercaptan agent, liquid polymercaptan, a polysulfide resin, a phenolic agent, an anhydride, a latent curing agent, a boron trifluoride-amine complex, a dicyandiamide, an organic acid hydrazide, a waterborne agent, a polyamine, a modified polyamine, a photo-curing agent, an ultraviolet-curing agent, and mixtures thereof. In some embodiments of the handles of the disclosure, the hardener comprises an epoxy hardener. In some embodiments of the handles of the disclosure, the hardener comprises a 30-minute epoxy hardener. In some embodiments of the handles of the disclosure, the hardener comprises a vinyl ester hardener.

In some embodiments of the handles of the disclosure, the filler is selected from the group consisting of glass microspheres, micro-glass balls, micro-glass beads, silica, glass fabric, fiberglass fabric (e.g., Fibre Glast® 241-F Fiberglass fabric), carbon fiber fabric, Kevlar, installation foam (e.g., Loctite® Tite Foam Insulating Foam; Home Depot), polyurethane, nanoparticles, nanofibers, nanometal, micro-fibers, epoxy, wood, cork, carbon nanotubes, graphene, ceramic, cellulose, woven polyester, non-woven polyester, woven glass, non-woven glass, glass frit, ceramic frit, metal woven screen, metal non-woven screen, silk protein, spider silica, carbon fibers, glass, fiberglass, plastic, inorganic particles, inorganic microspheres, hollow inorganic microspheres, zirconia, ivory, vegetal ivory, kaolin, rubber, silver, iron, steel, latex, thermally foaming powder, and elastic fibers. In some embodiments of the handles of the disclosure, filler comprises glass microspheres. In some embodiments of the handles of the disclosure, the filler is a resin, a hardener, or a mixture of both, such as any of those described herein. In some embodiments of the handles of the disclosure, filler comprises glass fabric. In some embodiments of the handles of the disclosure, the glass fabric is about 18 g/m3. In some embodiments of the handles of the disclosure, the glass fabric comprises a weave pattern of between or between about 30° and 60°, inclusive of the endpoints. In some embodiments of the handles of the disclosure, the glass fabric comprises a weave pattern of about 45°. In some embodiments of the handles of the disclosure, the handle has a lower density as compared to a handle that does not comprise the filler, or that comprises less of the filler or a different type of filler. In some embodiments of the handles of the disclosure, the handle has a lower mass as compared to a handle that does not comprise the filler, or that comprises less of the filler or a different type of filler.

In some embodiments of the handles of the disclosure, the resin comprises about 40% of the handle. In some embodiments of the handles of the disclosure, the handle comprises between or between about 10 and 20 grams of resin, inclusive of the endpoints. In some embodiments of the handles of the disclosure, the handle comprises about 15 grams of resin. In some embodiments of the handles of the disclosure, the hardener comprises about 40% of the handle. In some embodiments of the handles of the disclosure, the handle comprises between or between about 10 and 20 grams of hardener, inclusive of the endpoints. In some embodiments of the handles of the disclosure, the handle comprises about 15 grams of hardener. In some embodiments of the handles of the disclosure, the filler comprises about 20% of the handle. In some embodiments of the handles of the disclosure, the handle comprises between or between about 5 and 10 grams of filler, inclusive of the endpoints. In some embodiments of the handles of the disclosure, the handle comprises about 7.5 grams of filler. In some embodiments of the handles of the disclosure, the handle comprises about 15 grams of epoxy resin, about 15 grams of epoxy hardener, and about 7.5 grams of glass microspheres. In some embodiments of the handles of the disclosure, the ratio of resin to hardener is between or between about 1:1 and 50:1, inclusive of the endpoints, such as between or between about 2:1, 10:1, 25:1, or 50:1. In some embodiments of the handles of the disclosure, the ratio of resin to hardener is or is about 1:1. In some embodiments of the handles of the disclosure, the ratio of resin to hardener is or is about 49:1.

In some embodiments of the handles of the disclosure, the handle contacts the user's digits and/or hand at one or more acupressure points associated with a body part selected from the group consisting of the head, brain, ears, eyes, sinuses, chest, lungs, stomach, spinal column, and heart. In some embodiments of the handles of the disclosure, the handle contacts the user's digits and/or hand at acupressure points associated with the head and brain, ears, and eyes. In some embodiments of the handles of the disclosure, the handle contacts the user's thumb at an acupressure point associated with the head and brain. In some embodiments of the handles of the disclosure, the handle contacts the user's index finger and/or middle finger at an acupressure point associated with the eyes. In some embodiments of the handles of the disclosure, the handle contacts the user's ring finger and/or pinky finger at an acupressure point associated with the ears. Without wishing to be bound by any particular theory, the contact between an acupressure point or acupressure points of a user's finger or fingers and one or more points of the handle can lead to reduced ergonomic stress on the musculature, tendons, soft tissues, bones, skin, and other biological materials of the user's hand and arm used to operably engage the handle.

In some embodiments of the handles of the disclosure, the user is an adult human. In some embodiments of the handles of the disclosure, the user is a human child. In some embodiments of the handles of the disclosure, the user is a well-known conductor.

In some embodiments of the handles of the disclosure, the handle is suitable for contacting the right hand of the user. In some embodiments of the handles of the disclosure, the handle is suitable for contacting the left hand of the user.

The disclosure provides methods of manufacturing a mold, such as those comprising mixing a resin with a hardener and a filler to produce an imprint mixture. In some embodiments of the methods of the disclosure, the method of manufacturing a mold comprises kneading the imprint mixture to remove air bubbles. In some embodiments of the methods of the disclosure, the method of manufacturing a mold comprises taking an imprint of a model user's hand by having the model user grasp and/or squeeze the imprint mixture, thereby producing an imprint model comprising one or more surfaces suitable for contacting one or more digits of a user. In some embodiments of the methods of the disclosure, the imprint model is radially asymmetric. In some embodiments of the methods of the disclosure, at least one of the one or more surfaces comprises a concave feature. In some embodiments of the methods of the disclosure, a volume of the imprint model is substantially the same as a volume of space created by the user's curved digits and a portion of the user's palm when his or her hand is relaxed. In some embodiments of the methods of the disclosure, the method of manufacturing a mold comprises incubating the imprint model. In some embodiments of the methods of the disclosure, the method of manufacturing a mold comprises carving, sanding, and/or polishing the imprint model. In some embodiments of the methods of the disclosure, the method of manufacturing a mold comprises submerging a first portion of the imprint model in a first liquid bath. In some embodiments of the methods of the disclosure, the method of manufacturing a mold comprises allowing the first liquid bath to become solid, thereby producing a first portion of the mold. In some embodiments of the methods of the disclosure, the method of manufacturing a mold comprises submerging a second portion of the imprint model in a second liquid bath. In some embodiments of the methods of the disclosure, the method of manufacturing a mold comprises allowing the second liquid bath to become solid, thereby producing a second portion of the mold. In some embodiments of the methods of the disclosure, the first portion of the mold and the second portion of the mold together constitute the mold.

In some embodiments of the methods of the disclosure, the method of manufacturing a mold further comprises inserting one or more instruments into the imprint model. In some embodiments of the methods of the disclosure, at least one of the one or more instruments is selected from the group consisting of: a musical instrument, a surgical instrument, a cooking instrument, a teaching instrument, a mechanical instrument, an entertainment instrument, an electrical device, a gaming device, a presentation tool, an analytical device, a laboratory instrument, a cutting instrument, a weapon, an artistic instrument, and a sports instrument. In some embodiments of the methods of the disclosure, the instrument is a wand. In some embodiments of the methods of the disclosure, the instrument is a scalpel. In some embodiments of the methods of the disclosure, the instrument is a whisk. In some embodiments of the methods of the disclosure, the instrument is a wireless slide changing tool that can be configured to remotely communicate with a computer processor. In some embodiments of the methods of the disclosure, the instrument is a laser pointer. In some embodiments of the methods of the disclosure, the instrument is a pointer for indicating to an object, for example by a teacher during instruction of a class. In some embodiments of the methods of the disclosure, the instrument is a conductor's baton. In some embodiments of the methods of the disclosure, the instrument is a controller configured to wirelessly operate a toy. In some embodiments of the methods of the disclosure, the instrument is a controlled configured to wireless communicate a user's instructions to a game consol. In some embodiments of the methods of the disclosure, the instrument is a screwdriver. In some embodiments of the methods of the disclosure, the instrument is a chef's knife. In some embodiments of the methods of the disclosure, the instrument is a spatula. In some embodiments of the methods of the disclosure, the instrument is a probe or sensor for use in field experiments or a laboratory. In some embodiments of the methods of the disclosure, the instrument is a painter's brush. In some embodiments of the methods of the disclosure, the instrument is a weapon with a cutting edge such as a saber, rapier, katana, or the like.

In some embodiments of the methods of the disclosure, including those methods of making a mold, the first liquid bath and/or second liquid bath comprises liquid silicone.

In some embodiments of the methods of the disclosure, including those methods of making a mold, the first portion of the imprint model and second portion of the imprint model are not the same. In some embodiments of the methods of the disclosure, the first portion of the imprint model and second portion of the imprint model each comprises about 50% of the imprint model.

In some embodiments of the methods of the disclosure, including those methods of making a mold, the model user is an adult human. In some embodiments of the methods of the disclosure, the model user is a human child. In some embodiments of the methods of the disclosure, the model user is a well-known conductor.

The disclosure provides methods of manufacturing handles, such as any of those described herein. In some embodiments of the methods of the disclosure, the method of manufacturing the handle comprises a) mixing a resin with a hardener and a filler to produce an initial mixture; b) adding the initial mixture into a mold; c) incubating the initial mixture to produce a solid mixture; d) removing the solid mixture from the mold; e) carving, sanding, and/or polishing the solid mixture to produce a sanded handle; and f) painting and/or lacquering the sanded handle, thereby producing the handle.

The disclosure provides methods of manufacturing handles, such as any of those described herein. In some embodiments of the methods of the disclosure, the method comprises a) mixing a resin with a hardener and a filler to produce an initial mixture; b) adding the initial mixture into two or more portions of a mold; c) incubating the initial mixture to produce two or more fractions; d) removing the two or more fractions from the two or more portions of a mold; e) combining the two or more fractions to produce a solid mixture; f) carving, sanding, and/or polishing the solid mixture to produce a sanded handle; and g) painting and/or lacquering the sanded handle, thereby producing the handle.

In some embodiments of the methods of the disclosure, the mold and/or two or more portions of the mold comprise silicone. In some embodiments of the methods of the disclosure, the mold and/or the two or more portions of the mold are produced by any of the methods of manufacturing a mold described herein. In some embodiments of the methods of the disclosure, the two or more portions of the mold comprise two portions of the mold. In some embodiments of the methods of the disclosure, such as those in which the two or more portions of a mold comprise two portions of the mold, the two portions of the mold each comprise about 50% of the mold.

In some embodiments of the methods of the disclosure, the incubating is carried out at between or between about 20° and 25° C., inclusive of the endpoints. In some embodiments of the methods of the disclosure, the incubating is carried out at about 23° C. In some embodiments of the methods of the disclosure, the incubating is carried out at about room temperature. In some embodiments of the methods of the disclosure, the incubating is carried out for between or between about 5 minutes and 24 hours, inclusive of the endpoints. In some embodiments of the methods of the disclosure, the incubating is carried out for between or between about 30 and 60 minutes, inclusive of the endpoints. In some embodiments of the methods of the disclosure, the adding step comprises injecting the initial mixture into the mold or two or more portions of the mold.

In some embodiments of the methods of the disclosure, the method further comprises (e.g., between steps d) and e)), carving out an inner portion of one or more of the two or more fractions. In some embodiments of the methods of the disclosure, the carving out reduces the mass of at least one of the two or more fractions. In some embodiments of the methods of the disclosure, the two or more fractions comprise a void and/or are partially or substantially hollow. In some embodiments of the methods of the disclosure, the handle comprises a void and/or is partially or substantially hollow.

In some embodiments of the methods of the disclosure, the method further comprises prior to incubating, inserting one or more instruments into the mold or at least one of the two or more portions of the mold.

In some embodiments of the methods of the disclosure, the method further comprises affixing one or more instruments, such as those described herein, to one or more attachment points of the handle.

In some embodiments of the methods of the disclosure, at least one of the one or more instruments is selected from the group consisting of: a musical instrument, a surgical instrument, a cooking instrument, and a sports instrument. In some embodiments of the methods of the disclosure, the one or more instruments is or comprises a wand. In some embodiments of the methods of the disclosure, the one or more instruments is or comprises a wand, and the handle with the wand attached constitutes a baton. In some embodiments of the methods of the disclosure, the one or more instruments is or comprises a scalpel. In some embodiments of the methods of the disclosure, the one or more instruments is or comprises a whisk.

In some embodiments of the methods of the disclosure, the affixing comprises attaching the instrument to the handle using a first adhesive substance. In some embodiments of the methods of the disclosure, the combining comprises attaching the two or more fractions together with a second adhesive substance. In some embodiments of the methods of the disclosure, the first adhesive substance and second adhesive substance are the same. In some embodiments of the methods of the disclosure, the first adhesive substance and/or second adhesive substance comprises one or more adhesives selected from the group consisting of glue, epoxy resin, epoxy hardener, tape, cement, mucilage, or paste. In some embodiments of the methods of the disclosure, the affixing comprises attaching the instrument to the handle with a first fastener. In some embodiments of the methods of the disclosure, the combining comprises attaching the two or more fractions together with a second fastener. In some embodiments of the methods of the disclosure, the first fastener and second fastener are the same. In some embodiments of the methods of the disclosure, the first fastener and/or second fastener is selected from the group consisting of a nail, a screw, and a staple.

In some embodiments of the methods of the disclosure, the method further comprises kneading the initial mixture until smooth and/or to expel air bubbles.

In some embodiments of the methods of the disclosure, at least three of the steps are performed by hand.

In some embodiments of the methods of the disclosure, at least three of the steps are performed using high-throughput manufacturing methods. In some embodiments of the methods of the disclosure, the method comprises using a high-throughput manufacturing method. In some embodiments of the methods of the disclosure, the high-throughput method comprises 3D printing, 4D printing, stamping, and/or injection molding.

In some embodiments of the methods of the disclosure, the high-throughput method comprises 3D and/or 4D printing. In some embodiments of the methods of the disclosure, the handle is 3D printed and/or 4D printed to comprise a void and/or is partially or substantially hollow. In some embodiments of the methods of the disclosure, the high-throughput method comprises injection molding. In some embodiments of the methods of the disclosure, the handle can be entirely produced using the high-throughput method comprising 3D and/or 4D printing.

In some embodiments of the methods of the disclosure, the high-throughput method can comprise a 3D scanning and printing method, such as that described in U.S. Pat. No. 9,649,814, the entire disclosure of which is hereby incorporated herein by reference. For instance, in some embodiments of the methods of the disclosure, the high-throughput method can comprise. In some embodiments of the methods of the disclosure, the high-throughput method can be carried out using a 3D scanning and printing apparatus comprising: an imaging platform for carrying an object; a processor electrically connected with the imaging platform; an optical reflector electrically connected with the processor, wherein the processor controls the optical reflector to move between a first position and a second position; a projector electrically connected with the processor, wherein when the optical reflector is located at the first position, the projector projects a structured light to the object so as to produce 3D spatial information, and the processor receives the 3D spatial information and produces 3D printing information; and a 3D printer electrically connected with the processor, wherein when the optical reflector is located at the second position, the projector projects a cutting layer image according to the 3D printing information, and the optical reflector reflects the cutting layer image to the 3D printer, and the 3D printer prints a 3D printing copy based on the cutting layer image. In some embodiments of the methods of the disclosure, the high-throughput method can be carried out by a) mixing a resin with a hardener and a filler to produce an initial mixture; b) adding the initial mixture into a mold; c) incubating the initial mixture to produce a solid mixture; d) removing the solid mixture from the mold; e) carving, sanding, and/or polishing the solid mixture to produce a sanded handle; f) creating a plurality of digital images of the sanded handle using a computer-readable media; g) causing the computer-readable media to generate a three-dimensional image based upon the plurality of digital images of the sanded handle; h) causing the computer-readable media to calculate dimensional information about the three-dimensional image, the dimensional information configured to be read by a 3D printing apparatus; and i) causing the printing apparatus to receive the dimensional information and generate a 3D printed object.

In some embodiments of the methods of the disclosure, the high-throughput method can be accomplished using a bottom-up method by which a device such as a 3D printer or the like begins depositing printing material at a base or onto a substrate and deposits material in slices moving upward relative to the base or substrate. In some embodiments of the methods of the disclosure, the high-throughput method can be accomplished using a top-down method by which a device such as a 3D printer or the like begins depositing printing material onto a ceiling or top inner surface of an enclosure, and then deposits material in slices moving downward relative to the ceiling or top inner surface of the enclosure. In some embodiments of the methods of the disclosure, the handle or apparatus can be printed or otherwise manufactured by depositing between about 20 and about 10,000 slices of material onto the substrate and/or previously deposited material. In some embodiments of the methods of the disclosure, the handle or apparatus can be supported during printing by first or concurrently printing a support post or a plurality of support posts that are deposited onto the base, the substrate, the ceiling, or the top inner surface of the printing enclosure and is then printed to connect to the handle or apparatus to provide stability during printing. In some embodiments of the methods of the disclosure, the support post or plurality of support posts can be dimensioned and configured to attach to the outside of the handle or the apparatus without altering the finished handle or apparatus aesthetically or functionally. In some embodiments of the methods of the disclosure, the support post or plurality of support posts can be dimensioned and configured to be removed after the handle or the apparatus has been fully printed using the high-throughput method. An example of a bottom-up method for printing a handle according to a high-throughput method using support posts and slices of material deposited iteratively to form the finished handle is illustrated in FIG. 10.

In some embodiments of the methods of the disclosure, the apparatus or handle can be printed with a cavity or a plurality of cavities defined within the handle. In some embodiments of the methods of the disclosure, the cavity or the plurality of cavities within the handle can be defined by a hand-carving process or by a casting process in a mold. In some embodiments of the methods of the disclosure, the cavity or the plurality of cavities within the handle can be defined during the high-throughput method, e.g., during 3D printing. In some embodiments of the methods of the disclosure, the handle can comprise a cavity that has a volume that is greater than about 10 vol % of the total volume of the handle, greater than about 20 vol %, greater than about 30 vol %, greater than about 40 vol %, greater than about 50 vol %, greater than about 60 vol %, greater than about 70 vol %, greater than about 80 vol %, or greater than about 90 vol %, inclusive of all values and ranges therebetween. In some embodiments of the methods of the disclosure, the handle can comprise a cavity such that the density of the handle is reduced, as compared to a handle having no cavity formed therein, by greater than about 10%, 20%, 30%, 40%, 50%, 60%, 70%, 80%, 90%, or greater, inclusive of all values and ranges therebetween. An example of a bottom-up method for printing a handle according to a high-throughput method using support posts and slices of material deposited iteratively to form the finished handle is illustrated in FIG. 10.

According to the methods of the disclosure, including the 3D printing shown in FIG. 10, the handle can comprise a first cavity having a purpose of light-weighting the handle and a second cavity smaller than the first cavity and having a purpose of receiving a portion of a component of the apparatus, such as a wand for a baton or a blade for a scalpel, or the like. The light-weighting or shaping of a cavity of the interior of the handle may provide superior balance of the apparatus once the handle is united with a component of the apparatus, such as a wand for a baton or a blade for a scalpel, or the like. For example, when the apparatus is a conducting baton, the handle may be shaped internally to have a cavity and externally to fit a user's hand such that, upon receiving a wand, the balance point of the apparatus (the conducting baton having a wand and a handle), resides at the connection point of the wand and the handle or to shift the balance point to any specific location along the apparatus desired by either the maker or the user.

In some embodiments of the methods of the disclosure, the high-throughput method can comprise: forming a mold of an inner cavity of a user's hand using a curable material; trimming the mold of the inner cavity of the user's hand to desired dimensions of a handle as described herein; and printing a 3D copy of the mold of the inner cavity of the user's hand using a 3D imaging and printing device, the 3D imaging and printing device comprising: an imaging platform for carrying an object; a processor electrically connected with the imaging platform; an optical reflector electrically connected with the processor, wherein the processor controls the optical reflector to move between a first position and a second position; a projector electrically connected with the processor, wherein when the optical reflector is located at the first position, the projector projects a structured light to the object so as to produce 3D spatial information, and the processor receives the 3D spatial information and produces 3D printing information; and a 3D printer electrically connected with the processor, wherein when the optical reflector is located at the second position, the projector projects a cutting layer image according to the 3D printing information, and the optical reflector reflects the cutting layer image to the 3D printer, and the 3D printer prints a 3D printing copy based on the cutting layer image. In some embodiments of the methods of the disclosure, the optical reflector comprises a plane mirror. In some embodiments of the methods of the disclosure, the 3D imaging and printing device further comprises: an image camera receiving the 3D spatial information and transmitting the 3D spatial information to the processor. In some embodiments of the methods of the disclosure, the 3D imaging and printing device further comprises: a shaping chamber and a printing material disposed in the shaping chamber, wherein the optical reflector reflects the cutting layer image to the printing material. In some embodiments of the methods of the disclosure, the 3D imaging and printing device further comprises: a motor, a thread rod and a shaping plate, the processor drives the motor to active the thread rod, and then the thread rod moves the shaping plate. In some embodiments of the methods of the disclosure, the 3D spatial information comprises depth information of the object. In some embodiments of the methods of the disclosure, the processor controls the platform to rotate within a plurality of specific angles. In some embodiments of the methods of the disclosure, the 3D imaging and printing device further comprises: a track, wherein the optical reflector is disposed on the track to move between the first position and the second position. In some embodiments of the methods of the disclosure, the image camera is a CCD camera. In some embodiments of the methods of the disclosure, the printing material comprises a light cured material.

In some embodiments of the methods of the disclosure, an instrument is manufactured simultaneously with the handle. In some embodiments of the methods of the disclosure, the handle and the instrument are manufactured as a single unit. In some embodiments of the methods of the disclosure, the handle and the instrument are manufactured simultaneously and coupled together after being formed. In some embodiments of the methods of the disclosure, the handle and the instrument are manufactured simultaneously and from a single material such that the finished instrument or substantially finished apparatus is manufactured in a single manufacturing process (e.g., using a 3D printer). In some embodiments, the finished or substantially finished apparatus can be further processed to include a protective coating (such as a stain, paint, or the like). In some embodiments, the 3D printed model of the handle can be designed or engineered to have a dimension or dimensions that are smaller than the desired dimension or dimensions of the finished handle such that once the coating or other materials are added to the surface of the 3D printed handle, the coated handle then has a dimension or dimensions equal to or substantially equal to the desired dimension or dimensions of the finished handle.

In some embodiments of the methods of the disclosure, the resin is selected from the group consisting of an epoxy resin, a vinyl ester resin, a liquid plastic casting (e.g., Smooth-On FEATHER LITE), polyurethane, silicone, acrylic, and polyester. In some embodiments of the methods of the disclosure, the resin comprises an epoxy resin. In some embodiments of the methods of the disclosure, the resin comprises a 30-minute epoxy resin. In some embodiments of the methods of the disclosure, the epoxy resin is selected from the group consisting of an alkylene oxide, an alkenyl oxide, a glycidyl ester, an epoxy novolac, a copolymer of acrylic acid, an ester of glycidol, a copolymerizable vinyl compound, polyurethane, a polyurethane polyepoxide, and mixtures thereof. In some embodiments of the methods of the disclosure, the resin comprises a vinyl ester resin (e.g., Fibre Glast® 1100 Vinyl Ester Resin, low viscosity).

In some embodiments of the methods of the disclosure, the hardener is selected from the group consisting of an epoxy hardener, a phenalkamine, an aromatic amine, a modified amine, an aliphatic amine, a modified aliphatic amine, a cycloaliphatic amine, an imidazole, a polymercaptan agent, liquid polymercaptan, a polysulfide resin, a phenolic agent, an anhydride, a latent curing agent, a boron trifluoride-amine complex, a dicyandiamide, an organic acid hydrazide, a waterborne agent, a polyamine, a modified polyamine, a photo-curing agent, an ultraviolet-curing agent, and mixtures thereof. In some embodiments of the methods of the disclosure, the hardener comprises an epoxy hardener. In some embodiments of the methods of the disclosure, the hardener comprises a 30-minute epoxy hardener. In some embodiments of the methods of the disclosure, the hardener comprises a vinyl ester hardener.

In some embodiments of the methods of the disclosure, the filler is selected from the group consisting of glass microspheres, micro-glass balls, micro-glass beads, silica, glass fabric, fiberglass fabric (e.g., Fibre Glast® 241-F Fiberglass fabric), carbon fiber fabric, Kevlar, installation foam (e.g., Loctite® Tite Foam Insulating Foam. Home Depot), polyurethane, a liquid plastic casting (e.g., Smooth-On FEATHER LITE), nanoparticles, nanofibers, nanometal, micro-fibers, epoxy, wood, cork, carbon nanotubes, graphene, ceramic, cellulose, woven polyester, non-woven polyester, woven glass, non-woven glass, glass frit, ceramic frit, metal woven screen, metal non-woven screen, silk protein, spider silica, carbon fibers, glass, fiberglass, plastic, inorganic particles, inorganic microspheres, hollow inorganic microspheres, zirconia, ivory, vegetal ivory, kaolin, rubber, silver, iron, steel, latex, thermally foaming powder, and elastic fibers. In some embodiments of the methods of the disclosure, the filler comprises glass microspheres. In some embodiments of the handles of the disclosure, the filler is a resin, a hardener, or a mixture of both, such as any of those described herein. In some embodiments of the methods of the disclosure, the filler comprises glass fabric. In some embodiments of the methods of the disclosure, the glass fabric is about 18 g/m$^3$. In some embodiments of the methods of the disclosure, the glass fabric comprises a weave pattern of between or between about 30° and 60°, inclusive of the endpoints. In some embodiments of the methods of the disclosure, the glass fabric comprises a weave pattern of about 45°. In some embodiments of the methods of the disclosure, the handle has a lower density as compared to a handle manufactured to not comprise the filler, or to comprise less of the filler or a different type of filler. In some embodiments of the methods of the disclosure, the handle has a lower mass as compared to a handle manufactured to not comprise the filler, or to comprise less of the filler or a different type of filler.

In some embodiments of the methods of the disclosure, the resin comprises about 40% of the imprint mixture and/or initial mixture. In some embodiments of the methods of the disclosure, the imprint mixture and/or initial mixture comprises between or between about 10 and 20 grams of resin, inclusive of the endpoints. In some embodiments of the methods of the disclosure, the imprint mixture and/or initial mixture comprises about 15 grams of resin. In some embodiments of the methods of the disclosure, the hardener comprises about 40% of the imprint mixture and/or initial mixture. In some embodiments of the methods of the disclosure, the imprint mixture and/or initial mixture comprises between or between about 10 and 20 grams of hardener, inclusive of the endpoints. In some embodiments of the methods of the disclosure, the imprint mixture and/or initial mixture comprises about 15 grams of hardener. In some embodiments of the methods of the disclosure, the filler comprises about 20% of the imprint mixture and/or initial mixture. In some embodiments of the methods of the disclosure, the imprint mixture and/or initial mixture comprises between or between about 5 and 10 grams of filler, inclusive of the endpoints. In some embodiments of the methods of the disclosure, the imprint mixture and/or initial mixture comprises about 7.5 grams of filler. In some embodiments of the methods of the disclosure, the mixing comprises mixing about 15 grams of epoxy resin with about 15 grams of epoxy hardener and about 7.5 grams of glass microspheres. In some embodiments of the methods of the disclosure, the ratio of resin to hardener is between or between about 1:1 and 50:1, inclusive of the endpoints. In some embodiments of the methods of the disclosure, the ratio of resin to hardener is or is about 1:1. In some embodiments of the methods of the disclosure, the ratio of resin to hardener is or is about 49:1.

In some embodiments of the methods of the disclosure, the method further comprises heating the solid mixture after the carving, sanding, and/or polishing step. In some embodiments of the methods of the disclosure, the heating is performed at between or between about 115° and 125° F., inclusive of the endpoints. In some embodiments of the methods of the disclosure, the heating is performed at about 120° F. In some embodiments of the methods of the disclosure, the heating is performed for between or between about 30 minutes and 24 hours, inclusive of the endpoints. In some embodiments of the methods of the disclosure, the heating is performed for about 60 minutes. In some embodiments of the methods of the disclosure, the heating is performed for about 12 hours. In some embodiments of the methods of the disclosure, the heating is performed in an oven.

In some embodiments of the methods of the disclosure, the method further comprises customizing one or more of a dimension, a mass, and/or the volume of the imprint mixture, initial mixture, solid mixture, sanded handle, or handle to accommodate the model user's or user's hand. In some embodiments of the methods of the disclosure, the model user and the user are the same. In some embodiments of the methods of the disclosure, the method is customized to manufacture a handle suitable for contacting the user's right hand. In some embodiments of the methods of the disclosure, the method is customized to manufacture a handle suitable for contacting the user's left hand.

The disclosure provides molds produced by any of the methods disclosed herein.

The disclosure provides handles produced by any of the methods disclosed herein.

The disclosure provides batons, e.g., conducting batons, comprising any of the handles disclosed herein.

The disclosure provides batons, e.g., conducting batons, produced by any of the methods disclosed herein.

BRIEF DESCRIPTION OF THE DRAWINGS

FIG. 10A-X are a series of views depicting aggregated slices of a right-handed handle of the disclosure for 3D printing using formlabs' PreForm™ software. While the program allows for a smooth transition from slice to slice in a viewer from any angle, building from the top or from the bottom of the handle, selected and aggregated slices are shown in this Figure to provide interior views of the handle, and specifically, a first cavity of the handle. The views depict not only the outer surface of the handle but a first inner cavity, the volume of which may be adjusted for light-weighting and adjusting balance of an apparatus containing the handle once united with a component of the apparatus (e.g. a wand for making a conducting baton). The same process may be followed for making a left-handed handle or apparatus containing same.

DETAILED DESCRIPTION

Figure 1A:
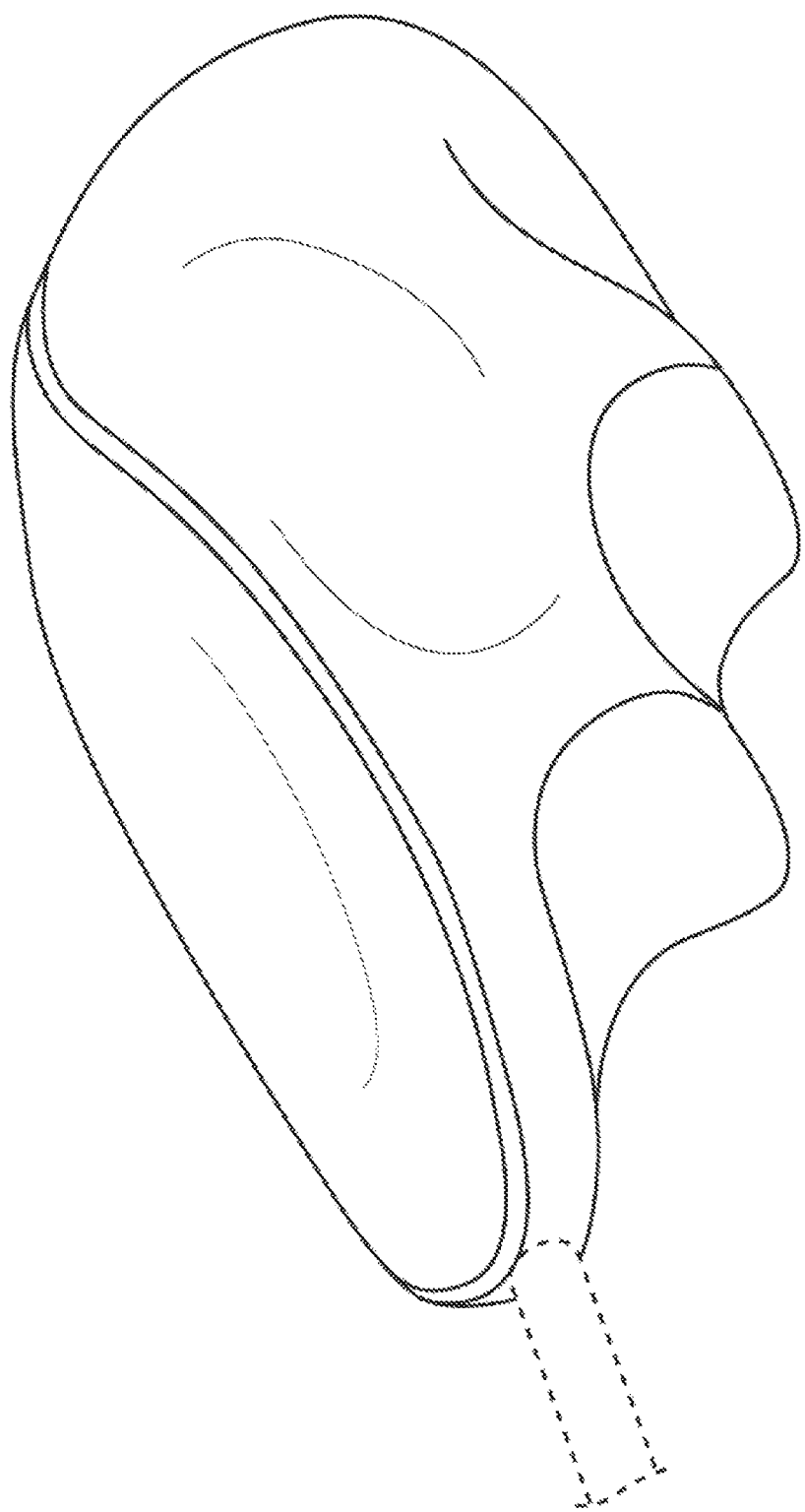
FIG. 1A is a perspective view of Side 1 of a handle, according to an embodiment.
Figure 1B:
FIG. 1B is a perspective view of Side 2 of the handle of FIG. 1A.
Figure 1C:
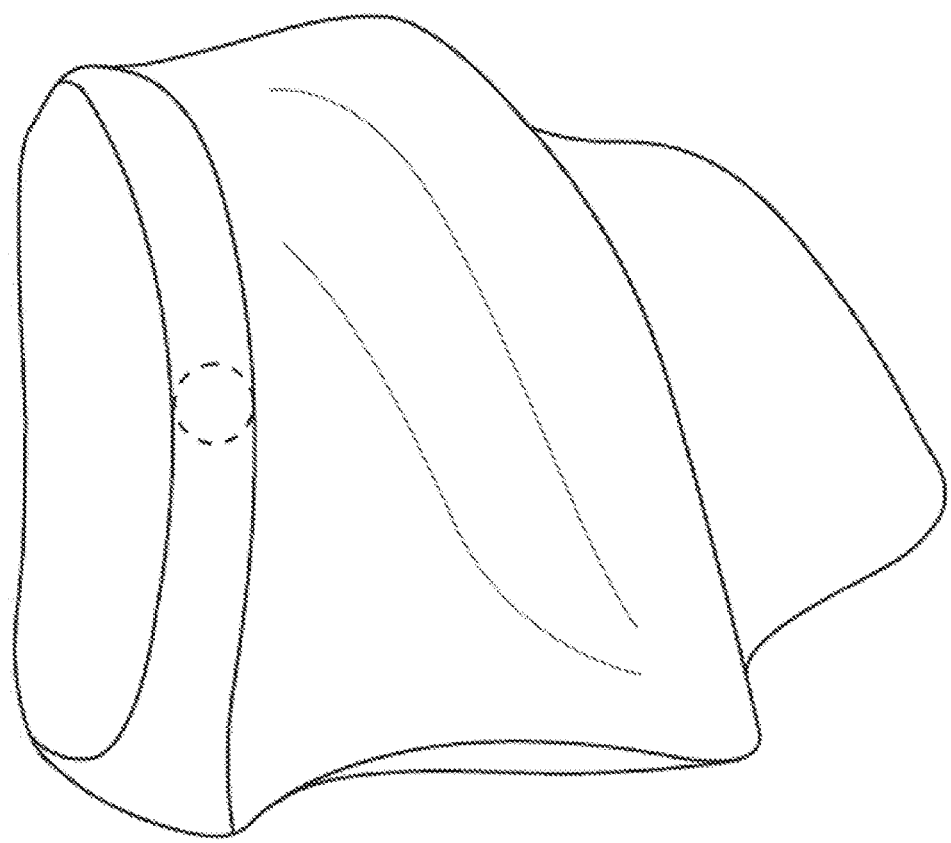
FIG. 1C is a top view of the handle of FIG. 1A.
Figure 1D:
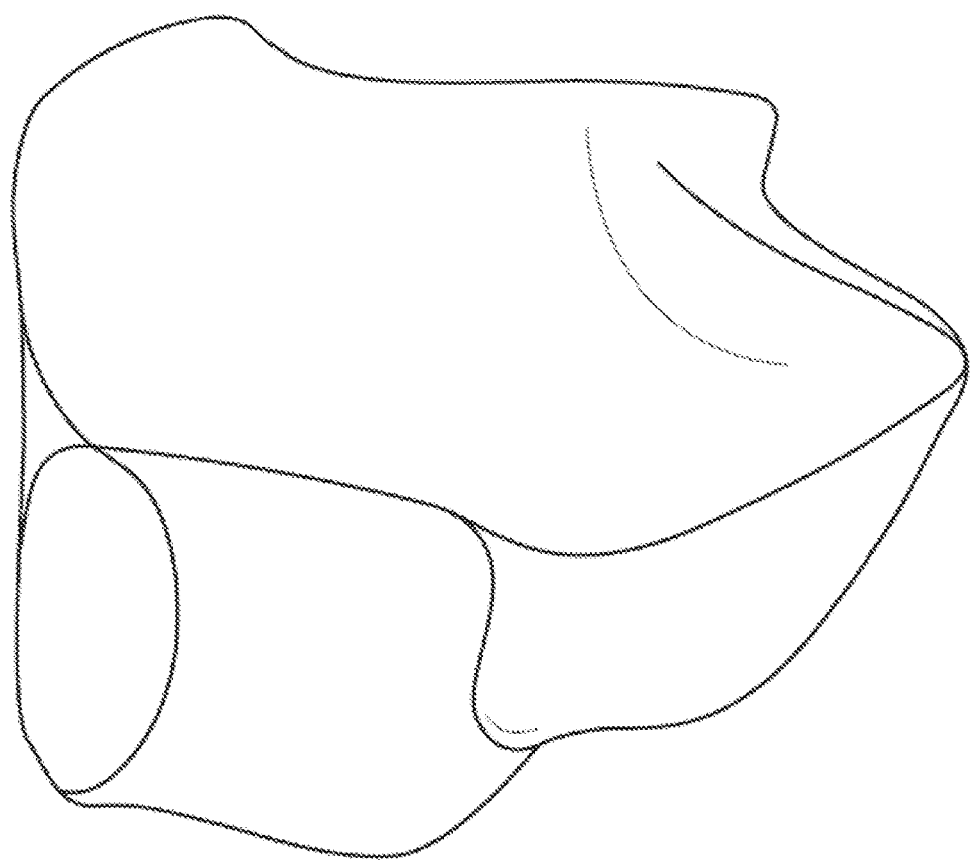
FIG. 1D is a bottom view of the handle of FIG. 1A.
Figure 1E:
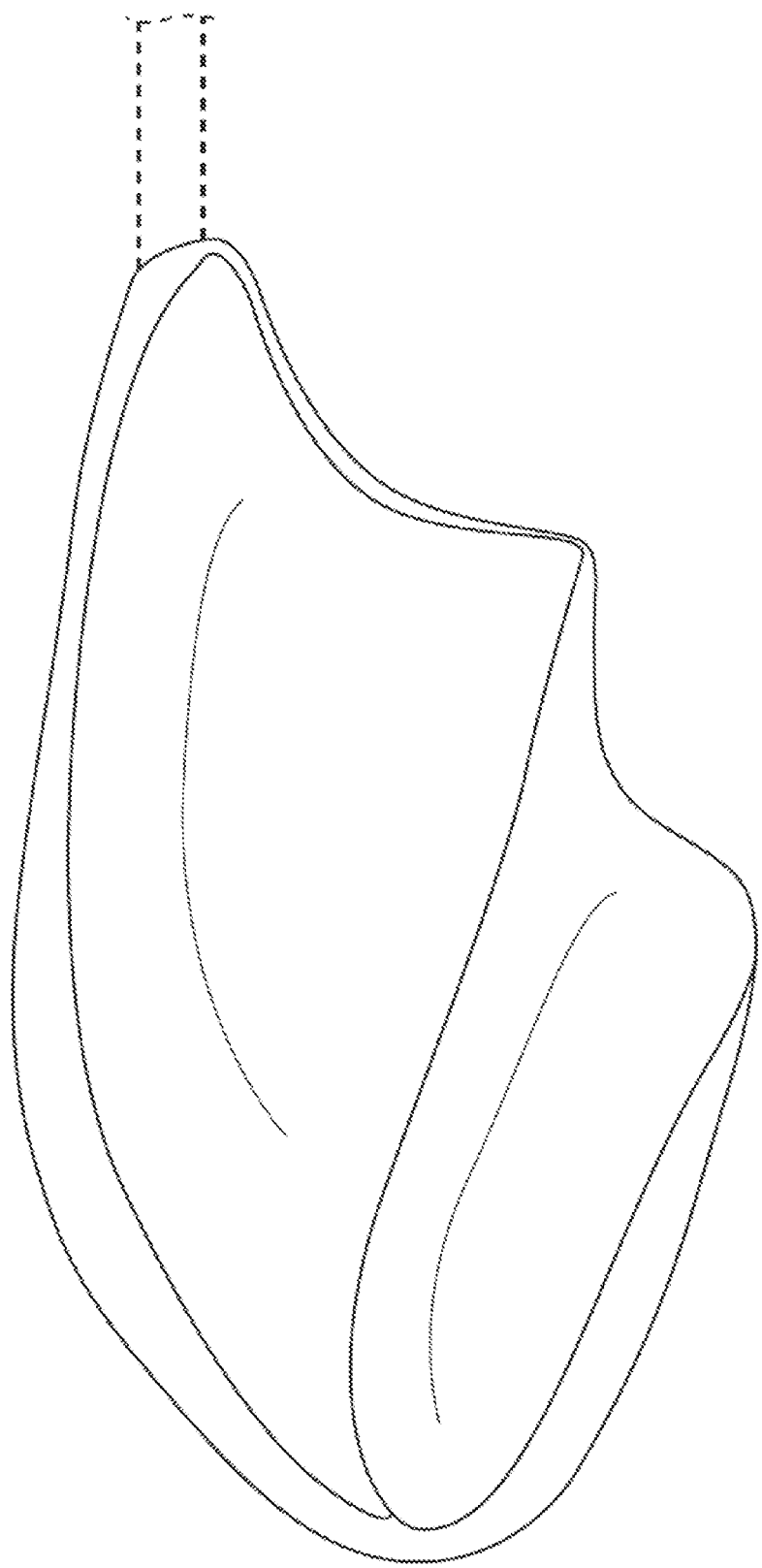
FIG. 1E is a Side 2 view of the handle of FIG. 1A.
Figure 1F:
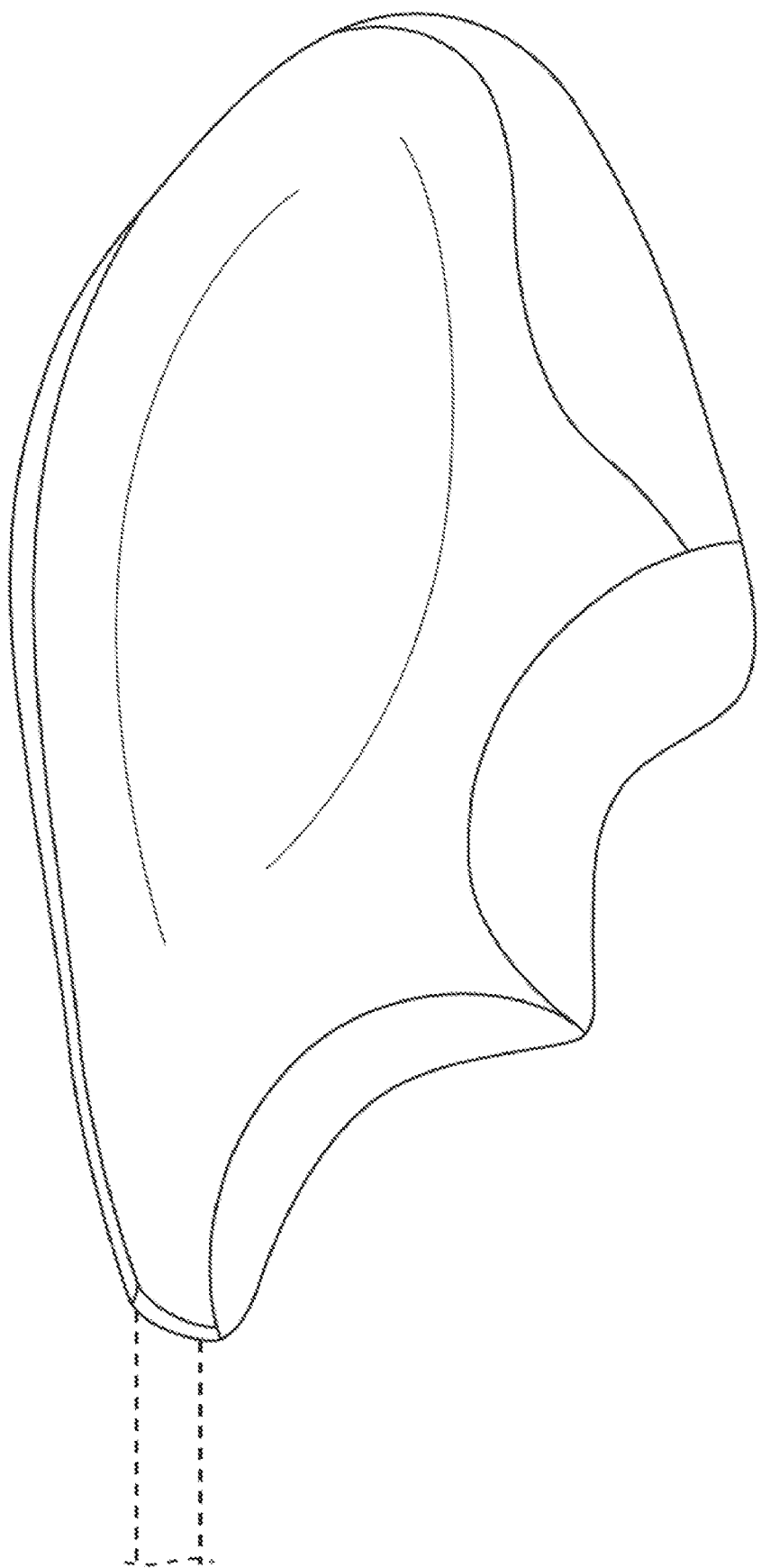
FIG. 1F is a Side 1 view of the handle of FIG. 1A.
Figure 1G:
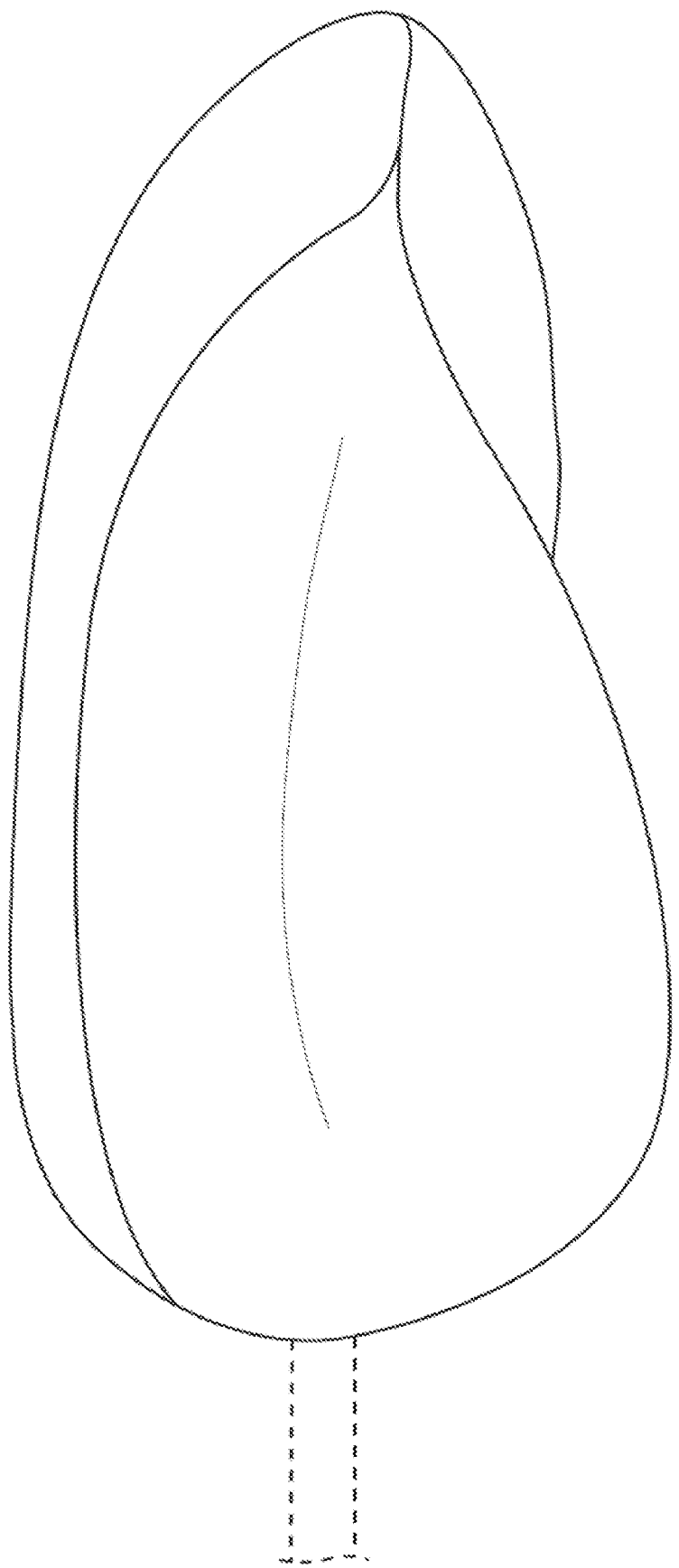
FIG. 1G is a front view of the handle of FIG. 1A.
Figure 1H:
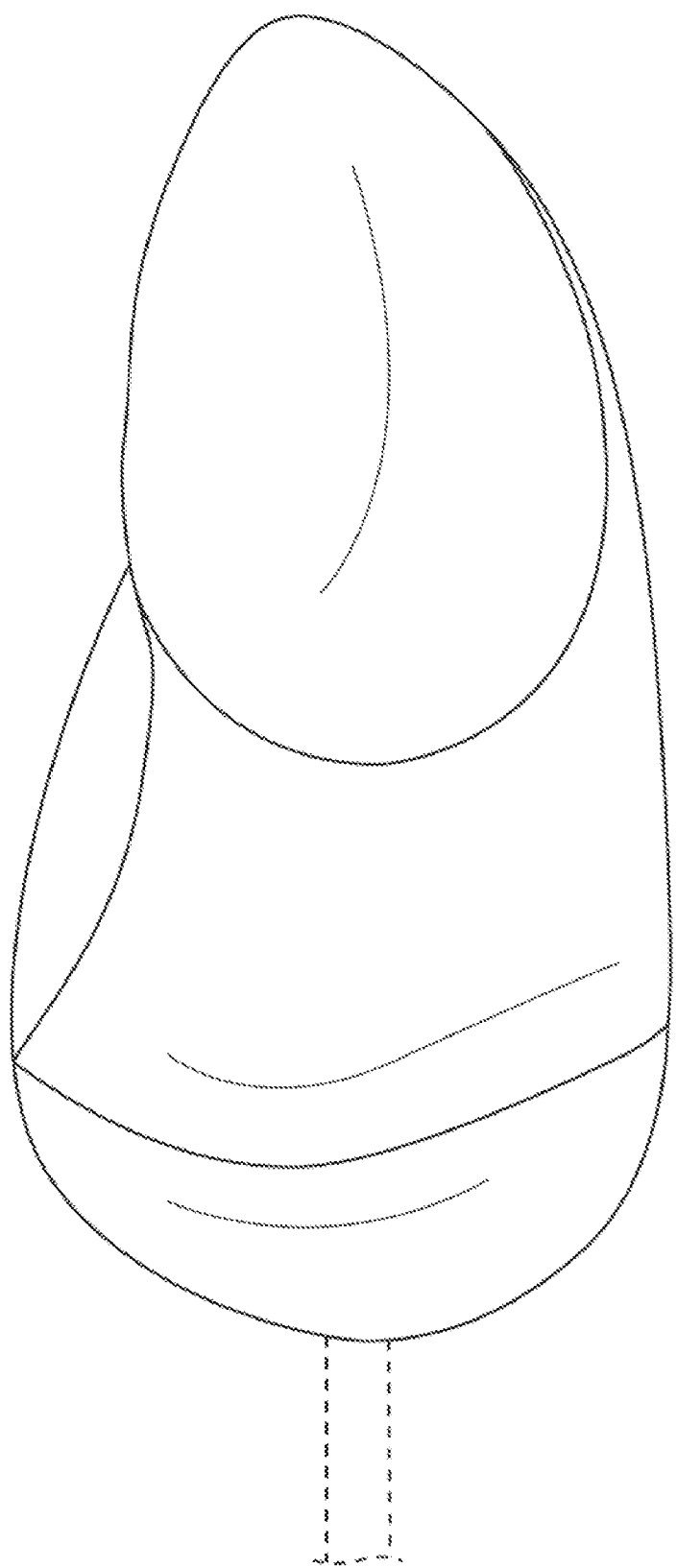
FIG. 1H is a back view of the handle of FIG. 1A.
Figure 2A:
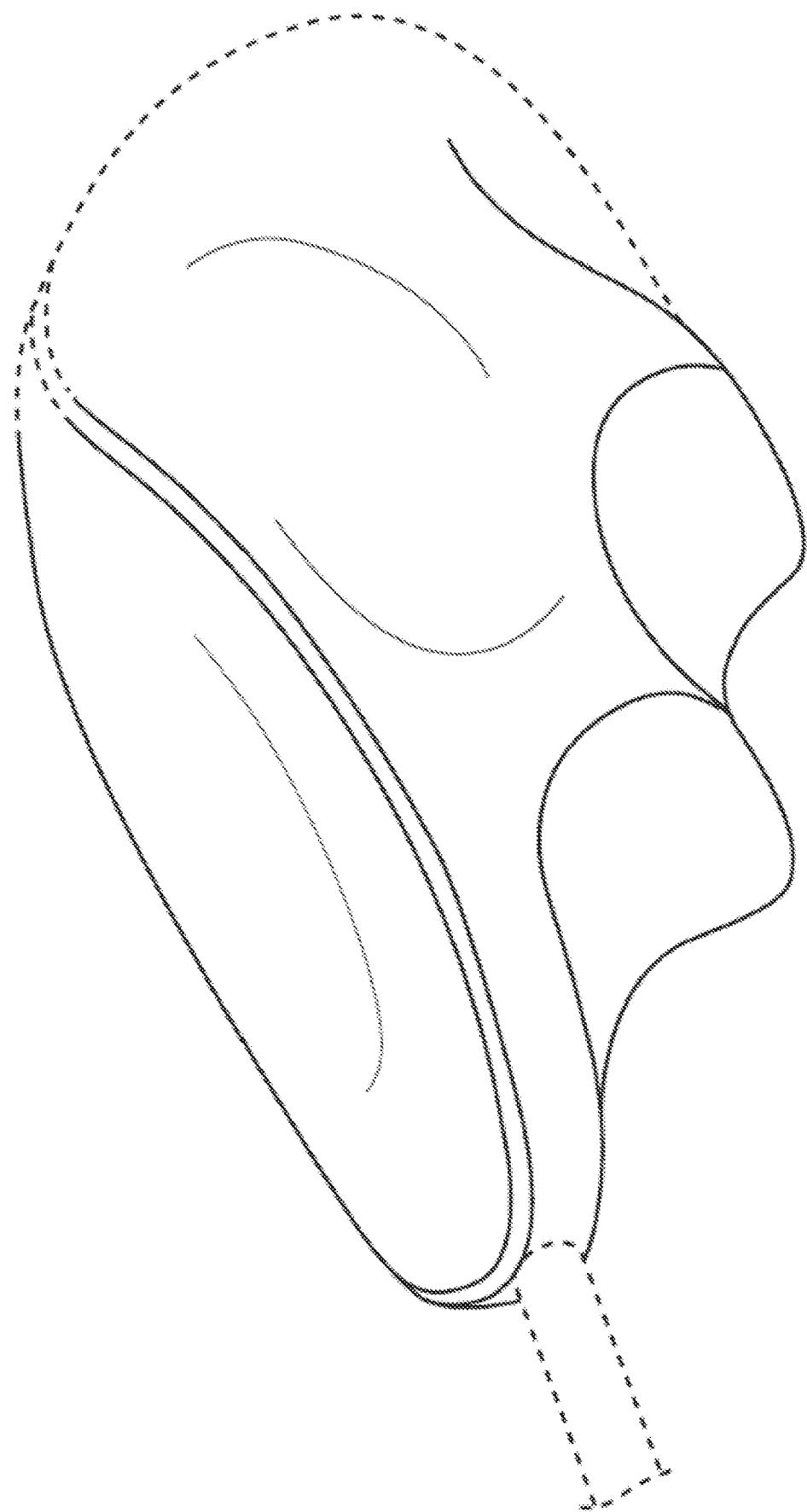
FIG. 2A is a perspective view of Side 1 of a handle, according to an embodiment.
Figure 2B:
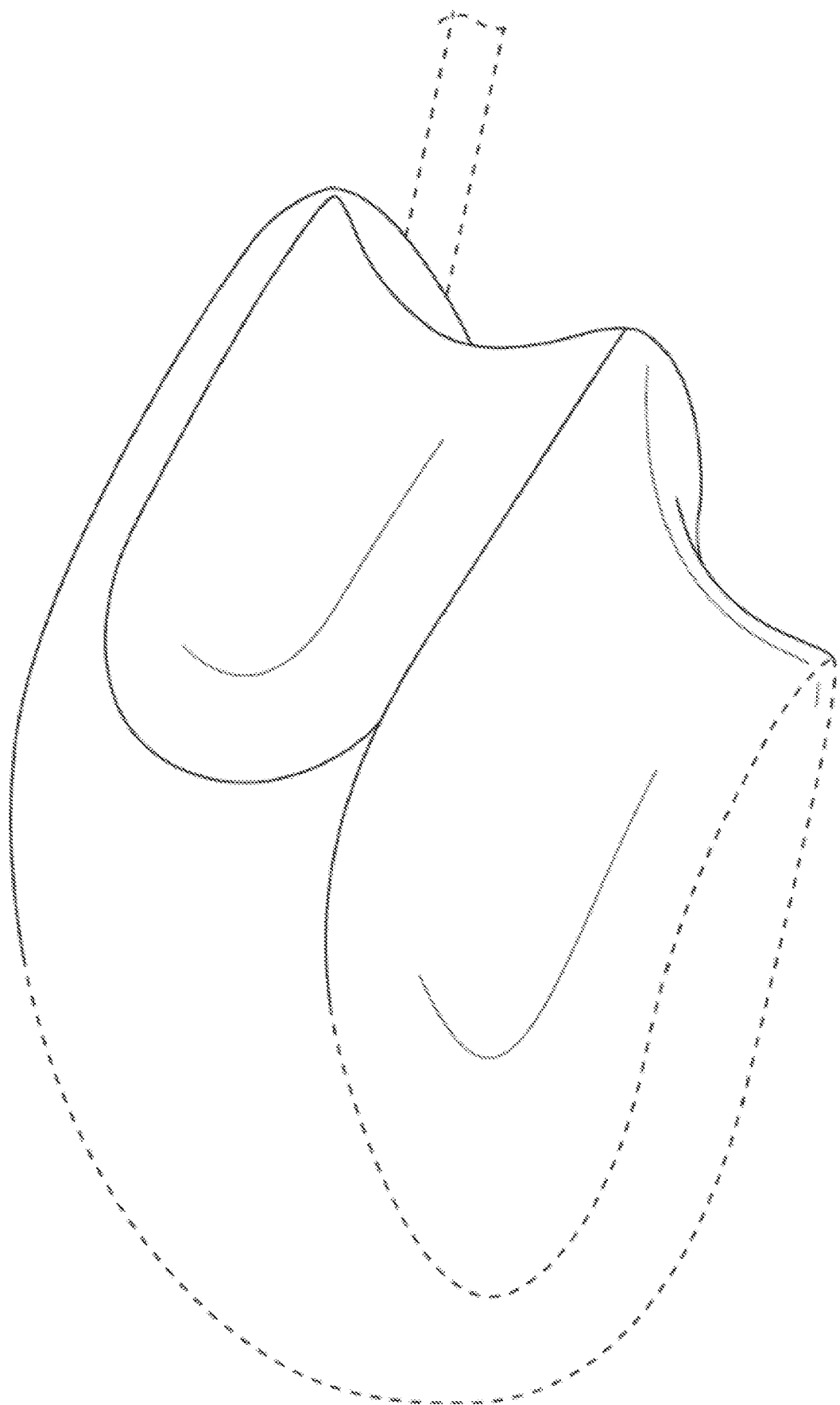
FIG. 2B is a perspective view of Side 2 of the handle of FIG. 2A.
Figure 2C:
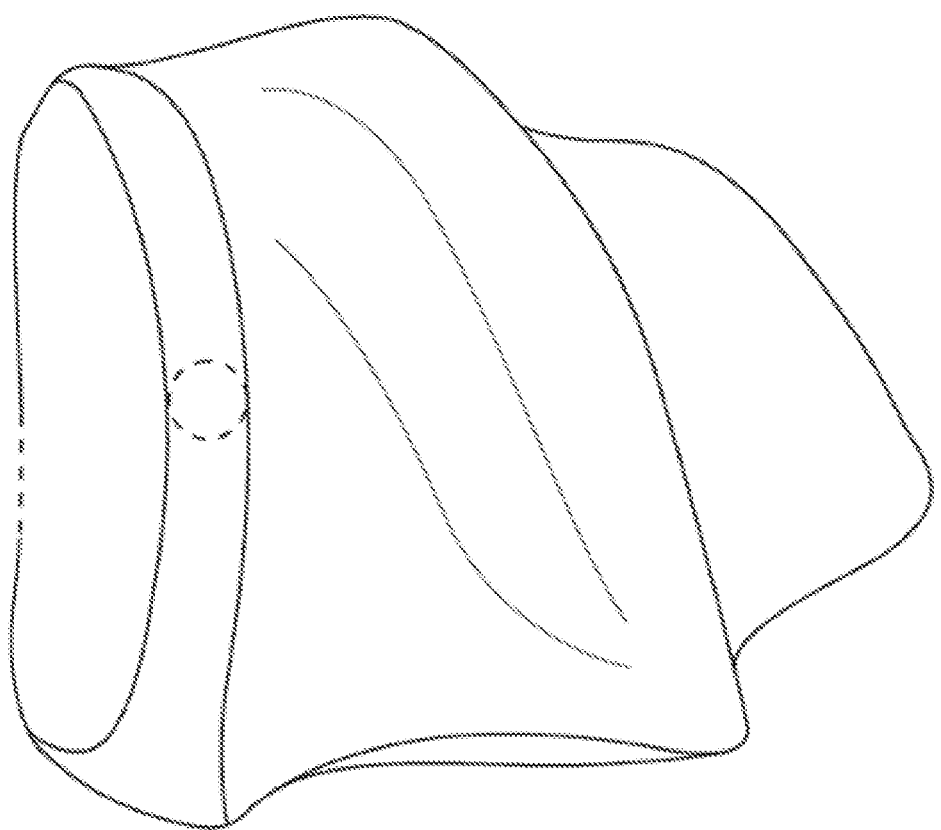
FIG. 2C is a top view of the handle of FIG. 2A.
Figure 2D:
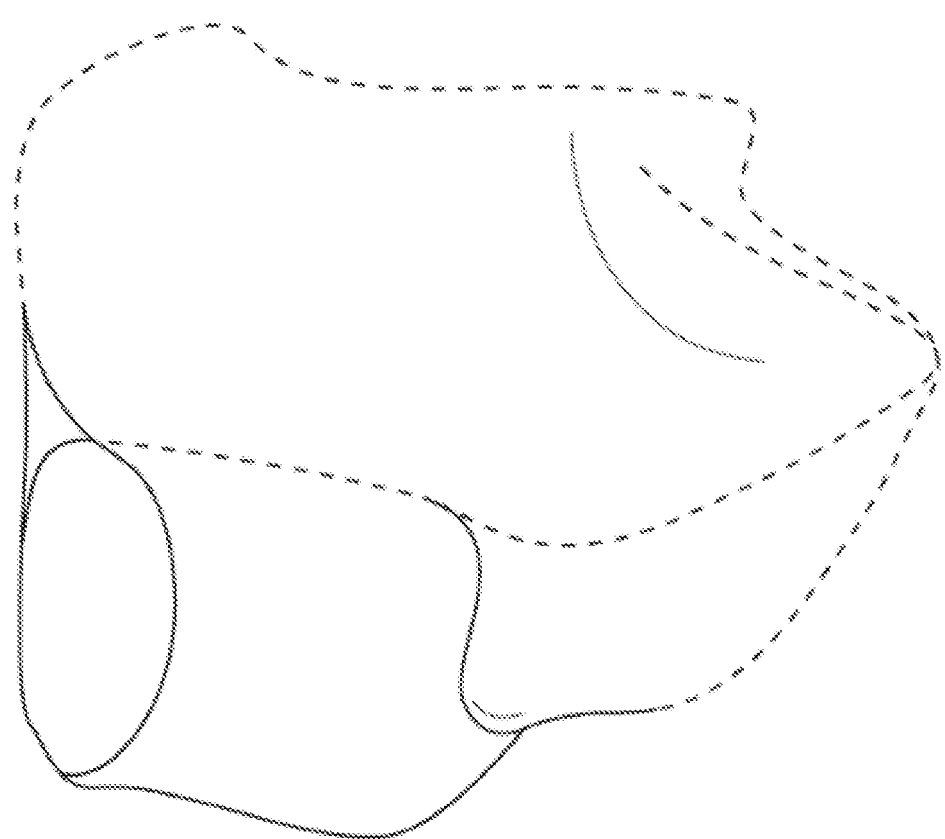
FIG. 2D is a bottom view of the handle of FIG. 2A.
Figure 2E:
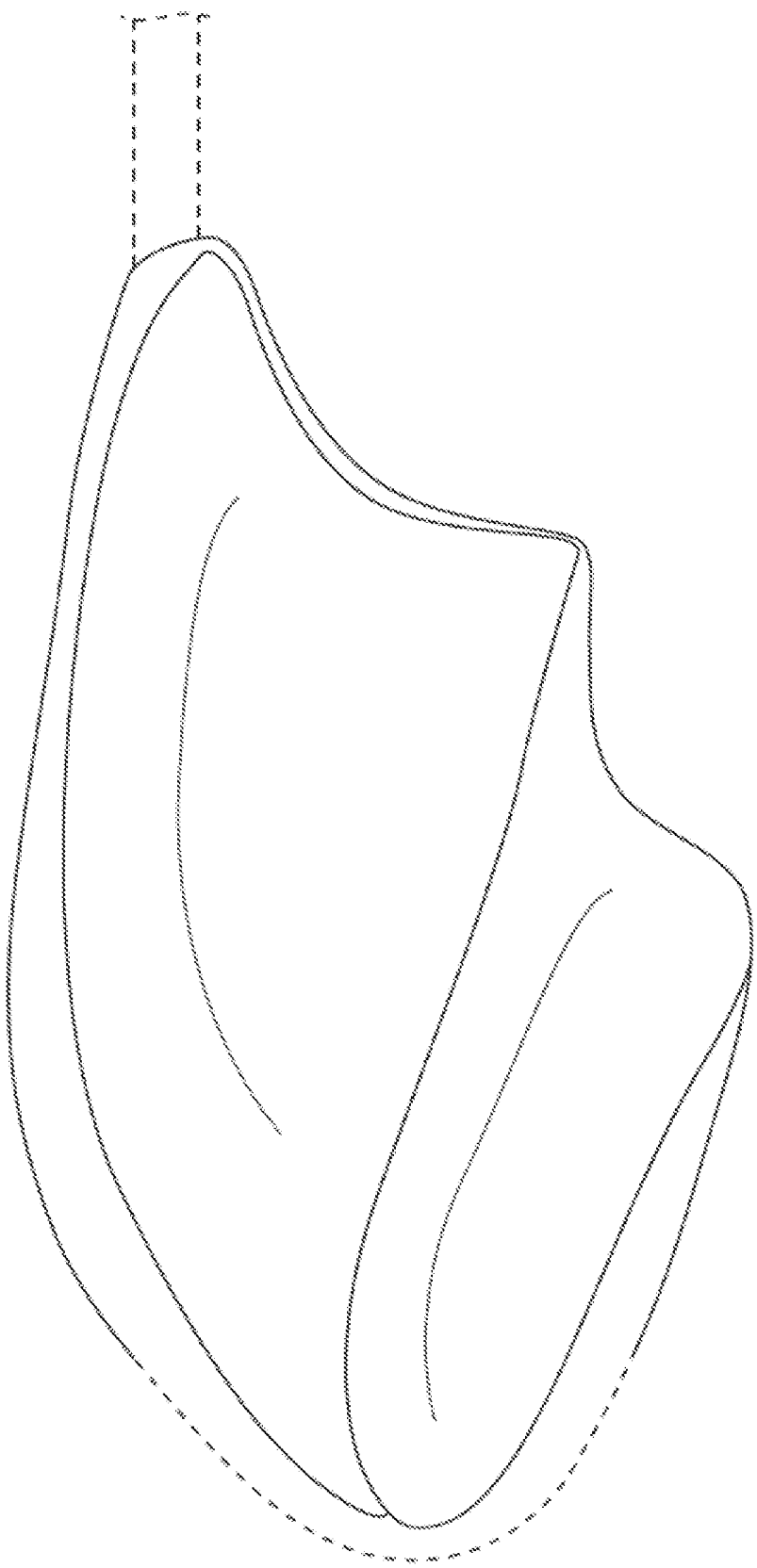
FIG. 2E is a Side 2 view of the handle of FIG. 2A.
Figure 2F:
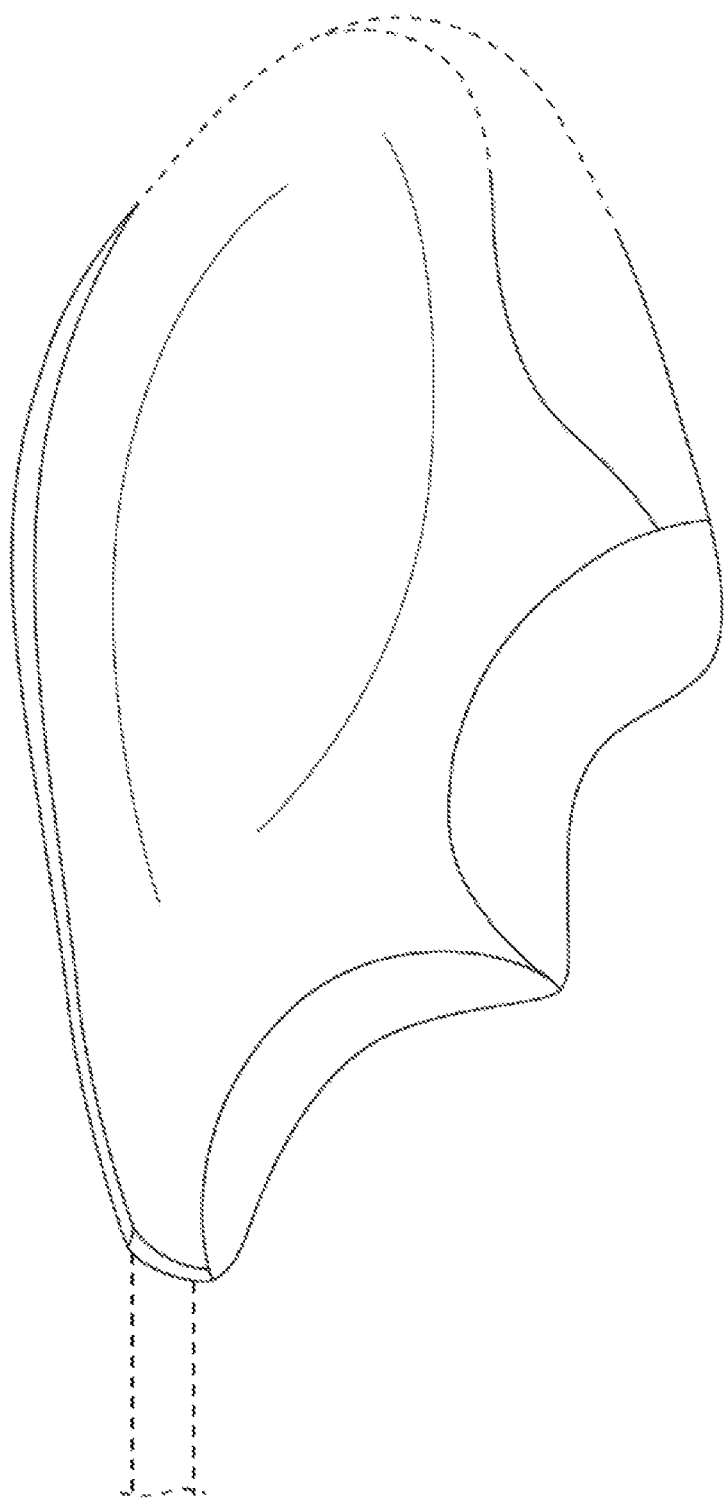
FIG. 2F is a Side 1 view of the handle of FIG. 2A.
Figure 2G:
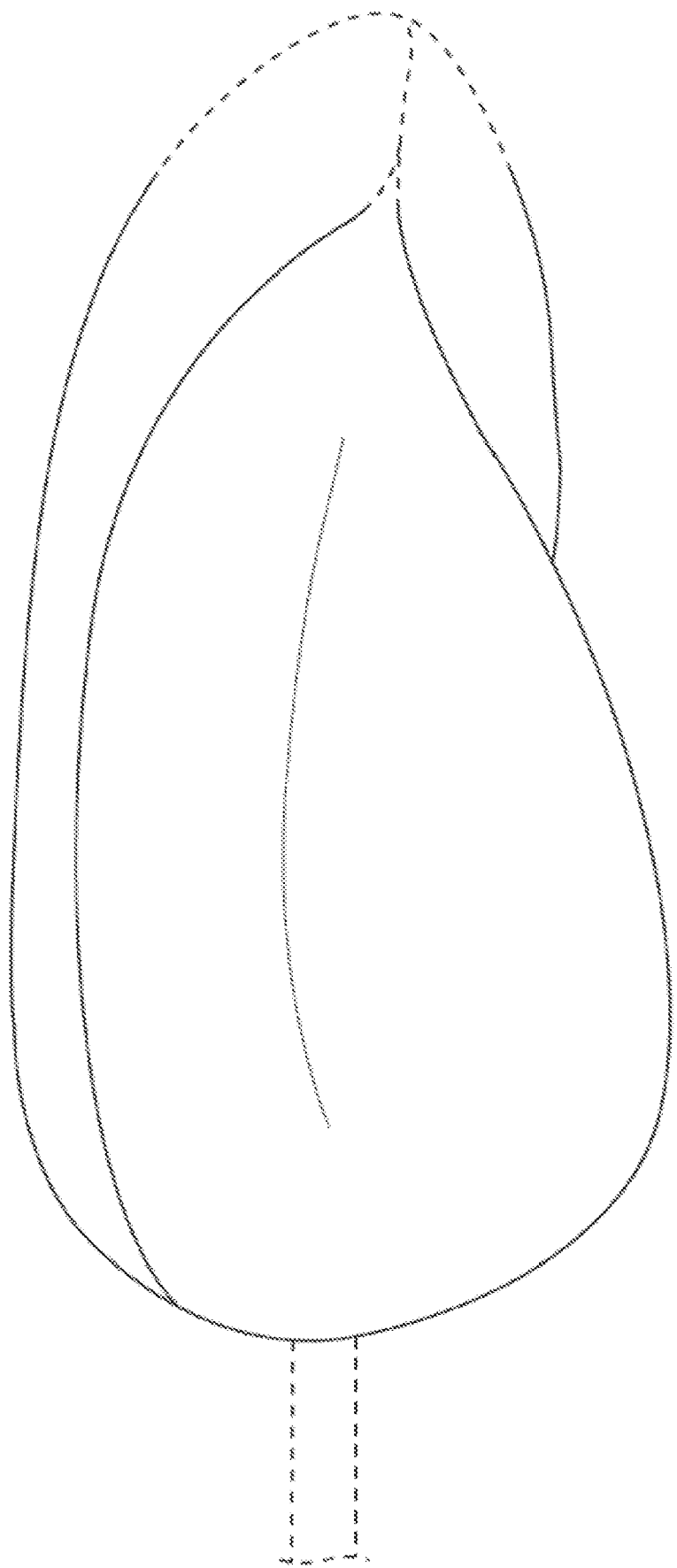
FIG. 2G is a front view of the handle of FIG. 2A.
Figure 2H:
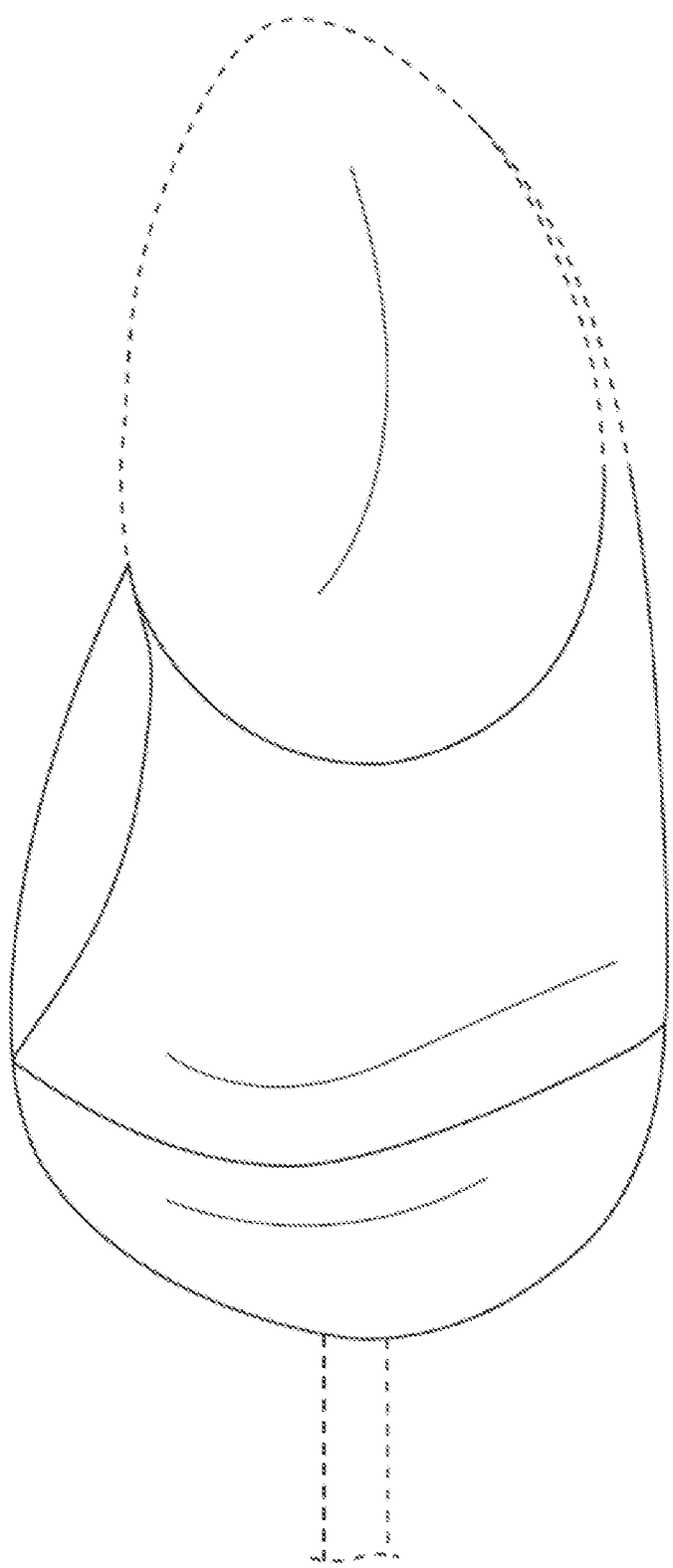
FIG. 2H is a back view of the handle of FIG. 2A.
Figure 3A:
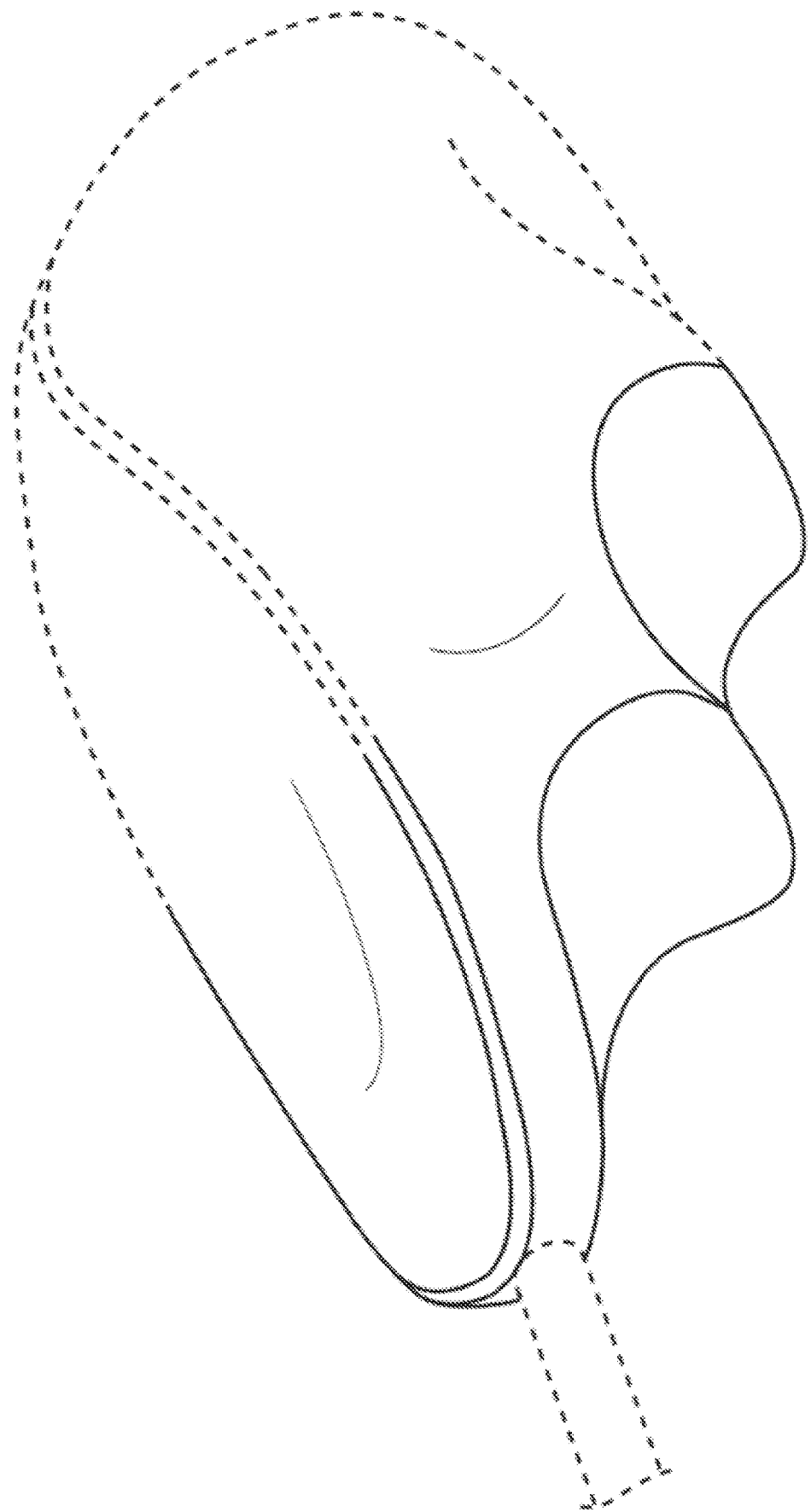
FIG. 3A is a perspective view of Side 1 of a handle, according to an embodiment.
Figure 3B:
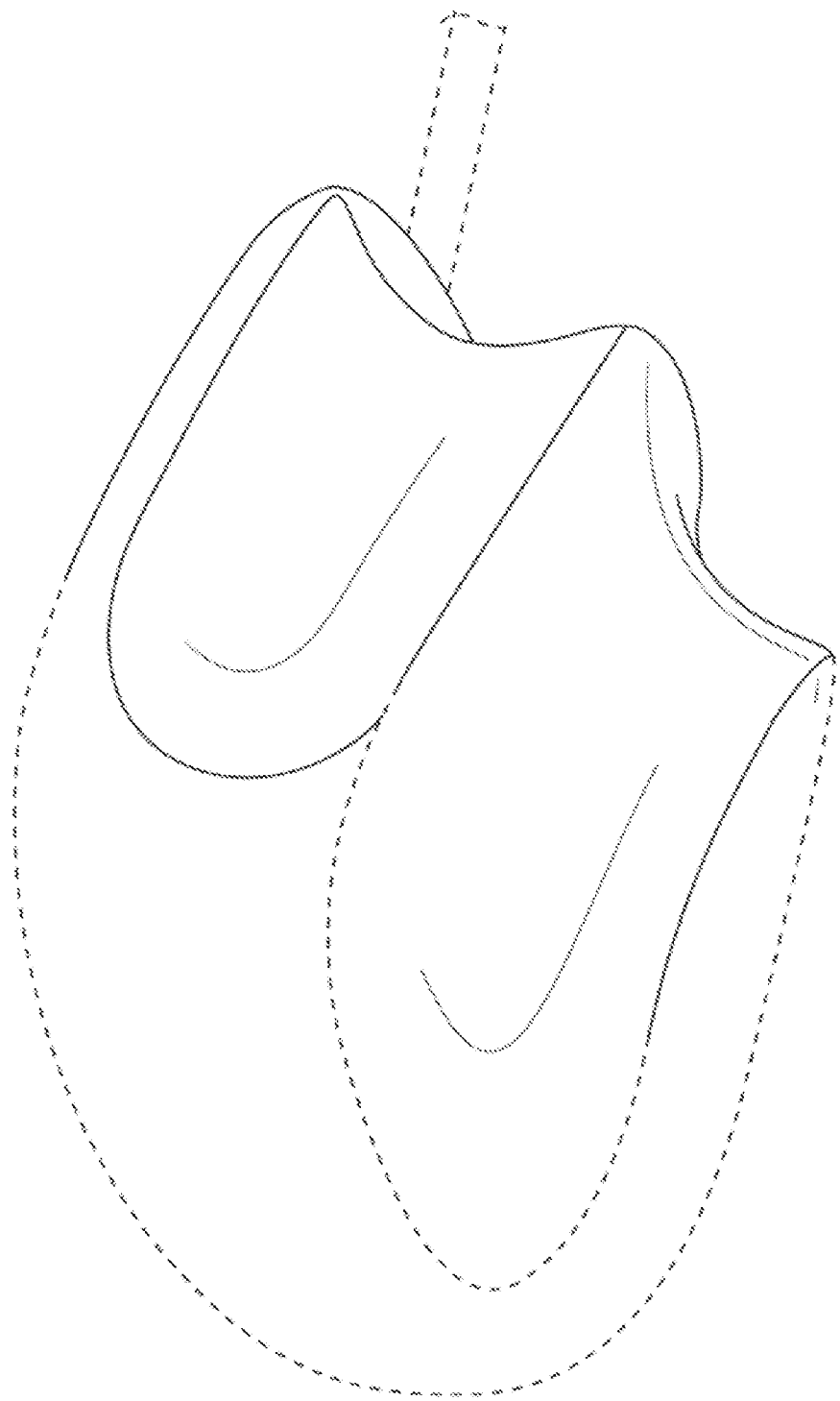
FIG. 3B is a perspective view of Side 2 of the handle of FIG. 3A.
Figure 3C:
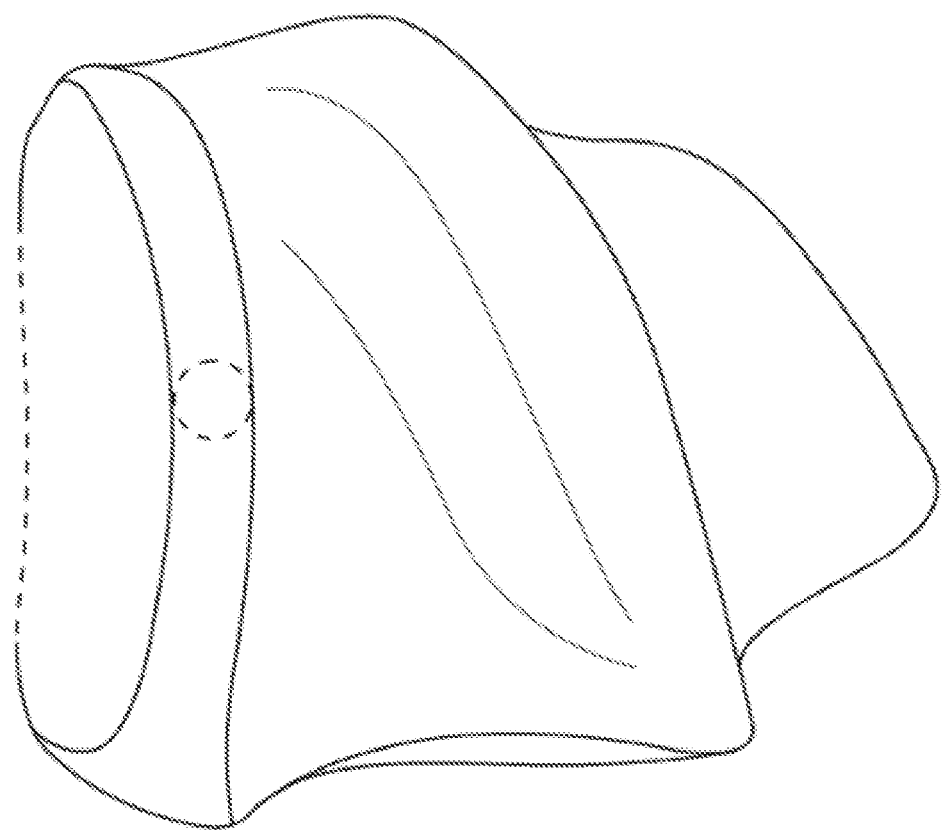
FIG. 3C is a top view of the handle of FIG. 3A.
Figure 3D:
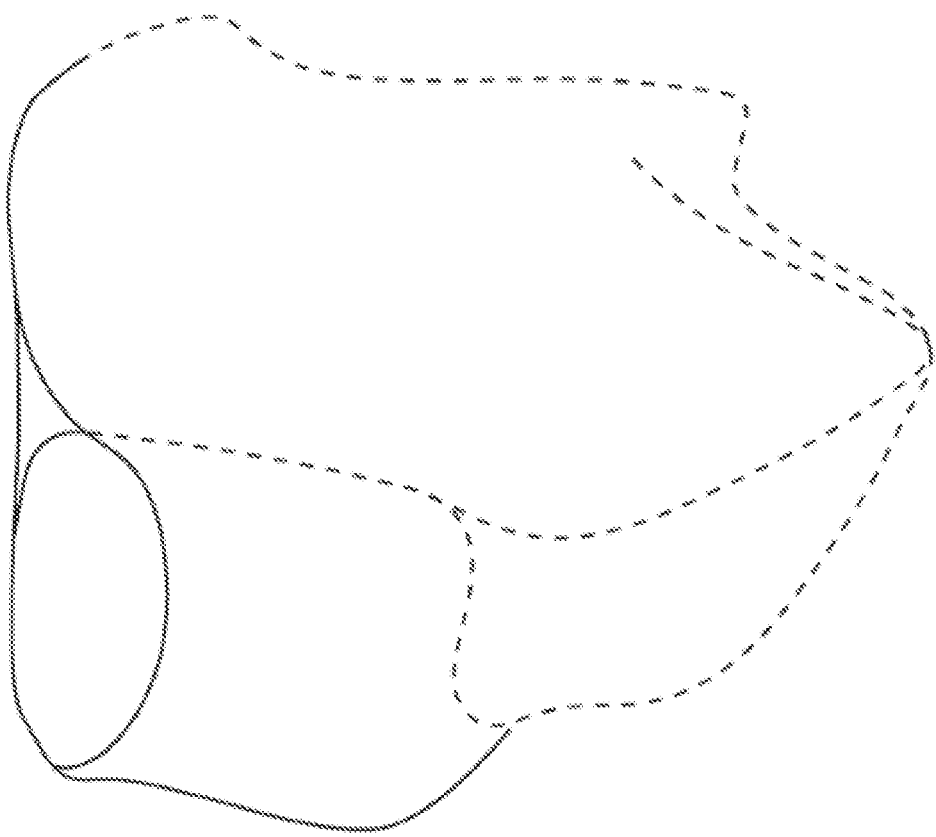
FIG. 3D is a bottom view of the handle of FIG. 3A.
Figure 3E:
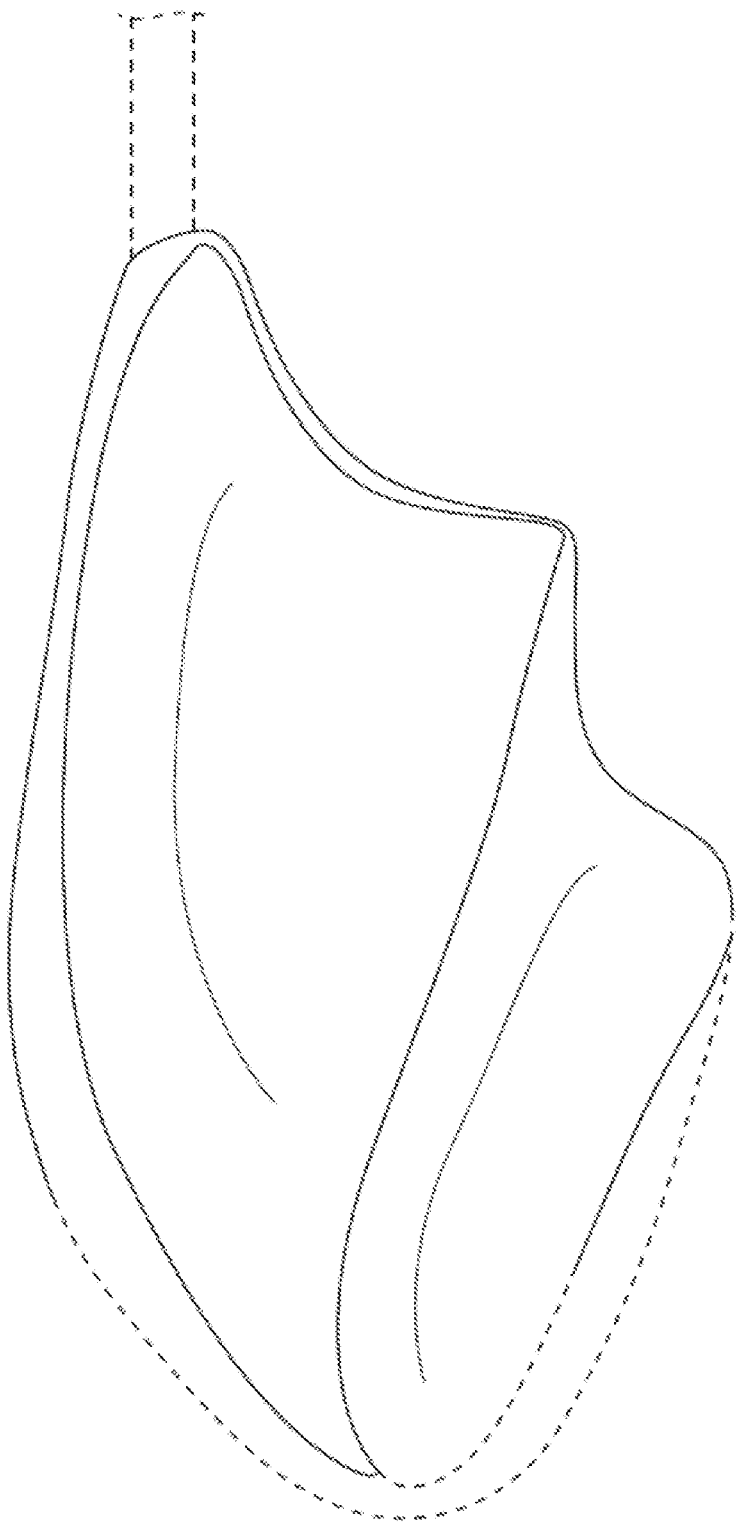
FIG. 3E is a Side 2 view of the handle of FIG. 3A.
Figure 3F:
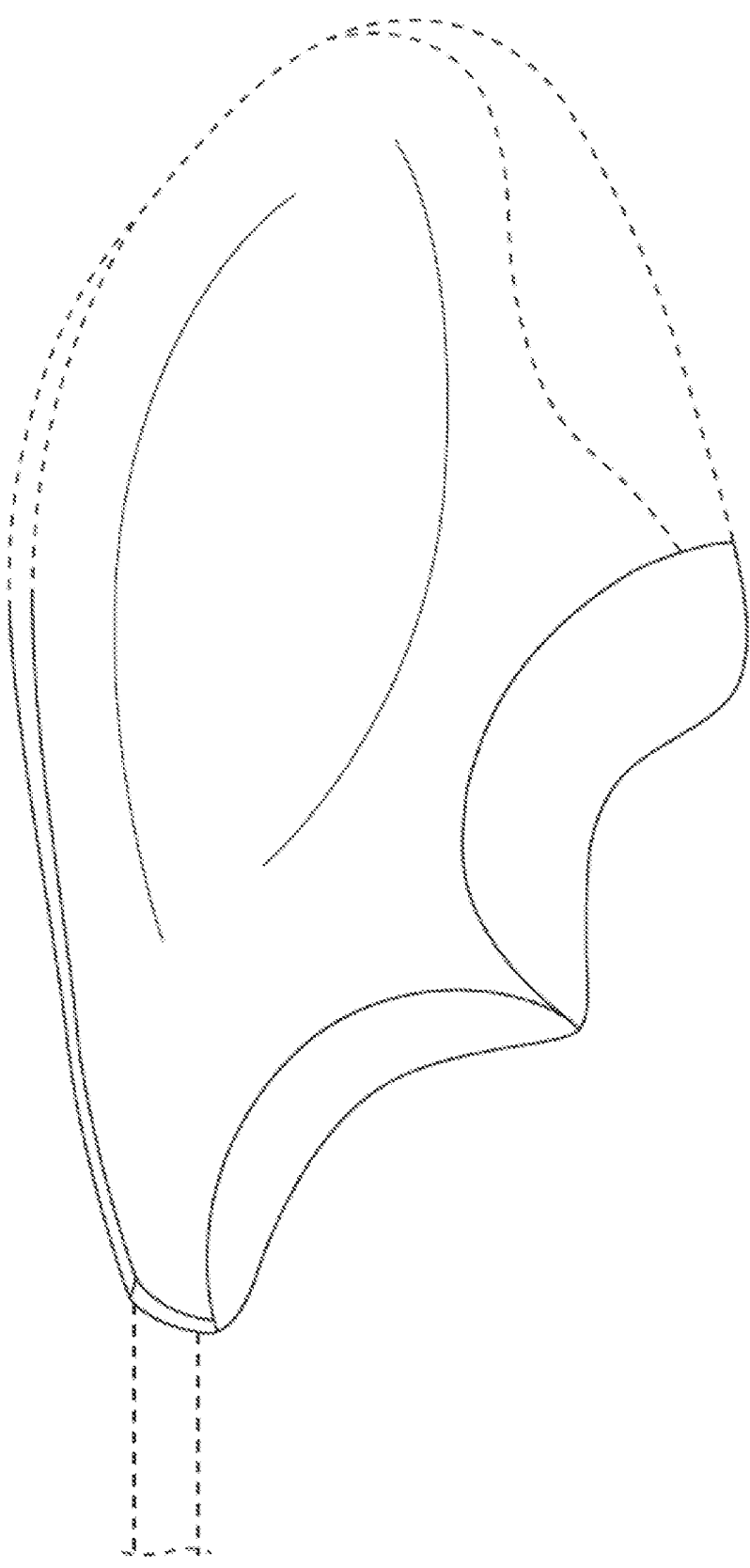
FIG. 3F is a Side 1 view of the handle of FIG. 3A.
Figure 3G:
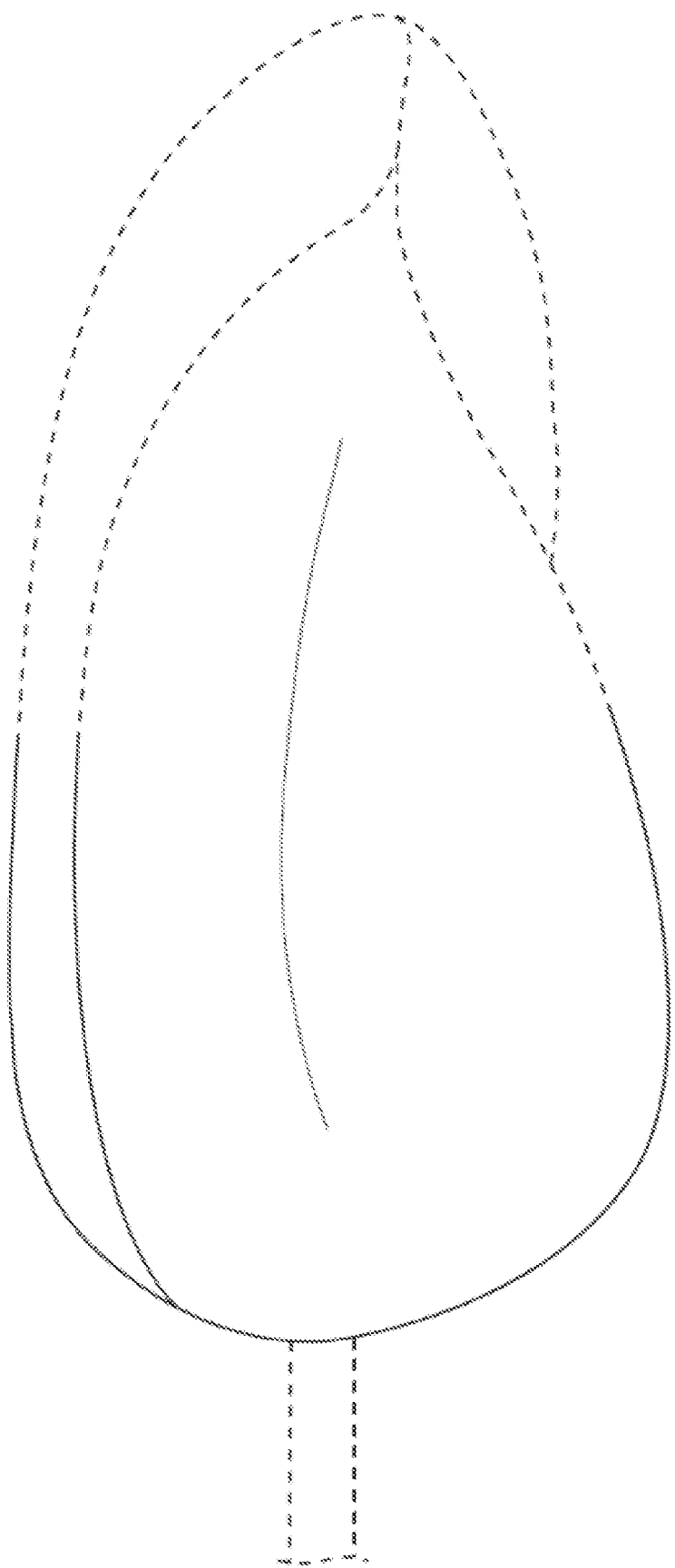
FIG. 3G is a front view of the handle of FIG. 3A.
Figure 3H:
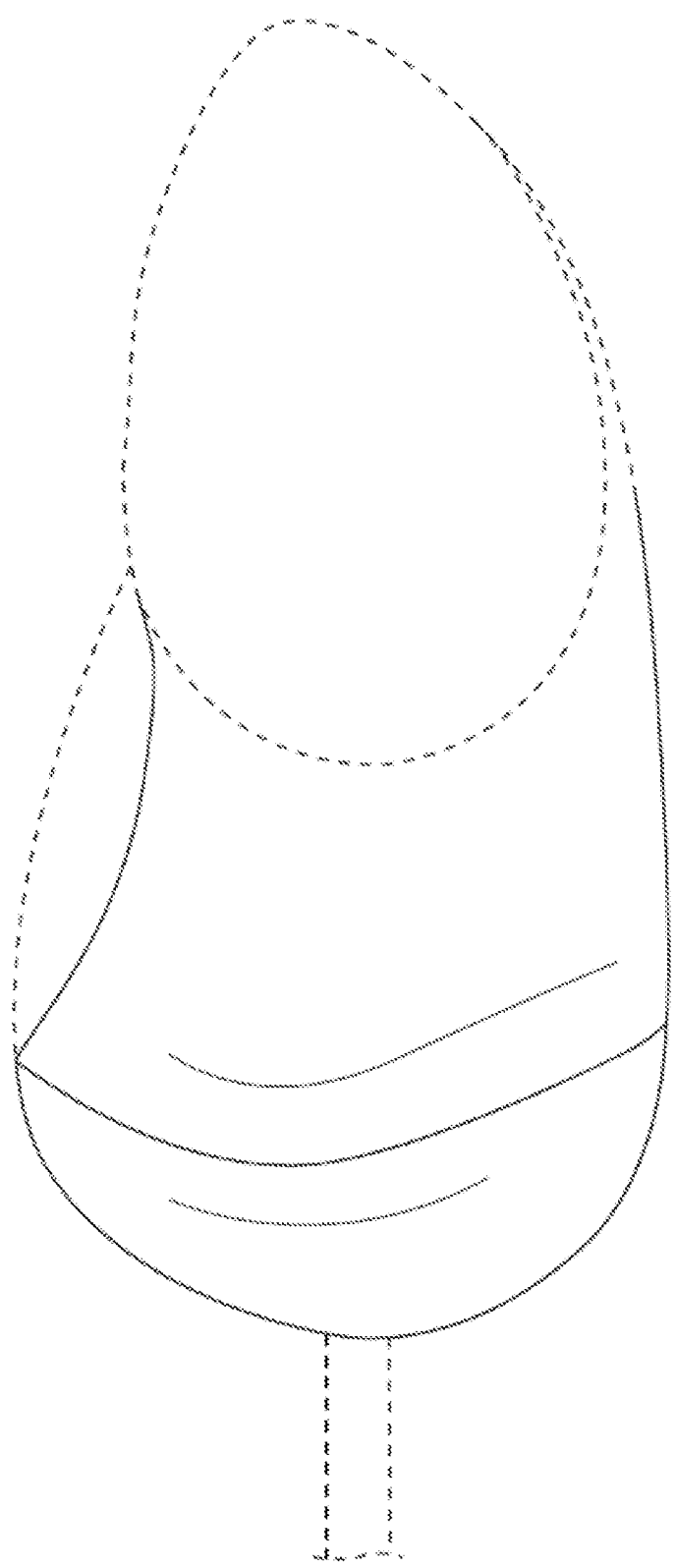
FIG. 3H is a back view of the handle of FIG. 3A.
Figure 4A:
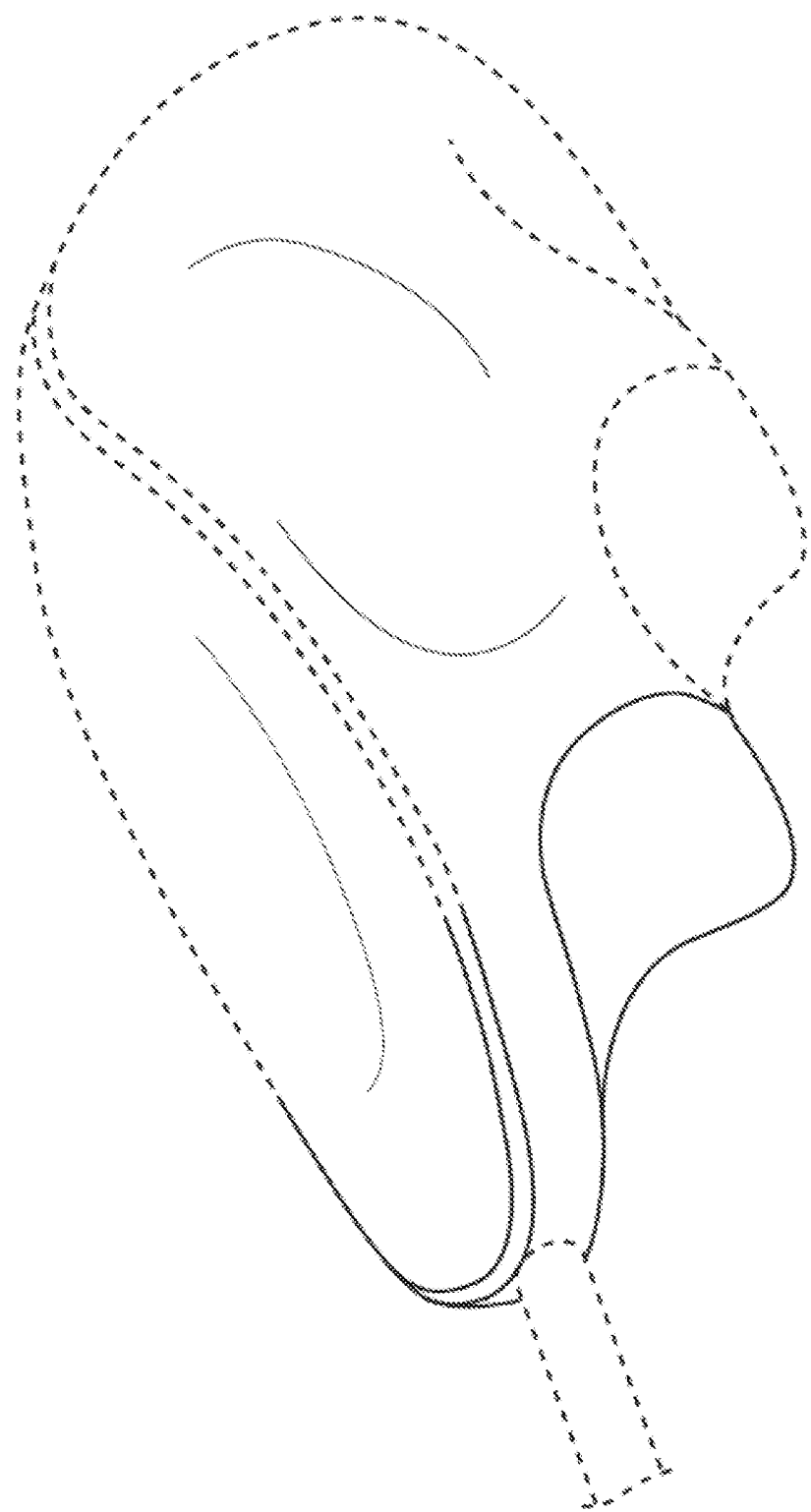
FIG. 4A is a perspective view of Side 1 of a handle, according to an embodiment.
Figure 4B:
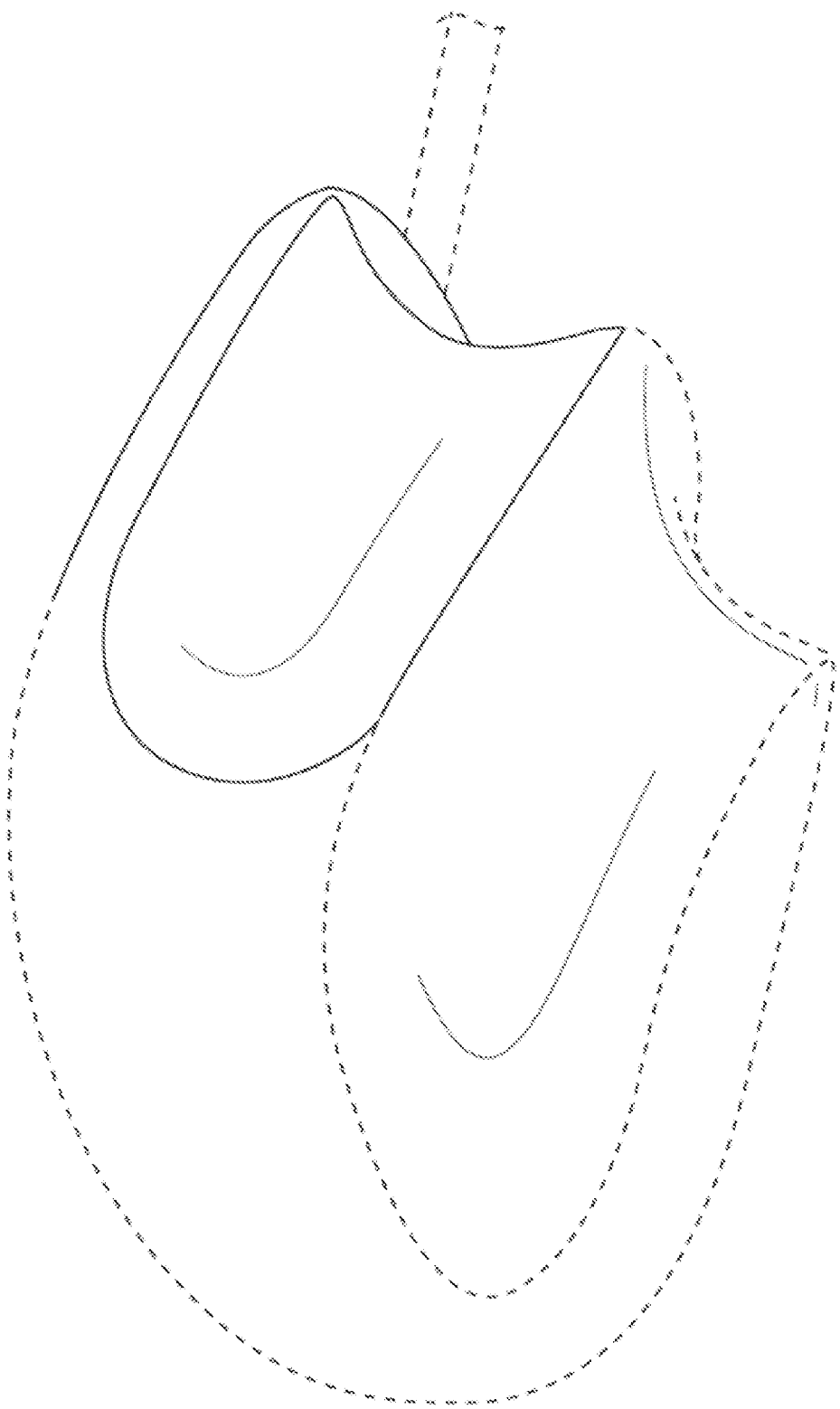
FIG. 4B is a perspective view of Side 2 of the handle of FIG. 4A.
Figure 4C:
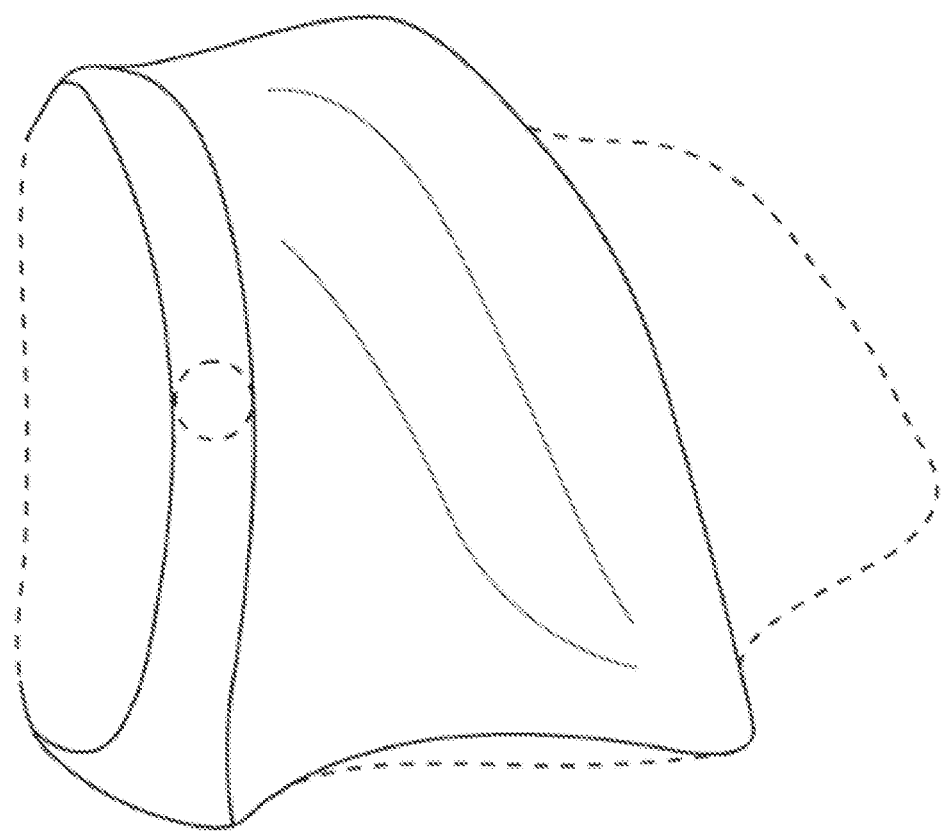
FIG. 4C is a top view of the handle of FIG. 4A.
Figure 4D:
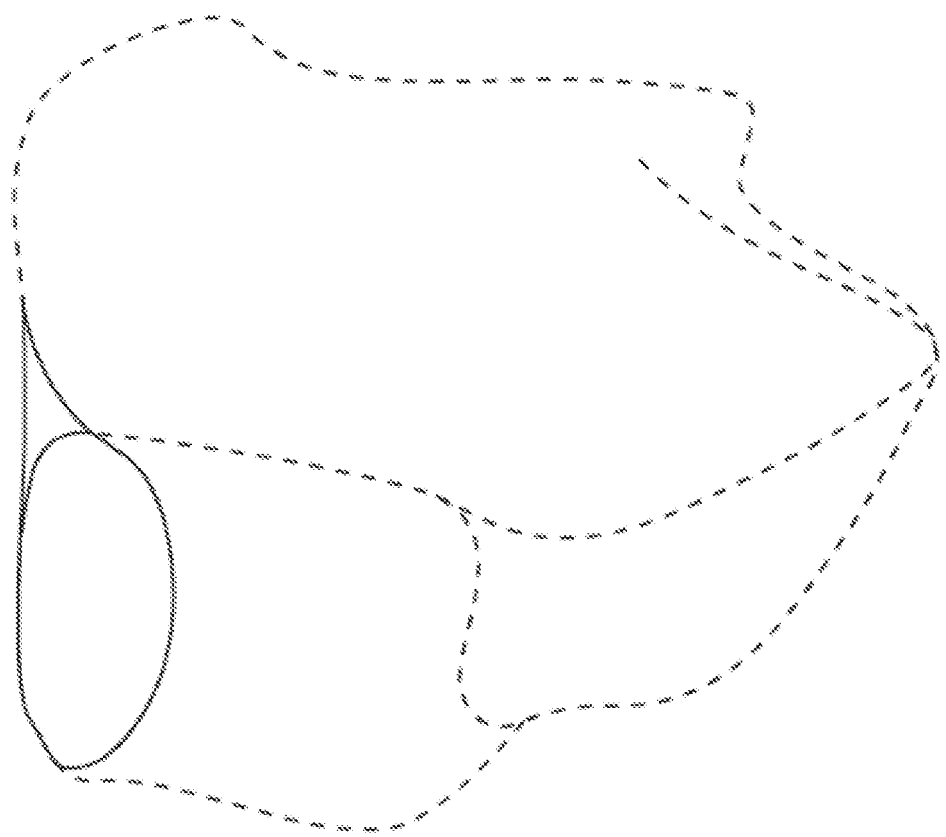
FIG. 4D is a bottom view of the handle of FIG. 4A.
Figure 4E:
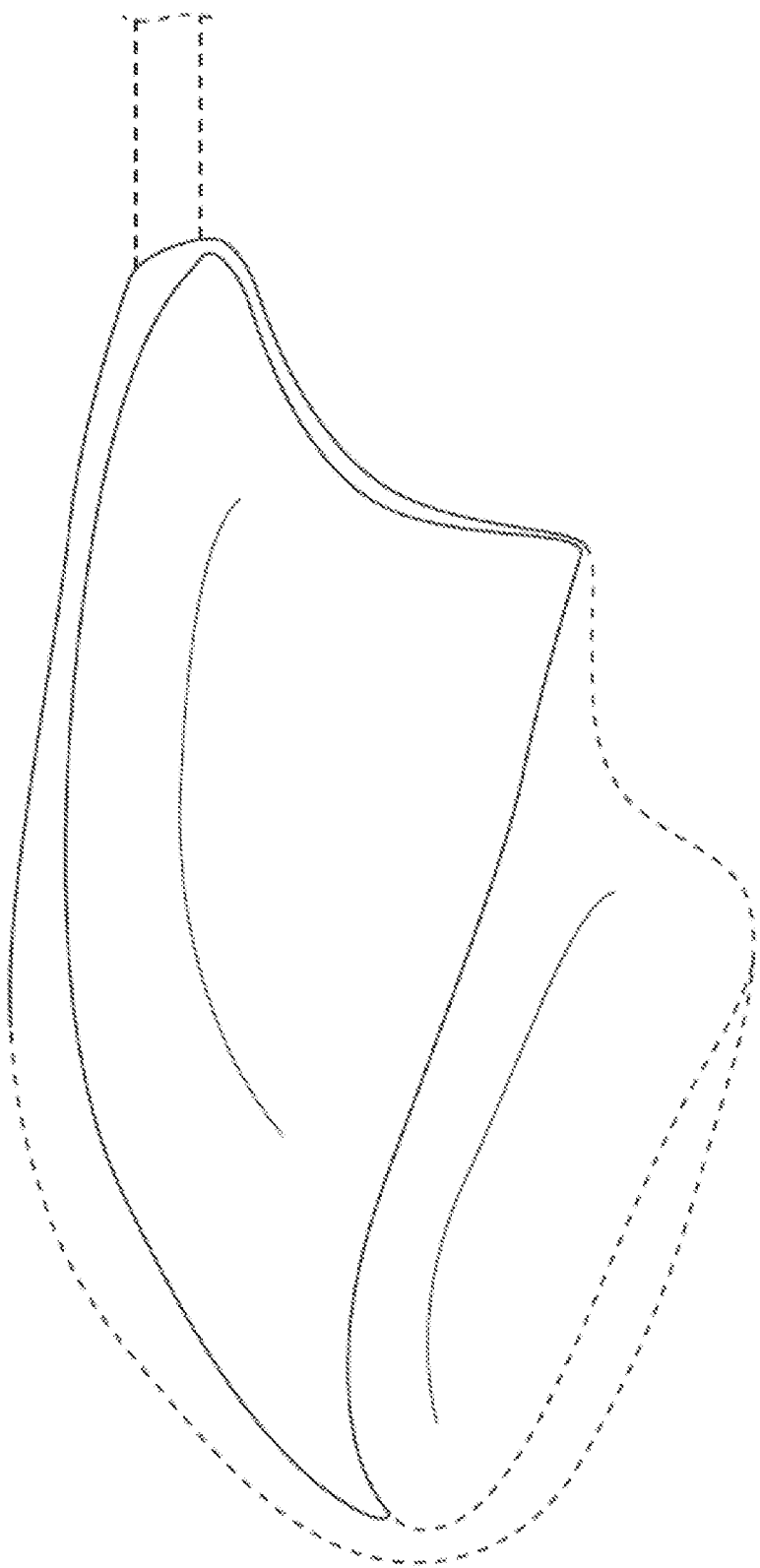
FIG. 4E is a Side 2 view of the handle of FIG. 4A.
Figure 4F:
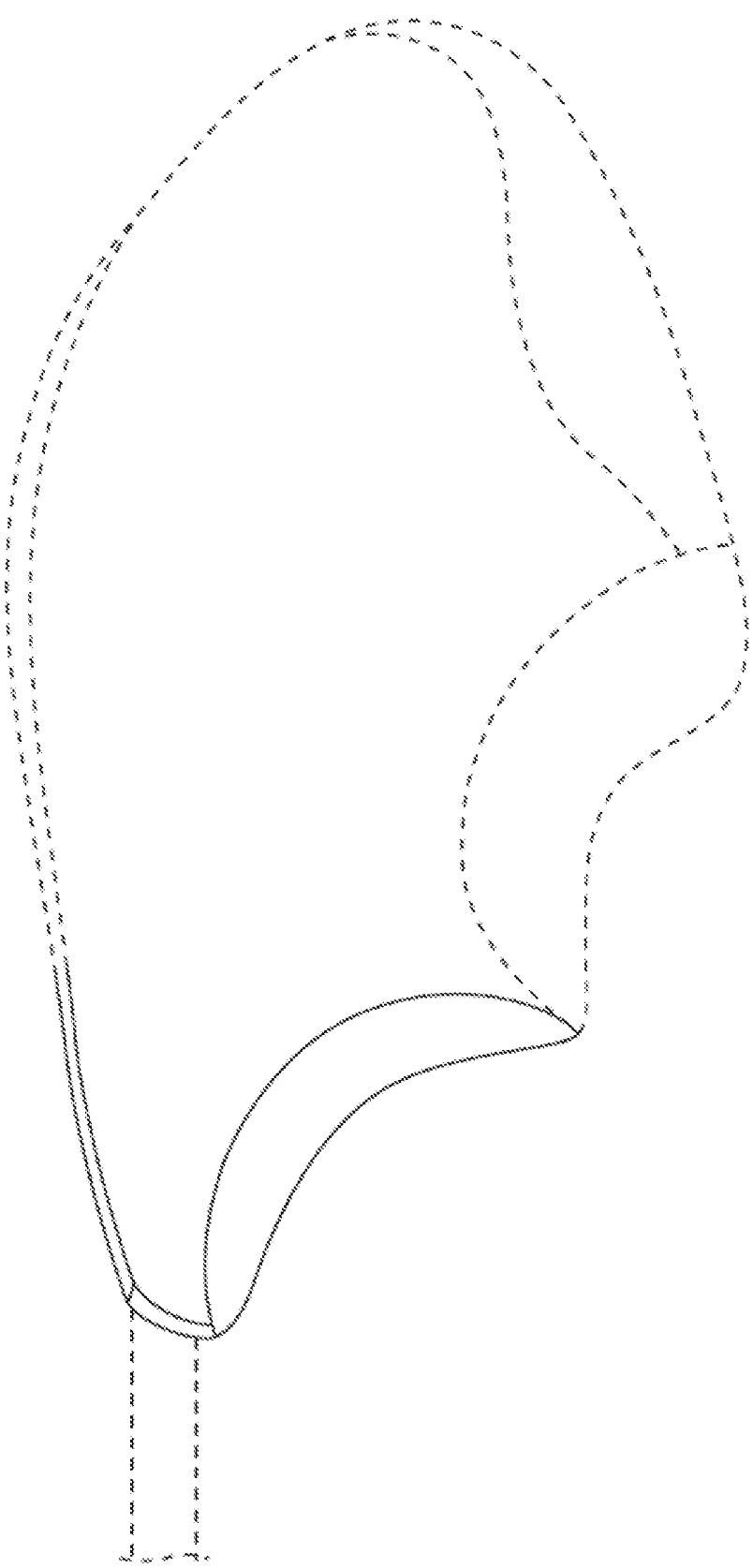
FIG. 4F is a Side 1 view of the handle of FIG. 4A.
Figure 4G:
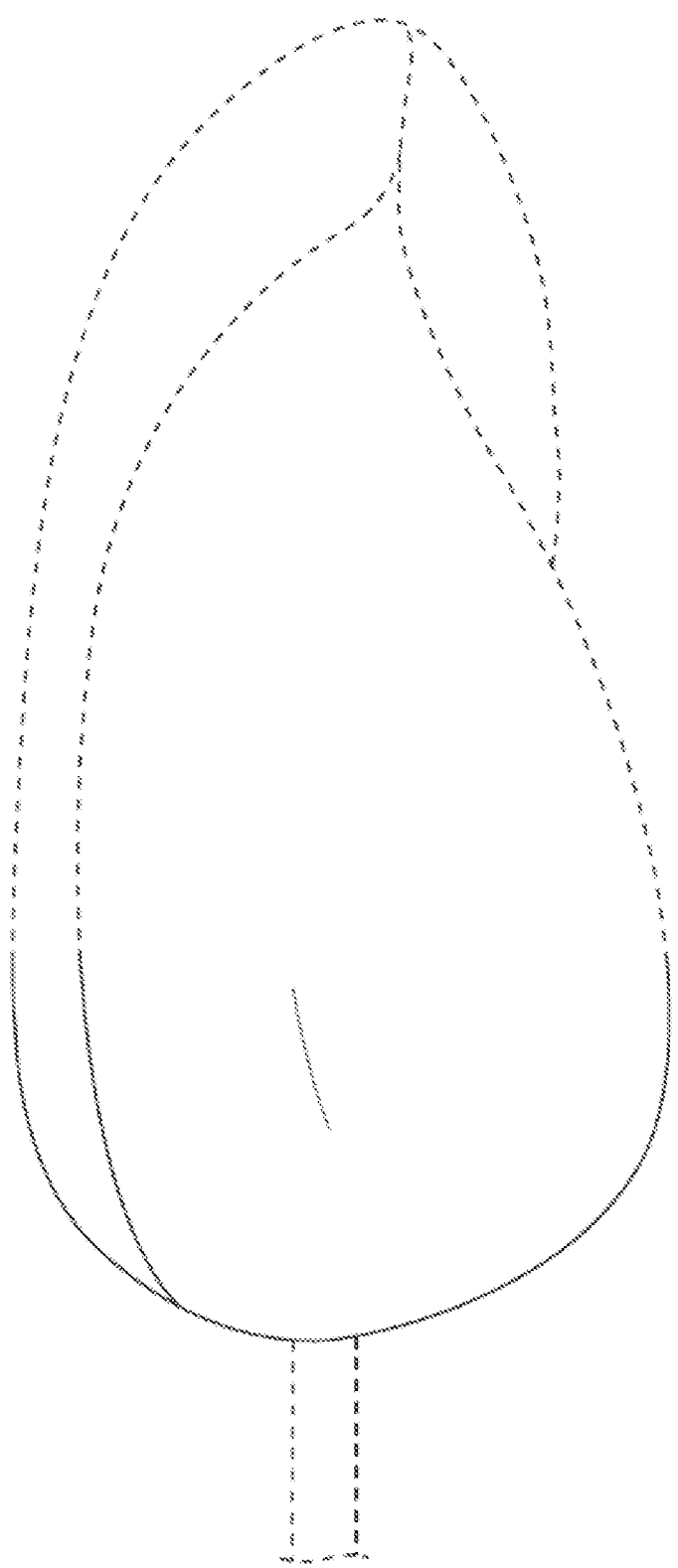
FIG. 4G is a front view of the handle of FIG. 4A.
Figure 4H:
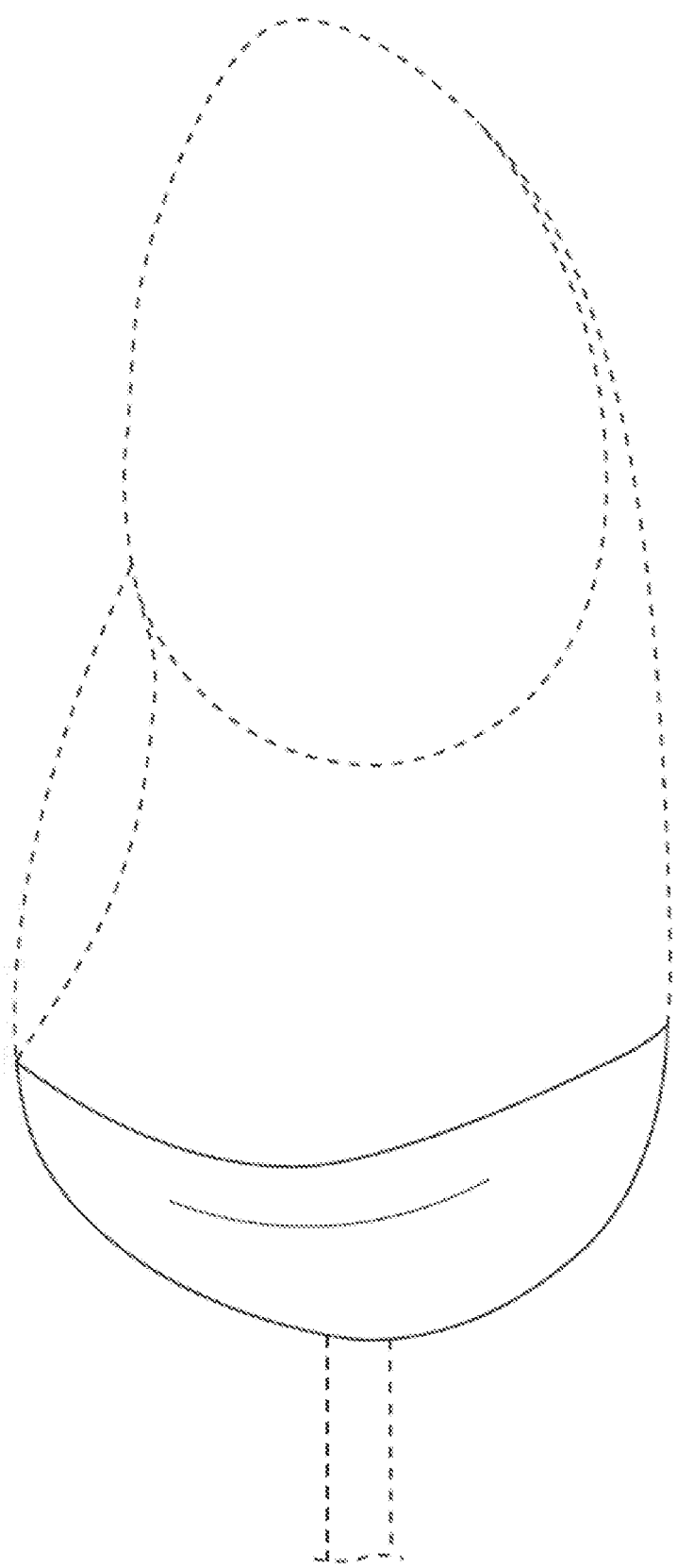
FIG. 4H is a back view of the handle of FIG. 4A.
Figure 5A:
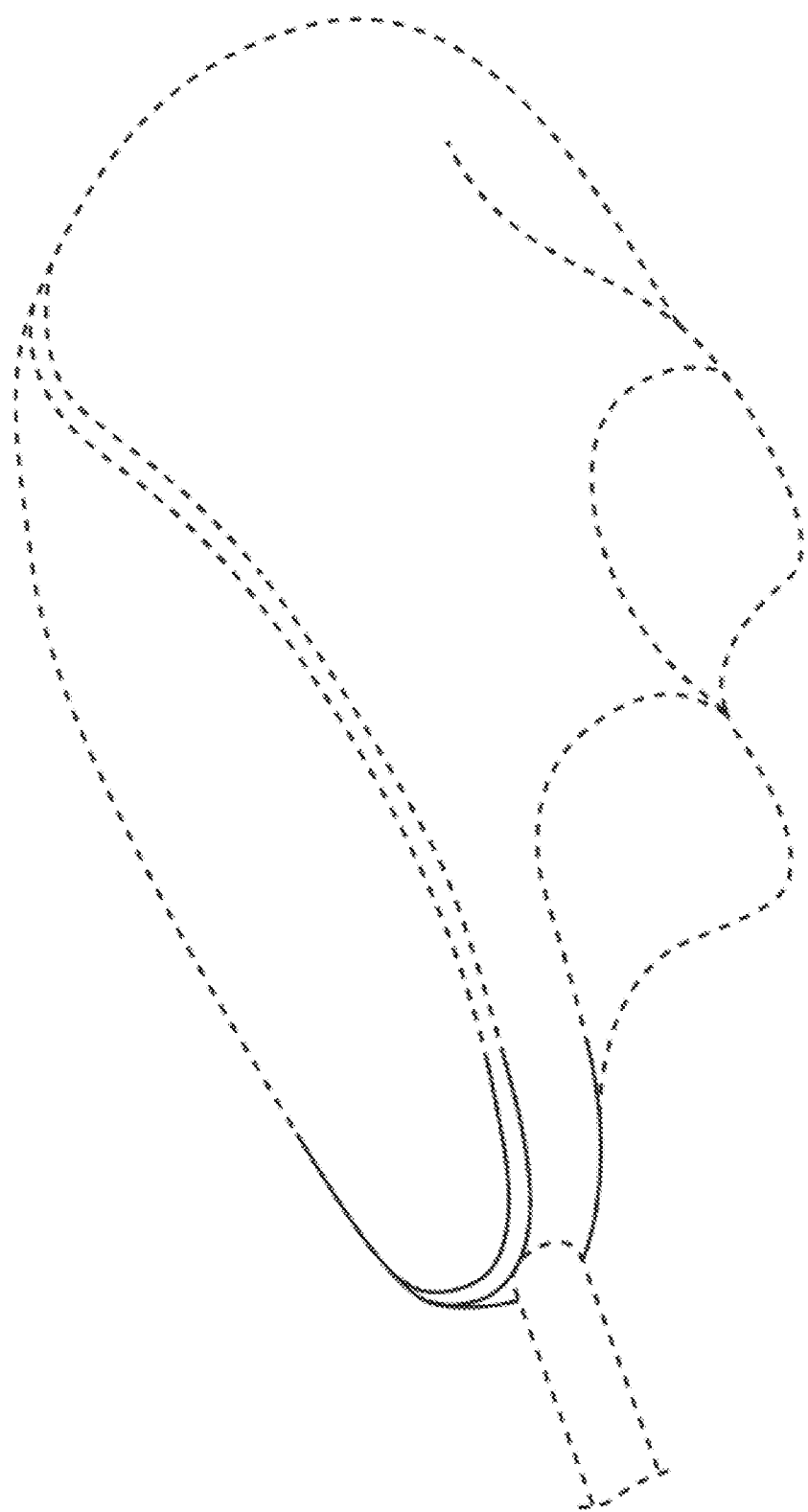
FIG. 5A is a perspective view of Side 1 of a handle, according to an embodiment.
Figure 5B:
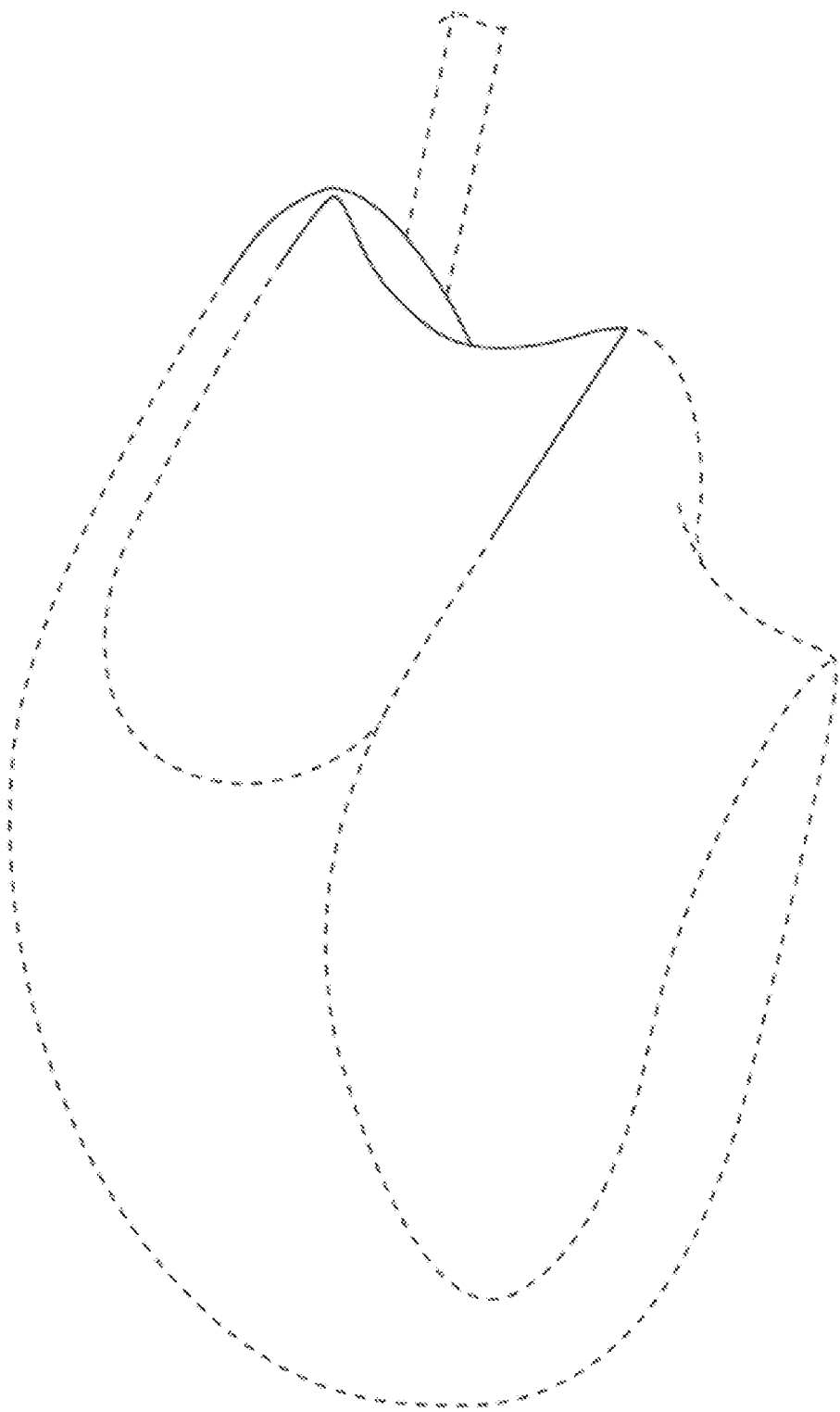
FIG. 5B is a perspective view of Side 2 of the handle of FIG. 5A.
Figure 5C:
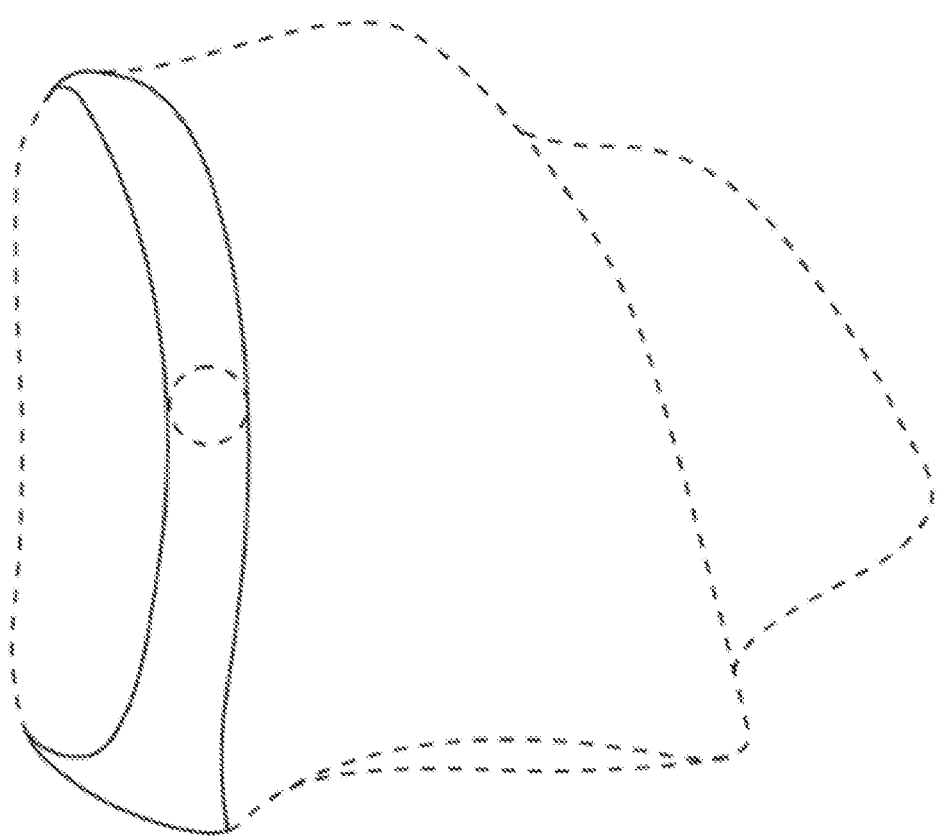
FIG. 5C is a top view of the handle of FIG. 5A.
Figure 5D:
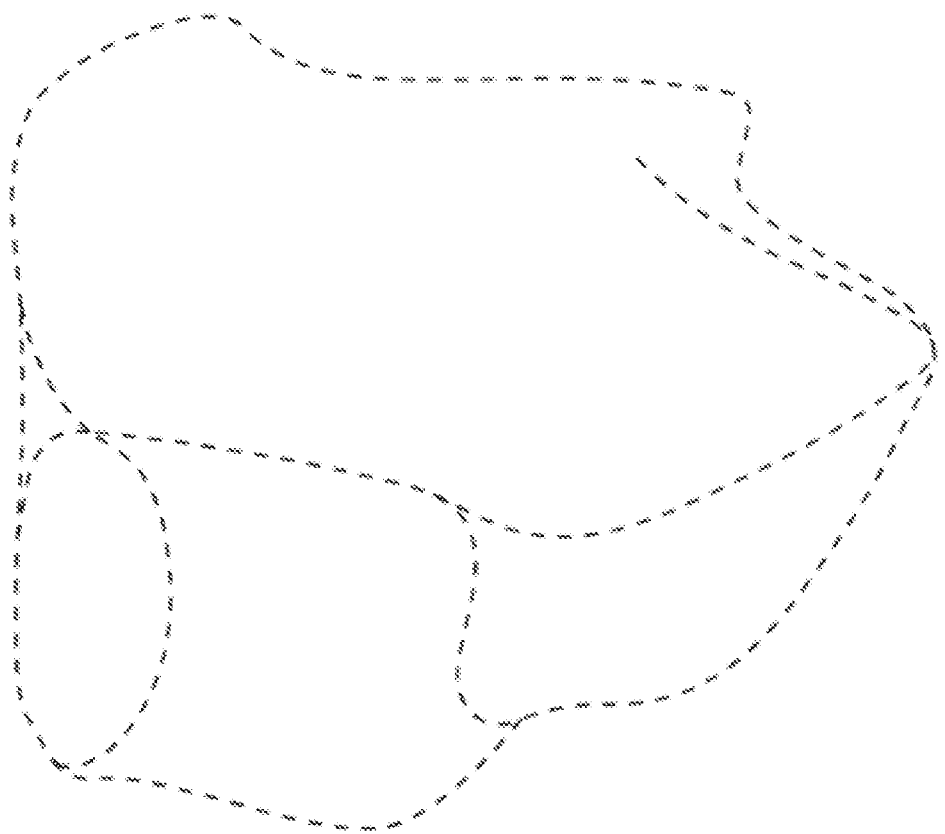
FIG. 5D is a bottom view of the handle of FIG. 5A.
Figure 5E:
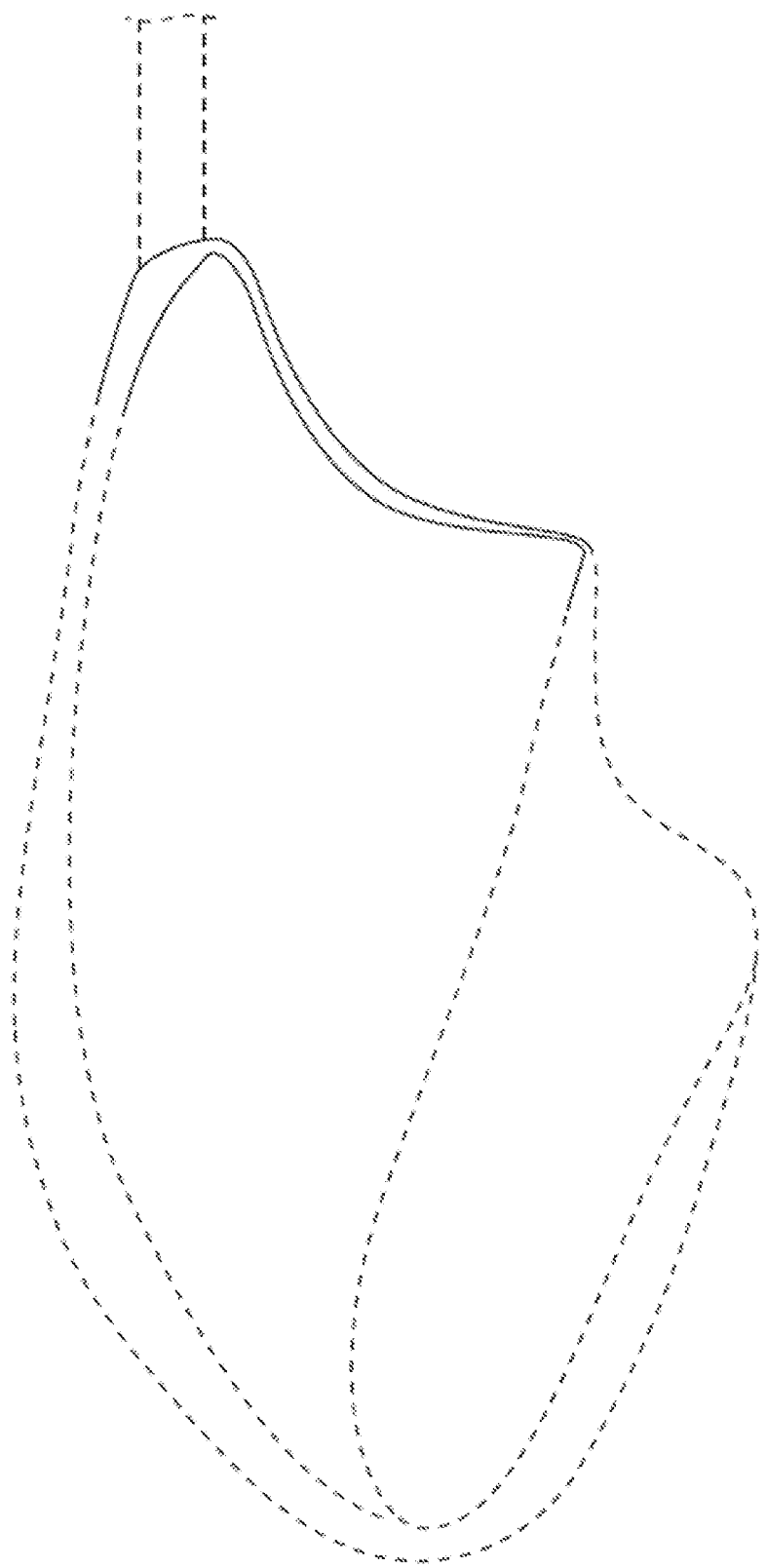
FIG. 5E is a Side 2 view of the handle of FIG. 5A.
Figure 5F:
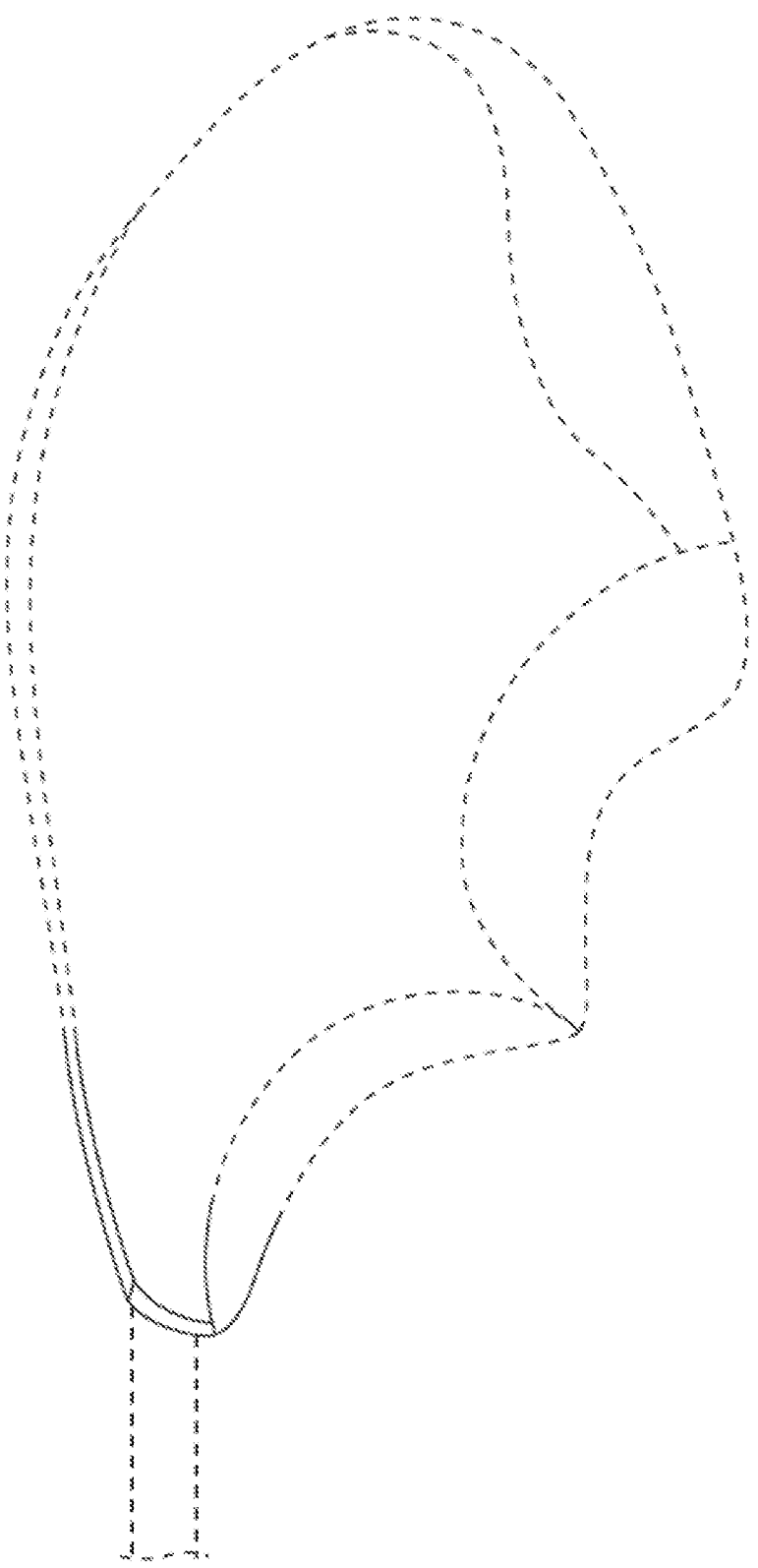
FIG. 5F is a Side 1 view of the handle of FIG. 5A.
Figure 5G:
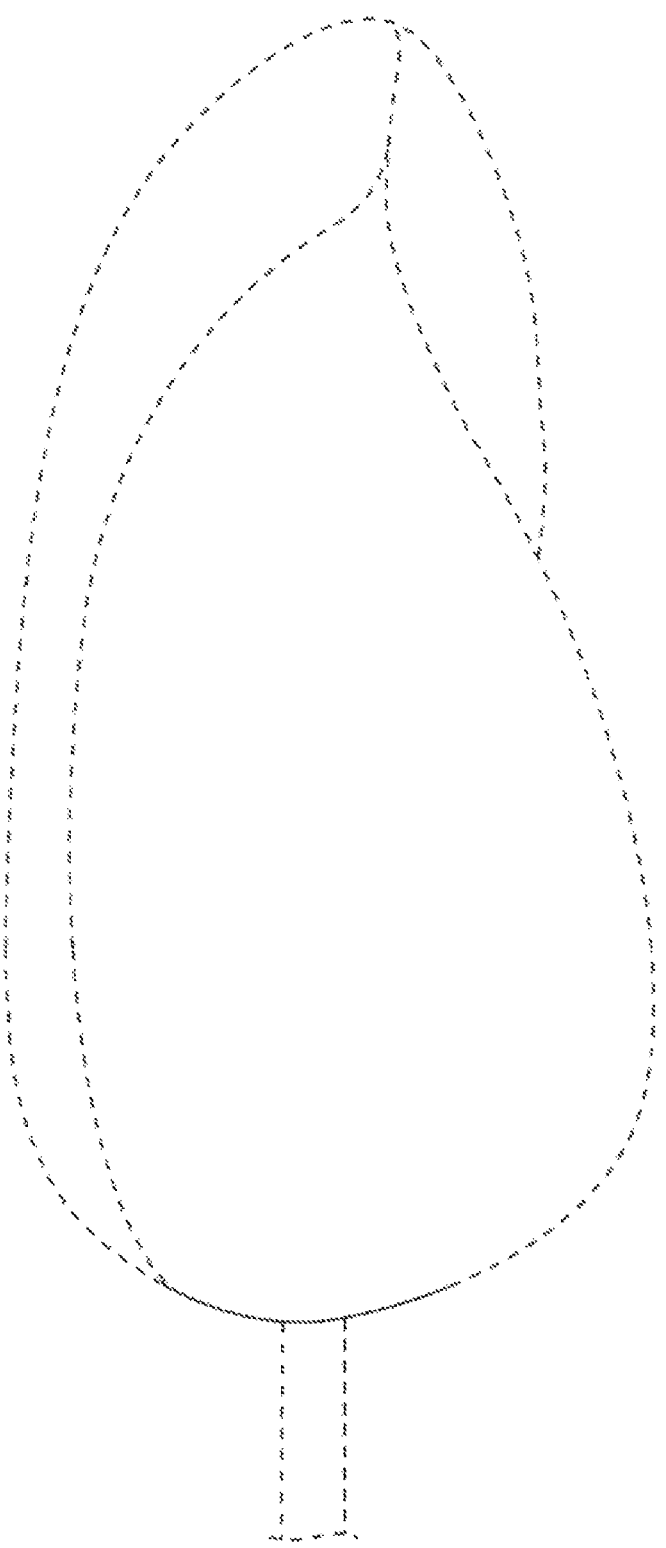
FIG. 5G is a front view of the handle of FIG. 5A.
Figure 5H:
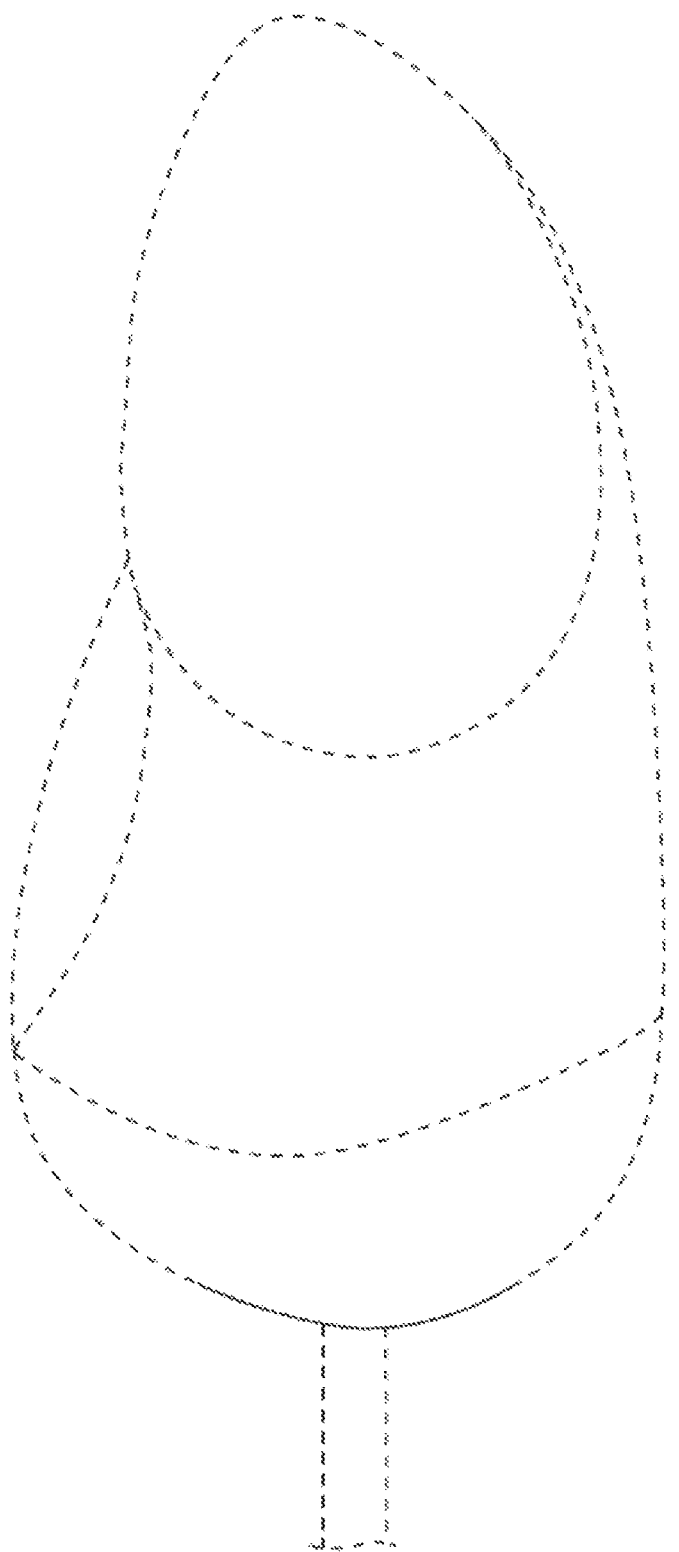
FIG. 5H is a back view of the handle of FIG. 5A.
Figure 6:
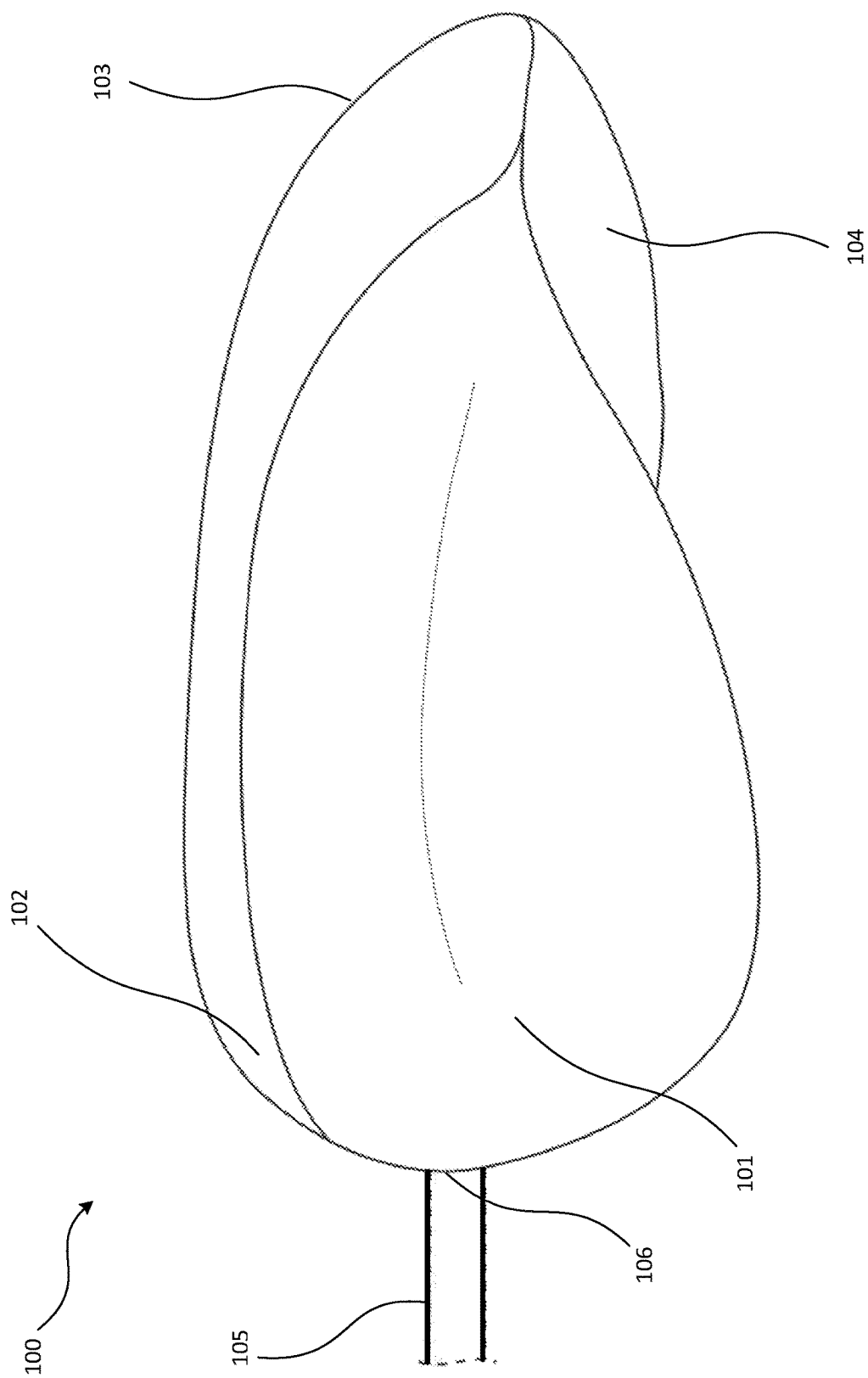
FIG. 6 is a front view of a handle 100, depicting a first surface 101, a ridge 102, a lower surface 103, a cavity 104, an exemplary instrument 105 (e.g. a wand in this embodiment), and an attachment point 106.
Figure 7:
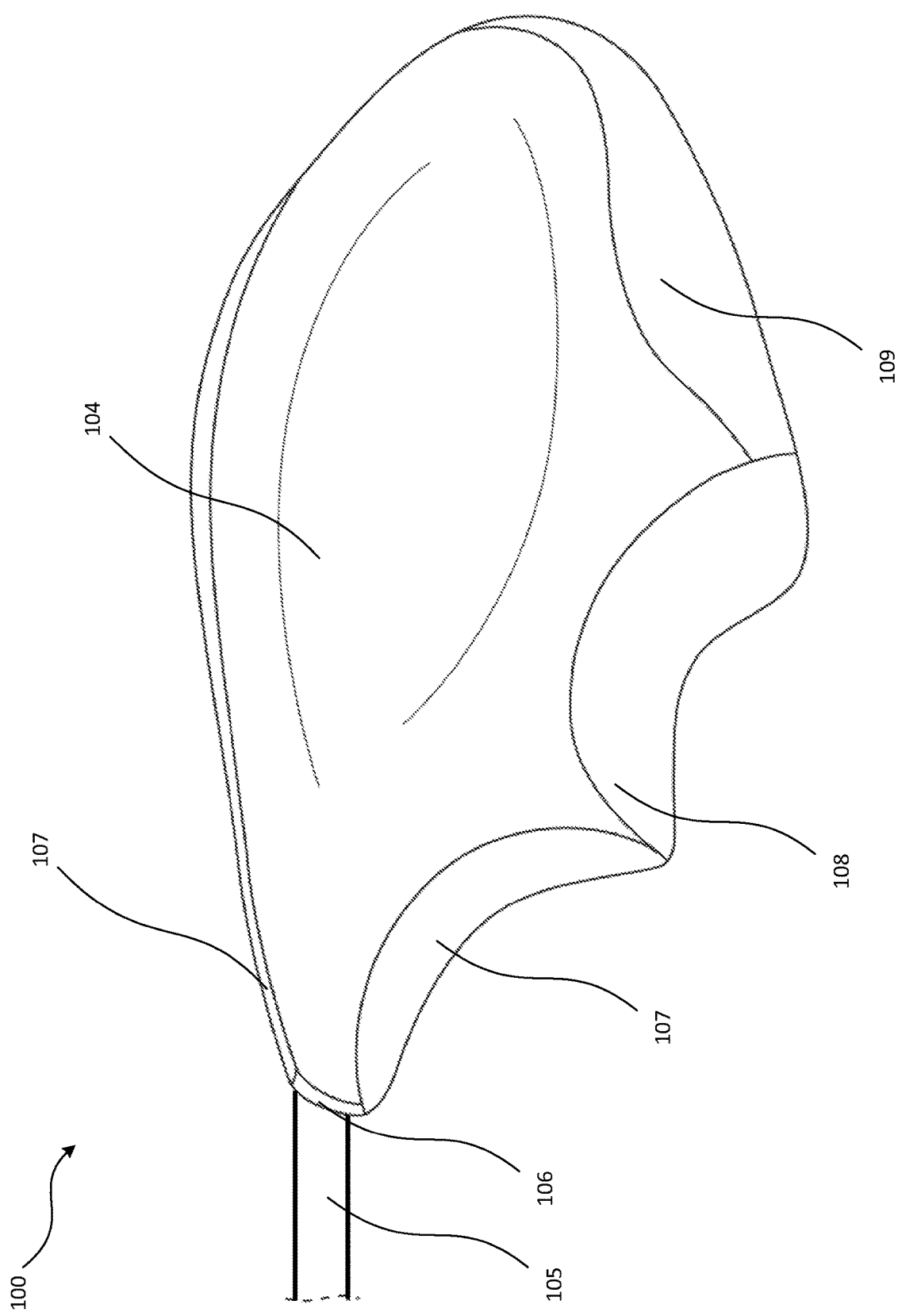
FIG. 7 a Side 1 view of a handle 100, depicting a cavity 104, an exemplary instrument 105 (e.g. a wand in this embodiment), an attachment point 106, a second surface 107, a third surface 108, and a fourth surface 109.
Figure 8:
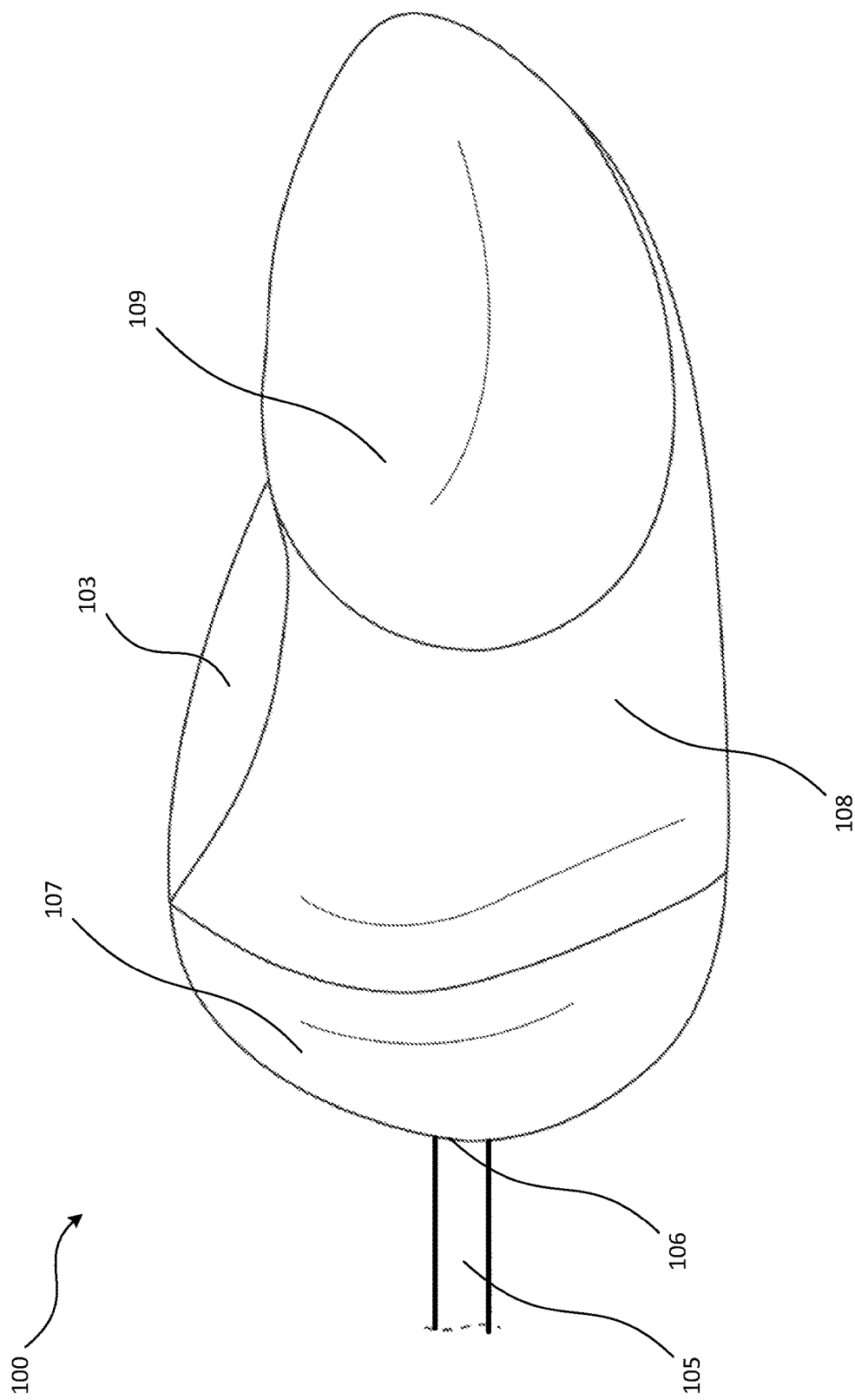
FIG. 8 is a back view of a handle 100, depicting a lower surface 103, an exemplary instrument 105 (e.g. a wand in this embodiment), an attachment point 106, a second surface 107, a third surface 108, and a fourth surface 109.
Figure 9:
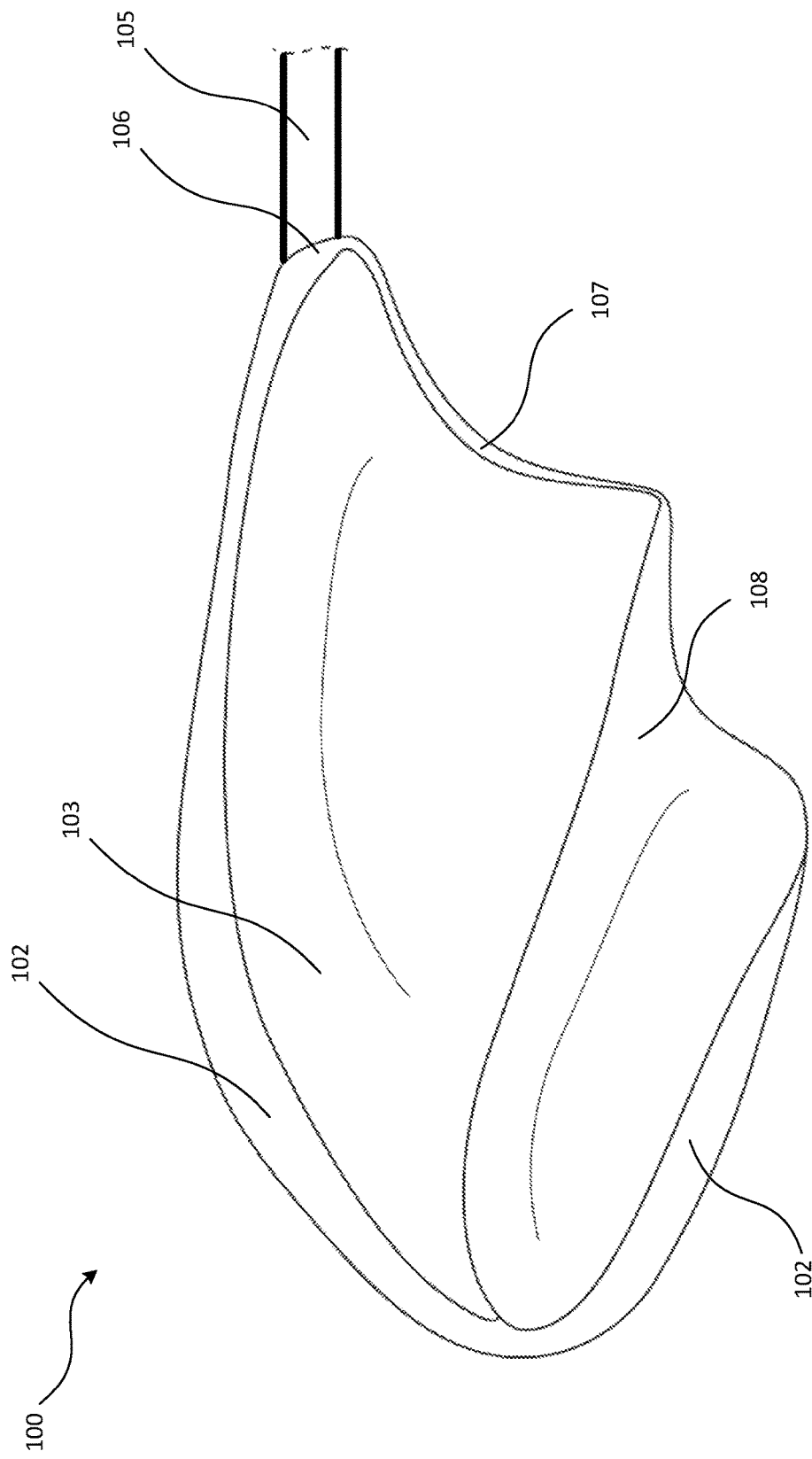
FIG. 9 is a Side 2 view of a handle 100, depicting a ridge 102, a lower surface 103, an exemplary instrument 105 (e.g. a wand in this embodiment), an attachment point 106, a second surface 107, and a third surface 108.

Provided herein are devices, compositions of matter, and methods related to handles, materials for making such handles, and methods of manufacturing and using the same.

Provided herein in some embodiments are handles, such as those comprising one or more surfaces suitable for contacting one or more digits of a user. In some embodiments, the handle is radially asymmetric. In some embodiments, at least one of the one or more surfaces comprises a concave feature. In some embodiments, the volume of the handle is substantially the same as a volume of space created by the user's palm and digits when his or her hand is relaxed. In some embodiments, the volume of the handle is substantially the same as a volume of space created by the user's curved digits and a portion of the user's palm when his or her hand is relaxed. In some embodiments, the handle comprises an attached instrument.

In some embodiments, the disclosed handle translates a user's mental process or intention into physical movement with little or no loss of fidelity of movement. In some embodiments, the disclosed handle allows for seemingly effortless physical movement of the attached instrument by the user. In some embodiments, the disclosed handle allows for movement by the user's arm that resembles the fine motor movement typically only possible using a hand. In some embodiments, the disclosed handle, excluding or including the attached instrument, feels so natural to the user that its presence is forgotten by the user. In some embodiments, the user's mind seamlessly accomplishes a task without the user's conscious thought of the presence of the disclosed handle.

In some embodiments, advantages of the disclosed handle include that the user may relax his or her shoulder and/or hand while using the handle. In some embodiments, an advantage of the handle is that it is lightweight, e.g., as compared to other handles. In some embodiments, the lightweight nature of the handle allows the user to hold and/or use the handle, e.g., working with his or her arm extended, for longer periods of time than with other handles. Typically, even a small amount of extra weight in a handle, particularly a handle with an attached instrument, e.g., that requires precision and/or a user's arm to be extended, can harm the user's health, such as damage a rotator cuff in the user's shoulder. Repetitive motions, such as musical conducting, performing surgeries, cooking, and sports activities may damage muscles and joints, especially when a handle of the musical tool, surgical tool, cooking tool, or sports equipment is heavy. In some embodiments, an advantage of the disclosed handle is that the user is less likely to experience a short-term or long-term injury from using the disclosed handle as compared with other handles or grips, particularly in embodiments where the handle is lightweight. In some embodiments, the lightweight nature of the disclosed handle does not create an imbalance in the user's posture, as compared to other handles when held in one hand. In some embodiments, an advantage of the disclosed handle is that it cannot be dropped accidentally. For example, in some embodiments, the handle does not fall from the user's hand when it is at rest, such as relaxed at the user's side. In some embodiments, an advantage of the provided handles is that the handle may not contain wood, as the wood typically used to make such handles is becoming increasingly scarce. However, in some embodiments, the handle comprises wood.

Handles

Provided in some embodiments are handles comprising one or more surfaces suitable for contacting one or more digits of a user. In some embodiments, the handle may be used as a hand grip for a variety of tools and instruments, such as musical tools (e.g., conducting batons), surgical tools (e.g., scalpels), cooking tools (e.g., whisks), and sports equipment (e.g., golf clubs).

In some embodiments, a volume of the handle is substantially the same as a volume of space created by the user's palm and digits when his or her hand is relaxed. In some embodiments, a volume of the handle is substantially the same as a volume of space created by the user's curved digits and a portion of the user's palm when his or her hand is relaxed. In some embodiments, the portion of the user's palm comprises about 50% of the user's palm. In some embodiments, the portion of the user's palm is a portion above a line between the user's thumb and pinky finger. In some embodiments, the handle occupies approximately 10%, 20%, 30%, 40%, 50%, 60%, 70%, 80%, 90%, 100% or any percentage in between of the volume of the user's hand. In some embodiments, the handle occupies about half of the volume of the user's hand.

In some embodiments, the volume of the handle is between or between about 1 in$^3$ and 8 in$^3$, 2 in$^3$ and 6 in$^3$, or 2 in$^3$ and 4 in$^3$, inclusive of the endpoints. In some embodiments, the volume of the handle is or is about 2 in$^3$ or 3 in$^3$, inclusive of the endpoints. In some embodiments, the volume of the handle is or is about 2.25 in$^3$.

In some embodiments, the handle is an average size, e.g., fits in an average-sized relaxed hand of a user. In some embodiments, the handle is a scaled-down version of an average-sized handle. For example, in some embodiments, the handle comprises a volume that is scaled down from the average size. In some embodiments, the handle is a scaled-up version of an average-sized handle.

In some embodiments, the handle is radially asymmetric. In some embodiments, the handle is asymmetric on one or more planes. In some embodiments, the handle is symmetric on one or more planes. In some embodiments, at least one of the one or more surfaces comprises a concave feature. In some embodiments, the concave feature is designed to match the shape of a user's digit or digits. In some embodiments, the handle has a shape resembling a mold of a handshake or hand grasp.

In some embodiments, the handle is handed, e.g., designed to accommodate a right hand or a left hand of the user. In some embodiments, the handle is designed to accommodate either the left hand or the right hand of the user.

In some embodiments, the one or more surfaces comprise a first surface suitable for contacting a first digit of the user and a second surface suitable for contacting a second digit of the user. In some embodiments, the one or more surfaces further comprise a third surface suitable for contacting a third digit of the user. In some embodiments, the one or more surfaces further comprise a fourth surface suitable for contacting a fourth digit of the user. In some embodiments, the handle further comprises a cavity. In some embodiments, the handle further comprises a lower surface.

In some embodiments, at least one of the first surface, second surface, third surface, fourth surface, cavity, or lower surface comprises a concave feature. In some embodiments, two or more of the first surface, second surface, third surface, fourth surface, cavity, or lower surface comprise a concave feature. In some embodiments, three or more of the first surface, second surface, third surface, fourth surface, cavity, or lower surface comprise a concave feature. In some embodiments, four or more of the first surface, second surface, third surface, fourth surface, cavity, or lower surface comprise a concave feature. In some embodiments, five or more of the first surface, second surface, third surface, fourth surface, cavity, or lower surface comprise a concave feature. In some embodiments, the first surface, second surface, third surface, fourth surface, cavity, and lower surface each comprises a concave feature.

In some embodiments, at least one of the first surface, second surface, third surface, fourth surface, cavity, or lower surface comprises a convex feature. In some embodiments, two or more of the first surface, second surface, third surface, fourth surface, cavity, or lower surface comprise a convex feature. In some embodiments, three or more of the first surface, second surface, third surface, fourth surface, cavity, or lower surface comprise a convex feature. In some embodiments, four or more of the first surface, second surface, third surface, fourth surface, cavity, or lower surface comprise a convex feature. In some embodiments, five or more of the first surface, second surface, third surface, fourth surface, cavity, or lower surface comprise a convex feature.

In some embodiments, the first surface, second surface, third surface, fourth surface, cavity, and lower surface each comprises a convex feature.

In some embodiments, the second surface is separated from the first surface by a ridge. In some embodiments, the ridge is an area of changed concavity. In some embodiments, the ridge comprises a convex feature. In some embodiments, the third surface is adjacent to the second surface. In some embodiments, the fourth surface is adjacent to the third surface. In some embodiment, the cavity is adjacent to the second surface, third surface, and fourth surface. In some embodiments, the lower surface is adjacent to the ridge, the second surface, and the third surface.

In some embodiments, the handle can be oriented to have a top, a bottom, and one or more sides. In some embodiments, the handle can be oriented to have a front, a back, and one or more sides.

In some embodiments, the orientation of the one or more surfaces, ridge, and cavity on the front of the handle from top to bottom is the ridge, the first surface, and the cavity. In some embodiments, the orientation of the one or more surfaces, ridge, and cavity on the back of the handle is the ridge, the second surface, the third surface, and the fourth surface. In some embodiments, the orientation of the one or more surfaces, ridge, and cavity on a first side of the handle is the ridge, the second surface, and the lower surface. In some embodiments, the orientation of the one or more surfaces, ridge, and cavity on a second side of the handle is the ridge, the second surface, the lower surface, the third surface, and the forth surface.

In some embodiments, the orientation of the one or more surfaces, ridge, and cavity clockwise around the handle is the first surface; the ridge; the cavity; the second, third, and fourth surfaces; the lower surface; the ridge; and returning back to the first surface. In some embodiments, the ridge surrounds all or part of the one or more surfaces, e.g., the first surface.

In some embodiments, the orientation of the one or more surfaces, ridge, and cavity counterclockwise around the handle is the first surface; the ridge; the cavity; the second, third, and fourth surfaces; the lower surface; the ridge; and returning back to the first surface. In some embodiments, the ridge surrounds all or part of the one or more surfaces, e.g., the first surface.

In some embodiments, two or more of the surfaces and/or cavity converge or share an area of the handle. In some embodiments, the one or more surfaces, ridge, and/or cavity converge at a tip at the bottom of the handle. In some embodiments, the third surface, fourth surface, cavity, and ridge converge, e.g., at the tip of the handle. In some embodiments, the first surface, third surface, fourth surface, cavity, and ridge converge, e.g., at the tip of the handle. In some embodiments, the third surface and forth surface converge, e.g., at the tip of the handle. In some embodiments, the ridge, lower surface, third surface and/or fourth surface converge, e.g., at the tip of the handle. In some embodiments, the cavity, fourth surface, and/or ridge converge, e.g., at the tip of the handle. In some embodiments, any combination of the first surface, second surface, third surface, fourth surface, lower surface, cavity, and/or ridge converge at one or more points.

In some embodiments, the handle comprises one or more attachment points. In some embodiments, the handle comprises one attachment point. In some embodiments, the handle comprises or comprises at least or about 2, 3, 4, 5, 6, 7, 8, 9, 10, 15, 20, or 50 attachment points. In some embodiments, the handle comprises or comprises at least or about 2, 3, 4, 5, 6, 7, 8, 9, 10, 15, 20, 50 attachment points or any value in between. In some embodiments, at least one of the one or more attachment points is located on or within the ridge. In some embodiments, at least one of the one or more attachment points is located on or within the first surface. In some embodiments, at least one of the one or more attachment points is located on or within the second surface. In some embodiments, at least one of the one or more attachment points is located on or within the third surface. In some embodiments, at least one of the one or more attachment points is located on or within the forth surface. In some embodiments, at least one of the one or more attachment points is located on or within the cavity. In some embodiments, at least one of the one or more attachment points is located on or within the lower surface. In some embodiments, at least one of the one or more attachment points is located on or within the tip.

In some embodiments, the handle further comprises one or more instruments attached at the one or more attachment points. In some embodiments, the handle comprises one instrument attached at a single attachment point. In some embodiments, the handle comprises one instrument attached at multiple, e.g., 2 or more, attachment points. In some embodiments, the handle comprises or comprises at least or about 2, 3, 4, 5, 6, 7, 8, 9, 10, 15, 20, 50 instruments attached at the one or more attachment points. In some embodiments, the handle comprises or comprises at least or about 2, 3, 4, 5, 6, 7, 8, 9, 10, 15, 20, 50 instruments attached or any value in between attached at the one or more attachment points.

In some embodiments, the instrument is permanently attached to the handle. In some embodiments, the instrument is detachable from the handle. In some embodiments, the instrument can be unscrewed from the handle. In some embodiments, the instrument can be detached from the handle and a different instrument may be attached to the same handle.

In some embodiments, the one or more instruments comprises a musical tool, a surgical tool, a cooking tool, or a sporting equipment (including for use as a handle for one or more instruments or controls on a dashboard or interior of a luxury, sport, or racing automobile).

In some embodiments, the instrument is a wand. In some embodiments, the instrument is a stick. In some embodiments, the instrument is a musical instrument and is a wand or stick, e.g., a conducting wand or stick. In some embodiments, the instrument is a wand or stick and the musical tool is a baton, e.g., a conducting baton. Thus, in some embodiments, the handle comprises a wand attached at the attachment point and the handle with the attached wand constitutes a baton, e.g., a conducting or conductor's baton.

In some embodiments, the instrument is a scalpel. Thus, in some embodiments, the handle with a scalpel attached at the attachment point comprises a surgical tool. In some embodiments, the instrument is a scalpel and the scalpel is made from surgical grade steel. In some embodiments, the scalpel is detachable. In some embodiments, the scalpel is disposable. In some embodiments, the scalpel blade and the handle are both made from material that can withstand the temperature and pressure conditions of an autoclaving process such that the scalpel can be sterilized after use.

In some embodiments, the handle and/or instrument can be subjected to sterilization, e.g., heat sterilization, UV light, or chemicals such as iodine, betadine, and alcohol. In some embodiments, the handle and/or instrument is not degraded or adversely affected by sterilization with heat, e.g., extreme heat, UV light, or chemicals.

In some embodiments, the handle is composed of one or more materials, such as two or more materials, three or more materials, four or more materials, five or more materials, six or more materials, seven or more materials, eight or more materials, nine or more materials, ten or more materials, or more. In some embodiments, the handle comprises a resin, a hardener (e.g., hardening agent or curing agent), and/or a filler.

In some embodiments, the handle comprises a resin. In some embodiments, the resin comprises an epoxy resin, a vinyl ester resin, a liquid plastic casting (e.g., Smooth-On FEATHER LITE), a polyurethane, silicone, acrylic, or polyester.

In some embodiments, the resin comprises epoxy resin. In some embodiments, the epoxy resin comprises alkylene oxides, alkenyl oxides, glycidyl esters, glycidyl ethers, epoxy novolacs, copolymers of acrylic acid esters of glycidol and copolymerizable vinyl compounds, polyurethane polyepoxides, or a mixture thereof. In some embodiments, the epoxy resin comprises a 5-minute, 6-minute, 10-minute, 30-minute, or 60-minute epoxy resin. In some embodiments, the epoxy resin comprises 30-minute epoxy resin. For example, in some embodiments, the epoxy resin comprises Great Planes 30 Minute Pro Epoxy Resin (e.g., Cat. No. GPMR6043 or GPMR6047), or any other commercially available resin.

In some embodiments, the resin comprises a vinyl ester resin (e.g., Fibre Glast® 1100 Vinyl Ester Resin, low viscosity).

In some embodiments, the handle comprises a hardener (e.g., hardening agent or curing agent). In some embodiments, the hardener comprises an epoxy hardener, a phenalkamine, an aromatic amine, a modified amine, an aliphatic amine, a modified aliphatic amine, a cycloaliphatic amine, an imidazole, a polymercaptan agent (e.g., liquid polymercaptan), a polysulfide resin, a phenolic agent, an anhydride, a latent curing agent, a boron trifluoride-amine complex, a dicyandiamide, an organic acid hydrazide, a waterborne agent, a polyamine, a modified polyamine, a photo-curing agent, or an ultraviolet-curing agent.

In some embodiments, the hardener comprises epoxy hardener. In some embodiments, the epoxy hardener comprises a 5-minute, 6-minute, 10-minute, 30-minute, or 60-minute epoxy hardener. In some embodiments, the epoxy hardener comprises 30-minute epoxy hardener. For example, in some embodiments, the epoxy hardener comprises Great Planes 30 Minute Pro Epoxy Hardener (e.g., Cat. No. GPMR6043 or GPMR6047), or any other commercially available hardener.

In some embodiments, the hardener (e.g., hardening agent or curing agent) comprises a vinyl ester hardener.

In some embodiments, the handle comprises a filler. In some embodiments, the filler comprises a nanoparticle, nanofiber, nanometal, micro-fiber, micro-glass bead, micro-glass sphere (e.g., glass microspheres, micro glass balls), epoxy, wood, cork, glass beads, silica, carbon nanotubes, graphene, ceramic, cellulose, woven polyester, non-woven polyester, woven glass, non-woven glass, glass frit, ceramic frit, metal woven screen, or metal non-woven screen.

In some embodiments, the filler comprises glass microspheres, e.g., glass microbeads or glass microballs. For example, in some embodiments, the filler comprises glass microspheres such as System Three® 3145S16 White Glass Microspheres, or any other suitable commercial microspheres.

In some embodiments, one or more of the one or more surfaces may be textured. Thus, in some embodiments one or more of the first surface, second surface, third surface, fourth surface, lower surface, ridge, or cavity may be textured. In some embodiments, texture facilitates the user's grip of the handle, prevents the handle from slipping, and/or provides a drier surface, e.g., to provide more comfort or control when sweat is present.

In some embodiments, the handle comprises an instrument. In some embodiments, the instrument is attached to the handle, such as at an attachment point. In some embodiments, the instrument may be any instrument that is capable of being attached to the handle. In some embodiments, the instrument is a wand, such as that used by a conductor, e.g., orchestra conductor. In some embodiments, the handle with an attached wand comprises In some embodiments, the baton has a balance point in the handle. In some embodiments, the baton has a balance point in the wand, such as just above the handle. In some embodiments, the balance point of the wand is customized for a particular user. In some embodiments, the balance point is determined by the weight distribution in the handle. In some embodiments, the balance point of the baton is within the handle. In some embodiments, the balance point of the baton is or substantially is the surface of the handle at the point where the wand is coupled to the handle. Without wishing to be bound by any particular theory, when the balance point of the apparatus is at or substantially at the end of the user's hand or before the end of the user's hand when grasping the handle, the material extending beyond the balance point, for example, the wand in the case of a conductor's baton, may have a lesser or no perceived weight and/or a lesser or no perceived affect to the dynamic human motor control of the user's hand by the user. Dynamic human motor control is learned control of the human body through experiential learning, e.g., by moving the arm sporadically as an infant or child and having progressively more control of arm movement due to neurological development and muscle/tendon/joint development. In other words, when the balance point of the apparatus is at the end of the handle or within the handle, the user experiences no extension of their extremity (e.g., user's hand) for purposes of human motor control during use of the apparatus. In other embodiments, wherein the apparatus is a scalpel comprising a handle and a blade, fine human motor control may be necessary to successfully operate the scalpel to make a precise cut during surgery, in which case the position of the balance point in the scalpel can lead the user to make more fluid, controlled, and precise movements with the scalpel during use. In other embodiments, wherein the apparatus is a gaming device configured to be in remote communication with a gaming console, fine human motor control may be necessary to successfully operate the gaming device, buttons or other engagement devices, or the position and/or orientation of the gaming device in space to send timely and precise in-game instructions to the console during game play, in which case the position of the balance point in the gaming device can lead the user to make more fluid, controlled, and precise movements with the gaming device during use.

In some embodiments, the instrument is a surgical instrument. In some embodiments, the surgical instrument is a scalpel. In some embodiments, the instrument is a cooking instrument. In some embodiments, the cooking instrument is a whisk. In some embodiments, the instrument includes sports equipment. In some embodiments, the sports equipment includes a golf club or a fishing rod. In some embodiments, the handle is attached to any instrument, such as one that requires precision by a user.

In some embodiments, the handle does not contain at attachment point. In some embodiments, the handle does not comprise an attached instrument. In some embodiments, the handle can be used as a doorknob. In some embodiments, the handle can be used as a computer device, such as a computer mouse.

In some embodiments, the user is an adult human, such as an adult male or female. In some embodiments, the user is a child, such as a male child or a female child. Thus, in some embodiments, the handle designed for a smaller user, e.g., child user, is scaled down in one or more dimension (e.g., height, width, length, and the like), in mass, and/or in volume.

Provided in some embodiments are methods of manufacturing a handle. In some embodiments, the provided methods produce a handle as described herein.

In some embodiments, the method comprises mixing a resin with a hardener (e.g., hardening agent or curing agent) and a filler to produce an initial mixture. In some embodiments, the method comprises adding the initial mixture into a mold. In some embodiments, the method comprises incubating the initial mixture to produce a solid mixture. In some embodiments, the method comprises removing the solid mixture from the mold. In some embodiments, the method comprises sanding the solid mixture to produce a sanded handled.

In some embodiments, the method further comprises lubricating the mold or molds prior to the addition of the initial mixture. In some embodiments, lubricating is accomplished through the use of a lubricant. For example, in some embodiments, a lubricant spray such as GREASE-IT Release Systems (Hapco, Inc.) or any other suitable lubricant, e.g., commercially available lubricant, may be used.

EXAMPLES

Example 1: Process of Manufacturing Handle Mold

About 15 g of 30-minute epoxy resin was mixed with about 15 g of epoxy hardener (Great Planes® 30 minute Pro Epoxy kit; Cat. No. GPMR6043 or GPMR6047). The resin/hardener was stirred until opaque. About 7.5 g of glass microspheres (System Three® 3145S16 White Glass Microspheres) were added to the resin/hardener to produce an imprint mixture. The imprint mixture was kneaded by hand until smooth and to remove air bubbles. The mixture was rolled into a ball by hand. An imprint of the model user's hand was taken by having the model user grasp and squeeze the imprint mixture (as they would hold the handle, e.g., as a handle for a conducting baton), thus producing an imprint model. A wand, coated with a lubricant (GREASE-IT; Release Systems. Hapco, Inc.), was inserted into a ridge formed at the top of the imprint model. The imprint model was incubated at room temperature for about 30 minutes. The imprint model was then carved to remove any unnecessary portions, e.g., portions extending outside the volume of the model user's hand. The imprint model was sanded to round the edges and smooth the surface. The imprint model was polished to be smooth. The imprint model was then place with its front side down in a first bath of liquid silicone so that about one half of its volume was submerged in the liquid. The liquid was allowed to solidify and the imprint model was removed, thus producing a first portion of the mold. The imprint model was then placed with its back side down into a second bath of liquid silicone such that about one half (the opposite half) of its volume was submerged in the liquid. The silicone was allowed to solidify and the imprint model was removed, thus producing a second portion of the mold. The two portions constituted the mold. The mold was used to produce handles as described herein. The wand was removed, thus leaving an attachment point within the ridge of the imprint model.

Additional molds were made as described using imprints from other, additional model users, including musical conductors.

Example 2: Process of Manufacturing Baton

The mold of Example 1 was used to produce handles as described herein. About 15 g of 30-minute epoxy resin was mixed with about 15 g of epoxy hardener (Great Planes® 30 minute Pro Epoxy kit; Cat. No. GPMR6043 or GPMR6047) and about 7.5 g of glass microspheres (System Three® 3145S16 White Glass Microspheres) to produce an initial mixture. The initial mixture was kneaded by hand to remove air bubbles. The mold was sprayed with a lubricant (GREASE-IT; Release Systems. Hapco, Inc.) for ease of removal the molded mixture. About half of the initial mixture was added to each of the two portions of the mold by pressing it in by hand. The initial mixture was incubated until solidified, e.g., for about 60 minutes. The initial mixture was removed from the two portions of the mold as two fractions.

The fractions were carved to hollow out an inner portion of each, thereby reducing the mass of each fraction. The two fractions were then combined using epoxy resin and epoxy hardener. The solid mixture was carved to smooth edges and sanded to remove imperfections and make smooth, thereby producing a sanded handle. The handle was painted (i.Color® 2.1 Voc Direct to Metal Epoxy Hybrid Primer and primer activator) and lacquered (High Teck 7100-1 MS Urethane Clear).

A fiberglass or carbon fiber wand (either a new wand or the one that was used for manufacturing the mold) was affixed at the attachment point using epoxy resin and epoxy hardener. If the wand was not already white, it was painted white to facilitate visibility. Thus, the method produced a baton, e.g., conducting baton, comprising the handle with the wand attached. The baton is used by a musical conductor for conducting music.

The method was repeated to make additional handles using the same mold and additional molds.

Example 3: Process of Manufacturing Handle Using 3D Printer

About 15 g of 30-minute epoxy resin is mixed with about 15 g of epoxy hardener (Great Planes® 30 minute Pro Epoxy kit; Cat. No. GPMR6043 or GPMR6047). The resin/hardener is stirred until opaque. About 7.5 g of glass microspheres (System Three® 3145S16 White Glass Microspheres) is added to the resin/hardener to produce an imprint mixture. The imprint mixture is kneaded by hand until smooth and to remove air bubbles. The mixture is rolled into a ball by hand. An imprint of the model user's hand is taken by having the model user grasp and squeeze the imprint mixture (as they would hold the handle, e.g., as a handle for a conducting baton), thus producing an imprint model. The imprint model is incubated at room temperature for about 30 minutes. The imprint model is then carved to remove any unnecessary portions, e.g., portions extending outside the volume of the model user's hand. The imprint model is sanded to round the edges and smooth the surface. The imprint model is polished to be smooth. The imprint model is then photographed to generate digital images of the imprint model that is read by a computer program operable to interpret dimensional information from the digital images of the imprint model. The dimensional information is then input to a 3D printer (e.g., a FormLabs™ 3D printer) to print a substantially precise copy of the imprint model using the desired material or materials. The substantially precise copy is then removed from the 3D printer and trimmed to remove any anchor points or other imperfections as a result of the printing process. The trimmed imprint model is then coated or otherwise treated to produce the finished handle. A portion of the finished handle is then removed to form a channel into which at least a portion of the instrument can be disposed to couple the handle to the instrument.

Additional handles are made as described using imprints from other, additional model users.

INCORPORATION BY REFERENCE

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

OTHER EMBODIMENTS

While particular embodiments of the disclosure have been illustrated and described, various other changes and modifications can be made without departing from the spirit and scope of the disclosure. The scope of the appended claims includes all such changes and modifications that are within the scope of this disclosure.

What is claimed is:

1. A handle comprising:
one or more surfaces suitable for contacting one or more digits of a user, wherein the handle is radially asymmetric,
wherein the one or more surfaces comprise a first surface suitable for contacting a first digit of the user and a second surface suitable for contacting a second digit of the user;
wherein at least one of the one or more surfaces comprises a concave feature,
wherein the second surface is separated from the first surface by a ridge,
wherein a volume of the handle is substantially the same as a volume of space created by the user's curved digits and a portion of the user's palm when his or her hand is relaxed, and
wherein the portion of the user's palm comprises less than 50% of the user's palm and the portion of the user's palm is a portion above an imaginary line extending from the user's thumb to the user's pinky finger when the user's thumb is positioned above the user's pinky finger.

2. The handle of claim 1, wherein the one or more surfaces further comprise a third surface suitable for contacting a third digit of the user.

3. The handle of claim 2, wherein the one or more surfaces further comprise a fourth surface suitable for contacting a fourth digit of the user.

4. The handle of claim 3, wherein the fourth surface is adjacent to the third surface.

5. The handle of claim 3, further comprising:
a cavity adjacent to the second surface, third surface, and fourth surface.

6. The handle of claim 5, wherein the cavity is separated from the first surface by the ridge.

7. The handle of claim 2, wherein the third surface is adjacent to the second surface.

8. The handle of claim 2, further comprising:
a lower surface adjacent to the ridge, the second surface, and the third surface.

9. A method of manufacturing the handle of claim 1, comprising using a high-throughput manufacturing method.

10. The method of claim 9, wherein the high-throughput method comprises 3D printing, 4D printing, stamping, blow molding, and/or injection molding.

11. A handle comprising:
a) a first surface suitable for contacting a first digit of a user;
b) a second surface suitable for contacting a second digit of the user, wherein the second surface is separated from the first surface by a ridge;
c) a third surface suitable for contacting a third digit of the user, wherein the third surface is adjacent to the second surface;
d) a fourth surface suitable for contacting a fourth digit of the user, wherein the fourth surface is adjacent to the third surface;
e) a cavity adjacent to the second surface, third surface, and fourth surface, wherein the cavity is separated from the first surface by the ridge; and
f) a lower surface adjacent to the ridge, the second surface, and the third surface;
wherein the handle is radially asymmetric;
wherein at least one of the first surface, second surface, third surface, or fourth surface comprises a concave feature;
wherein a volume of the handle is substantially the same as a volume of a space created by the user's curved digits and a portion of the user's palm when his or her hand is relaxed, and
wherein the portion of the user's palm comprises less than 50% of the user's palm and the portion of the user's palm is a portion above an imaginary line extending from the user's thumb to the user's pinky finger when the user's thumb is positioned above the user's pinky finger.

12. A method of manufacturing the handle of claim 11, comprising using a high-throughput manufacturing method.

13. The method of claim 12, wherein the high-throughput method comprises 3D printing, 4D printing, stamping, blow molding, and/or injection molding.

14. A handle 100 comprising:
a) a first surface 101 suitable for contacting a first digit of a user;
b) a second surface 108 suitable for contacting a second digit of the user, wherein the second surface 108 is separated from the first surface 101 by a ridge 102;
c) a third surface 109 suitable for contacting a third digit of the user, wherein the third surface 109 is adjacent to the second surface 108;

d) a fourth surface 110 suitable for contacting a fourth digit, wherein the fourth surface 110 is adjacent to the third surface 109;

e) a cavity 104 adjacent to the first surface 101, second surface 108, third surface 109, and fourth surface 110, wherein the cavity 104 is separated from the first surface 101 by the ridge 102;

f) a lower surface 103 adjacent to the ridge 102, the second surface 108, and the third surface 109; and g) an attachment point 106 on or within the ridge 102, wherein a wand 105 is attached to the handle at the attachment point 106;

wherein the handle 100 is radially asymmetric;

wherein at least one of the first surface 101, second surface 108, third surface 109, fourth surface 110, lower surface 103, and cavity 104 comprises a concave feature; and wherein the volume of the handle 100 is substantially the same as a volume of a space between a user's palm and digits when his or her hand is relaxed.

15. A method of manufacturing the handle of claim 14, comprising using a high-throughput manufacturing method.

16. The method of claim 15, wherein the high-throughput method comprises 3D printing, 4D printing, stamping, blow molding, and/or injection molding.

* * * * *